US009775870B2

(12) United States Patent
Park et al.

(10) Patent No.: US 9,775,870 B2
(45) Date of Patent: Oct. 3, 2017

(54) MEDICINAL PLANTS EXTRACT USING PROCESSING OF HERBAL MEDICINE AND COMPOSITION OF SKIN EXTERNAL APPLICATION COMPRISING THE SAME

(71) Applicant: AMOREPACIFIC CORPORATION, Seoul (KR)

(72) Inventors: Jun Seong Park, Suwon-si (KR); Hye Yoon Park, Anyang-si (KR); Dong Hyun Kim, Uiwang-si (KR); Eun Jeong Moon, Seoul (KR); Ji Hye Chung, Seongnam-si (KR); Jae Kyoung Lee, Seoul (KR); Duck Hee Kim, Seoul (KR); Han Kon Kim, Suwon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/093,089

(22) Filed: Apr. 7, 2016

(65) Prior Publication Data

US 2016/0220622 A1 Aug. 4, 2016

Related U.S. Application Data

(62) Division of application No. 13/317,410, filed on Oct. 18, 2011, now Pat. No. 9,327,007, which is a division of application No. 12/990,699, filed as application No. PCT/KR2008/006545 on Nov. 6, 2008, now Pat. No. 8,784,903.

(30) Foreign Application Priority Data

May 2, 2008 (KR) ........................ 10-2008-0041544

(51) Int. Cl.
*A61K 36/00* (2006.01)
*A61K 36/185* (2006.01)
*A61K 36/28* (2006.01)
*A61K 36/287* (2006.01)
*A61K 36/428* (2006.01)
*A61K 36/232* (2006.01)
*A61K 36/45* (2006.01)
*A61K 36/732* (2006.01)
*A61K 36/8945* (2006.01)
*A61K 36/78* (2006.01)
*A23L 33/105* (2016.01)

(52) U.S. Cl.
CPC .......... *A61K 36/185* (2013.01); *A23L 33/105* (2016.08); *A61K 36/232* (2013.01); *A61K 36/28* (2013.01); *A61K 36/287* (2013.01); *A61K 36/428* (2013.01); *A61K 36/45* (2013.01); *A61K 36/732* (2013.01); *A61K 36/78* (2013.01); *A61K 36/8945* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,528,192 | A | 7/1985 | Kim |
| 5,965,145 | A | 10/1999 | Marion et al. |
| 2003/0143289 | A1 | 7/2003 | Chen |
| 2005/0186172 | A1 | 8/2005 | Courtin |
| 2007/0258995 | A1 | 11/2007 | Chan |

FOREIGN PATENT DOCUMENTS

| | | |
|---|---|---|
| CN | 20071135044 | 10/2007 |
| CN | 101143190 | 3/2008 |
| CN | 101167936 | 4/2008 |
| JP | 5-331041 | 12/1993 |
| KR | 2003-0064107 A | 7/2003 |
| KR | 10-0669362 | 1/2007 |
| KR | 2007012755 A * | 1/2007 |

OTHER PUBLICATIONS

Li et al, Study of the honey-processing technologies for preparing aconitum carmichaeli and the quantitative determination of its main alkaloids. Beijing Zhongyiyao Daxue Xuebao (2003), 26(6), 57-59, 60.*
Antimicrobial and antioxidant activities of Cortex Magoliae Officinalis and some other medicinal plants commonly used in South-East Asia (Chan W et al, Chinese Medicine, Bliomed Central Ltd., LO, vol. 3, Nov. 28, 2008, pp. 15-24).
Antioxidant and nitric oxide xynthase activation properties of Ganoderma applanatum (Aharya Krishnendu et al, Indian Journal of Experimental Biology, Council of Scientific & Industrial Research, IN, vol. 43, No. 10, Oct. 1, 2005, pp. 926-929).
Assessment of membrane protection by traditional Chinese medicines using a flow cytometric technique: preliminary findings (Chung Wai Y et al, Redox Report, Churchill Livingstone, Edinburgh, GB, vol. 8, No. 1, Jan. 1, 2003, pp. 31-33).
Bum Chun Lee et al., "Effect of the Processed Selaginella Tamariscina on Antioxidation and Inhibition of Matrix Metalloproteinase", J. Soc. Cosmet. Scientists Korea, vol. 32, No. 2, (Jun. 2006), pp. 69-74.
Chemistry of Traditional Chinese Medicine (Xiao Chonghou, Shanghai Science and Technology Press, 1$^{st}$ Edition published in Jun. 1997, and 5$^{th}$ Edition published in May 2001) (with English translation of relevant portion).
European Search Report in EP 08 87 4126 dated Aug. 4, 2011.
First Notification of Office Action (with English translation) in CN 200880128875.2 dated Dec. 19, 2011.

(Continued)

*Primary Examiner* — Qiuwen Mi
(74) *Attorney, Agent, or Firm* — Nixon & Vanerhye P.C.

(57) ABSTRACT

The present invention relates to an extract of a processed herbal medicinal plant and a composition for skin external application which contains the extract. More specifically, the composition for skin external application contains an extract of processed herbal medicinal plant, prepared through a method comprising the steps of: (a) processing an herbal medicinal plant by a process of boiling, steaming, roasting, baking or heating the medicinal plant or a combination of two or more of these processes; (b) obtaining an extract of the processed medicinal plant. The composition shows an improved antioxidant effect.

3 Claims, No Drawings

(56) References Cited

OTHER PUBLICATIONS

Ganoderma lucidum extract protects DNA from strand breakage caused by hydrowyl radical and UV irradiation (Kim K C et al, International Journal of Molecular Medicine, Spandidos Publications, GR, vol. 4, No. 3, Sep. 1, 1999, pp. 273-277).

In-Hye Ham, et al., "Study on the Variation of Components from Scrutellariae Radix by Processing and Storage Condition", Kor. J. Herbology, vol. 22, No. 2, (2007), pp. 189-199.

International Search Report for PCT/KR2008/006545, dated Jun. 9, 2009.

Permana et al, Antioxidative constituents of Hedyotis diffusa Willd, Natural Product Sciences (2003) vol. 9, No. 1, pp. 7-9.

Second Notification of Office Action w/English translation in KR 200880128875.2 dated Jul. 23, 2012.

Shan et al, "Effect of Polygonatum Odoratum Polysaccharide on Anti-Oxidation System and Immunological Function of Senile Mice", Chinese Journal of Clinical Rehabilitation [J], 2006, 10(11):135-137 (Mar. 20, 2006).

Sheu et al, A Comparative Study of Processed Scutellariae Radix. Chinese Pharmaceutical Journal, (1995) vol. 47, No. 3, pp. 243-251.

Sung-Hye Park et al., "A Study on the Application of Gastrodiae Rhizoma for Food Stuffs—Effects of Gastrodiae Rhizoma on the Regional Cerebral Blood Flow and Blood Pressure", J. East Asian Soc. Dietary Life, vol. 17, No. 4, (2007), pp. 554-562.

Thermal processing enhances anti-radical activity and reduces pro-oxidant activity in water-soluble fraction of selected allium vegetables (Roy Malay Kumar et al, Journal of the Science of Food and Agriculture, Wiley & Sons, Chichester, GB, vol. 87, No. 12, Sep. 1, 2007, pp. 2259-2256).

Written Opinion of the International Searching Authority for PCT/KR2008/006545, dated Jun. 9, 2009.

\* cited by examiner

MEDICINAL PLANTS EXTRACT USING PROCESSING OF HERBAL MEDICINE AND COMPOSITION OF SKIN EXTERNAL APPLICATION COMPRISING THE SAME

This application is a divisional of U.S. application Ser. No. 13/317,410, filed Oct. 18, 2011, which is a divisional of U.S. application Ser. No. 12/990,699 filed Nov. 2, 2010, which in turn is a U.S. national phase of International Application No. PCT/KR2008/006545, filed Nov. 6, 2008, which claims priority to KR Application No. 10-2008-0041544, filed May 2, 2008, the entire contents of each of which are hereby incorporated by reference.

TECHNICAL FIELD

The present invention relates to a medicinal plant extract prepared using Chinese herbal medicine processing and a cosmetic composition containing the same.

BACKGROUND ART

The processing of medicinal plants is a pharmaceutical technology of changing the inherent properties of herbal medicines by processing the herbal medicines based on Chinese medicinal theory. Any herbal medicine is toxic or intense in nature, and thus cannot be directly taken internally, any herbal medicine has medicinal properties which easily change, and thus cannot be stored for a long period of time, and any herbal medicine can be used only after impurities and some parts are removed. Even in the case of the same medicinal plant, the unprocessed material and the processed material have different properties or different actions. Such herbal medicines must be processed before use, and this operation is called the "processing" of herbal plants. The processing method is a traditional pharmaceutical technology and has various Korean names, including Hapwha, Hapyak, Suchi, Poja and Susa.

The objects of processing Chinese herbal medicines are to: (1) make medicine clean and facilitate the storage of medicine; (2) reduce or remove the toxicity or side effects of medicine; (3) change the nature of medicine to make the medicines more effective; (4) enhance the therapeutic effects of medicine; and (5) remove the offensive odor and taste of medicine to make it better to take the medicine.

The processing of herbal medicine is performed in various manners, and specific examples of the processing method are as follows:

(1) Roasting: this is a method of roasting herbal medicine, and the roasting temperature and time and the degree of roasting are important. In the roasting operation, heating power must be maintained at a uniform level, and continuous agitation is required for uniform heating.

1) Roasting without adding auxiliary material: this is a method of roasting herbal medicine with weak fire or strong fire to a prescribed degree.

(i) Roasting to yellow color: herbal medicine is placed in a vessel and roasted with weak fire to a prescribed degree.

(ii) Roasting to brown color: herbal medicine is placed in a vessel and roasted with weak fire, until the outer surface of the medicine becomes brown. The medicine is roasted either until the color of the section is turned dark or to a prescribed degree. Herbal medicine which is easily burned in the roasting process is wet with a small amount of clear water and roasted again or dried in sunlight.

(iii) Roasting to black or brown color: herbal medicine is placed in a vessel and roasted with weak fire to a prescribed degree, until the surface is burned black or the inner part is burned yellow. The roasted material is wetted with clear water, and then dried.

2) Roasting together with auxiliary material: this is a method in which a solid auxiliary material is placed in a vessel and a heated to a prescribed degree, and then herbal medicine is added thereto and roasted, and then the auxiliary material is filtered out.

(i) Roasting to yellow color or dark color: wheat bran is placed in a previously warmed vessel and heated until it smokes. Then, herbal medicine is placed in the vessel and agitated uniformly, and it is roasted until the color of the outer surface becomes yellow or dark. Then, the wheat bran is discarded, and the roasted material is cooled. Generally, 5-10 kg of wheat bran is used for 100 kg of herbal medicine.

(2) Baking: this is a method of roasting herbal medicine together with a specific amount of liquid auxiliary material to impregnate the auxiliary material into the tissue of the medicine.

(i) Baking together with alcohol: about 15% alcohol is generally used, and when Soju is used, the concentration of ethanol must be adjusted before processing of herbal medicine. Herbal medicine is added to alcohol, roasted in a vessel with weak fire to a prescribed degree, and then cooled. Generally, 10-15 kg of alcohol is used for 100 kg of herbal medicine.

(ii) Baking together with vinegar: vinegar is added to and uniformly mixed with herbal medicine, and the mixture roasted in a vessel to a prescribed degree and cooled. Generally, 10-15 kg of vinegar is used for 100 kg of herbal medicine.

(iii) Baking together with table salt: table salt is dissolved in a suitable amount of water, and then filtered. Herbal medicine is uniformly mixed or wetted with the salt water, placed in a vessel, roasted to a prescribed degree, and then cooled. Generally, 2 kg of table salt is used for 100 kg of herbal medicine.

(iv) Baking together with ginger: ginger is pounded, a suitable amount of water is added thereto, and the ginger solution is squeezed under pressure to obtain a juice. The juice is combined with a juice obtained by adding a suitable amount of water the ginger remnants and boiling the solution, thus preparing a ginger juice. When dry ginger is used, it is pounded in a mortar and boiled twice to make a juice. The ginger juice is added to herbal medicine, and the mixture is placed in a vessel and roasted with weak fire to a prescribed degree, until the ginger juice is completely absorbed into the herbal medicine. The roasted material is dried. Generally, 10 kg of ginger or 3 kg of dry ginger is used for 100 kg of herbal medicine.

(v) Baking together with honey: boiled honey is dissolved in a suitable amount of hot water, and then the honeyed water is sprinkled on or immersed in herbal medicine. The resulting herbal medicine is roasted with weak fire to a prescribed degree and cooled. Generally, 25-30 kg of honey is used for 100 kg of herbal medicine.

(3) Boiling: according to the processing regulation of each herbal medicine, a liquid auxiliary material is added to herbal medicine, and the mixture is boiled until the auxiliary liquid is completely absorbed or until the white color of the inner part of the cut herbal medicine disappears. The boiled material is dried. After toxic herbal medicine is boiled, the remaining juice must generally be discarded.

(4) Heating: according to the processing regulation of each herbal medicine, a liquid auxiliary material is placed in a suitable closed vessel, and herbal medicine is added thereto and heated in water bath or steamed with water vapor, until the auxiliary liquid is completely absorbed into the herbal medicine. The heated material is dried.

(5) Steaming: according to the processing regulation of each herbal medicine, a liquid auxiliary material was added or not added to herbal medicine, and the herbal medicine is steamed by heat in a suitable vessel or steamed to a prescribed degree. The steamed material is dried.

(6) Stirring: auxiliary materials such as clean sand, seashell powder and talc are used. Sand (or seashell powder or talc) is heated in a vessel, and herbal medicine is added thereto and stirred. When the stirred material is heated to a prescribed degree, it is taken out of the vessel and sieved to remove the sand, followed by cooling.

(7) Calcination: the degree of heating with fire is important, and an operation must be carried out such that herbal medicine is soft and easily smashed. Herbal medicine is cleaved into small lumps and heated in a fire pot which does not smoke or in a suitable vessel. When it is turned red, it is taken out of the vessel and cooled. Alternatively, immediately after it is heated red, it is immersed in a liquid auxiliary material, taken out of the material and dried. Then, the herbal material is either smashed or powdered with a mortar.

(8) Fermentation

Herbal medicine is fermented using fungi at a given temperature to change the inherent properties thereof, thus creating new therapeutic effects. Herbal medicine is naturally fermented in an environment having suitable temperature and humidity. In the fermentation process, the temperature and relative humidity are preferably 30-37° C. and 70-80%, respectively.

(9) Germination

This is a method of sprouting completely ripe fruits or seeds at a given temperature and humidity. In the method, fruits or seeds are immersed in water for about 6-12 hours and placed in a vessel which is well drained, and water is sprinkled on the fruits or seeds several times a day. Temperature and humidity are controlled with wet cloth. The temperature is maintained at 18-25° C., and the water content of the seeds or fruits is maintained at 40-45%. Alternatively, the humidity is maintained by sprinkling water every day. When the seeds or fruits are germinated and grow to about 0.6-1 cm, they are taken out and dried.

Although the above-described methods can be used alone, a suitable combination of the methods (e.g., a nine times steaming and nine times drying process) may also be used.

Meanwhile, it is known that reactive oxygen species which are produced by various physical, chemical and environmental factors, including enzyme systems, reduced metabolites, chemicals, pollutants and photochemical reactions, act as nonselective irreversible inhibitors against lipids, proteins, sugar and DNA, which are the structural components of cells, thus causing various diseases, including cell aging and cancer. Also, various peroxides, including lipid peroxides which are produced as a result of lipid peroxidation by these reactive oxygen species, cause oxidative damage to cells, leading to various functional disorders, thus causing various diseases.

Accordingly, antioxidants such as free radical scavengers or peroxide production inhibitors can be used as agents for inhibiting or treating aging and various diseases, which are caused by these oxides.

In addition, in order to develop natural antioxidants, many naturally occurring materials have been studied. Most naturally occurring materials have been used in the form of simple extracts, and it is unclear what compound of the extracts is attributable to the effects of the extracts. Also, the extracts are being used in cosmetic products and the like on the basis of experience and oral tradition.

DISCLOSURE

Technical Problem

Accordingly, the present inventors have conducted studies on existing medicinal plants after processing to solve the above-described problems and to find more excellent antioxidant materials and, as a result, have found that extracts of the processed medicinal plants have more excellent antioxidant effects, thereby completing the present invention.

It is, therefore, an object of the present invention to prepare a medicinal plant extract through the processing of herbal medicine and to provide a cosmetic composition which contains the extract as an active ingredient, and thus has an antioxidant effect.

Technical Solutions

An extract of a medicinal plant which is used in the present invention is prepared through Chinese herb processing, and a composition for skin external application which contains the extract as an active ingredient can provide an antioxidant effect.

The medicinal plant that is used in the present invention is at least one selected from the group consisting of The medicinal plant that is used in the present invention is at least one selected from the group consisting of *Terminalia chebula Retz* flesh, *Pueraria* root, *Angelica koreana*, *Chrysanthemum indicum*, *Rehmanniae radix*, *Rhus verniciflua Stokes*, licorice, dried ginger, *Pharbitidis semen*, *Cassiae semen*, *Meliae cortex*, *Angelica tenuissima*, *Sophora flavescens*, *Caragana chamlagu*, *Trichosanthes semen*, *Lycii fructus*, *Agastache rugosa*, *Selaginella involvens*, *Citrus* peel, *Lonicera japonica flower*, *Chrysanthemum zawadskii*, *Chrysanthemum indicum*, *Platycodon grandiflorum*, *Cudrania tricuspidata*, *Raphani semen*, *Arisaema amurense*, *Cervi cornus colla*, *Phaseolus aureus*, antler velvet, *Trapa japonica fruit*, *Brassica rapa*, *Angelica acutiloba*, *Citrus grandis osbeck*, *Circium japonicum*, *Glycine semen germinatum*, *Datura stramonium*, *Zizyphus jujuba*, Dae-cheong-chow, *Rheum undulatum*, *Persicae semen*, *Aralia continentalis Kitagawa*, *Cordyceps militaris*, *Eucommiae cortex*, *Ephedra sinica*, *Portulaca oleracea*, *Rhododendron brachycarpum*, *Codonopsis pilosulae radix*, malt, *Liriopis tuber*, *Chaenomeles Sinensis* fruit, *Akebiae caulis*, *Saussurea lappa*, Mui, *Moutan cortex radicis*, *Mentha arvevsis*, Bang-pung, *Pinellia ternata*, Chinese cabbage, Bak-gul-chae, *Pulsatilla Koreana* root, *Cynanchi radix*, *Bletilla striata* tuber, *Santalum album*, *Ampelopsis japonica* root, white *Poria cocos*, *Aconitum koreanum*, *Thujae orientalis semen*, *Hedyotis diffusa*, *Paeonia japonica*, *Angelica dahurica* root, *Atractylodes macrocephala* rhizome, *Rubus coreanus* fruit, *Poria cocos*, *Arecae pericarpium*, *Aconiti radix*, *Allium tuberosum*, *Ostericum sieboldii*, borneol, Sa-kwa-rak, *Adenophorae radix*, wild *ginseng* radix, *Crataegus pinnatifida* fruit, *Cornus officianalis* fruit, *Dioscorea rhizoma*, *Zizyphi spinosi semen*, *Gardenia fructus*, *Saururus chinensis*, *Atractylodes japonica Koidzumi*, Sang-gi-saeng, *Mori cortex radicis*, *Dichroa febrifuga*, *Morus alba* leaf, *Abrus precatorius*, ginger, *Rhizoma acori graminei*, *Agrimonia pilosa ledebour*, Seol-kyun-cho, *Asarum sieboldi*, *Perilla frutescens* var. *acuta*, *Pinus densiflora*, *Jasminum floridum* root, *Anethum graveolens*, *Euphorbia lathyris* seed, *Dipsacus asper*, *Tricholoma matsutake*, *Cimicifuga heracleifolia*,

*Bupleurum falcatum*, *Massa medicata fermentata*, *Artemisia* leaf, *Yakssuk*, *Lespedeza cuneata*, *Polygonum multiflorum* root, *Houttuynia cordata*, *Forsythia* fruit, *Nelumbinis semen*, *Nelumbo nucifera* seed, *Litchi chinensis*, *Papaver somniferum* flower, *Ganoderma lucidum*, *Aconitum carmichaeli*, *Acanthopanax sessiliflorus* bark, *Schizandra chinensis* fruit, *Chinensis Galla*, *Evodia officinalis*, *Linderae radix*, *Maydis stigmata*, *Polygonatum odoratum* root, *Orostachys japonicus*, *Solani nigri herba*, *Gentiana scabra* BUNGE, *Euphoria longana testa*, *Achyranthes japonica* root, *Polygalae radix*, *Genkwa flos*, *Oenothera odorata*, *Clematis mandshurica*, *Ulmi radicis cortex*, *Brassica campestris*, *Cistanche deserticola* stem, *Gypsophila oldhamiana* root, Eumn-yang-qwak, *Coicis semen*, Ik-mo-cho, *Alpinia oxyphylla* fruit, ginseng, In-jin, *Angelica acutiloba* root, *Securinega suffruticosa*, *Cnidium officinale*, *Aster* root, *Lithospermum erythrorhizon*, *Paeonia*, *Adenophora triphylla*, *Ailanthus altissima* bark, *Grifola umbellata*, *Poria cocos* red, *Polygonum multiflorum Thunberg*, red cabbage, *Paeoniae Radix Rubra*, *Anthriscus sylvestris*, *Sorbus commixta cortex*, *Syzygium aromaticum*, *Gleditsiae fructus*, *Gleditsiae spina*, *Lophatherum gracile*, *Cistanche deserticola*, *Phyllostachys nigra* sheath, *Lycium chinensis* root, *Hovenia dulcis* bark, *Anemarrhena asphodeloides*, *Kochiae fructus*, *Poncirus trifoliate* fruit, *Sanguisorba officinalis*, *Rehmannia glutinosa*, *Aconitum pseudolaeve Nakai*, Jin-O-ga-pi, *Phyllanthus urinaria*, *Citrus unshiu* peel, *Plantaginis semen*, *Xanthium strumarium* fruit, *Cnidii rhizoma*, *Gastrodia elata*, *Asparagus cochinchinensis*, *Zanthoxyli fructus*, *Semiaquilegia adoxoides*, *Opuntia humifusa*, *Dioscorea nipponica Makino*, *Saussurea involucrata*, *Trichosanthes kirilowii* root, *Artemisia apiaceae Herba*, *Amomi tsao-ko fructus*, *Aconiti ciliare tuber*, *Gardeniae fructus*, *Celosiae semen*, *Althaea rosea*, *Aquillaria agallocha*, Taek-ran, *Alisma canaliculatum*, *Ponciri fructus*, *Smilacis chinae radix*, *Cuscutae semen*, *Ligusticum rhizome*, *Tetrapanacis medulla*, *Morinda offcinalis How*, *Tiglii semen*, *Taraxaci Herba*, *Typhae pollen*, *Calypso bulbosa*, *Polygonum multiflorum* tuber, *Aeschynomene indica*, *Armeniacae semen*, *Helianthus annus* seed, *Cyperus rotundus*, *Elsholtzia ciliata*, *Cedrela sinensis* fruit, *Typha orientalis* pollen, *Scrophulariae radix*, *Geranium nepalense*, *Corydalis turtschaninovii*, *Schizonepeta tenuifolia*, *Sesamum indicum*, *Trigonella foenumgraecum*, *Cucurbita* spp, *Acanthopanax giraldii*, red ginseng, *Kombucha*, *Herba Trifolii pratensis*, *Carthamus tinctorius*, floral envelop, *Scutellaria baicalensis Georgi*, *Astragalus membranaceus*, *Coptis chinensis Franch*, *Polygonatum lasianthum radix*, *Lindera obtusiloba* branch, *Phellodendron amurense* bark, *Magnolia obovata*, black *Pharbitis semen*, and *Siegesbeckiae Herba*.

*Terminalia chebula Retz* flesh which is used in the present invention is a flesh obtained by removing seeds from the ripe fruit of *Terminalia chebula* Retzius and drying the remaining fruit and is used for the treatment of diarrhea, dysentery, proctocele and the like.

*Pueraria* root which is used in the present invention refers to the root of an arrowroot and is used to relieve fever, sweat, relieve thirst and treat headache, lumbago, neck-shoulder-back pain and the like.

*Angelica koreana* which is used in the present invention is a biennial or perennial plant belonging to the family Umbelliferae and grows to a height of more than 2 m. The leaves are divided, alternate and imparipinnate. Small and white flowers blooms at the end of the branches between August and September, and the fruit thereof is oval. The root similar to that of a balloon flower is used as analgesic and antipyretic agents.

*Chrysanthemum indicum* which is used in the present invention grows mainly in mountains and has short hairs throughout the grass. The stem grows to a height of 60-90 cm and is black in color and elongates. The flower is dried in October and added to alcoholic beverage, and the young leaves are used to prepare seasoned vegetables. The flower is also used for ornamental purposes, because it has a deep fragrance. In Chinese medicine, the plant is used for the treatment of fever, pneumonia, bronchitis, headache, gastritis, enteritis, a boil and the like.

Dried *Rehmannia radix* which is used in the present invention refers to the dried root of *Rehmannia glutinosa* and is used to alleviate fever, supplement blood and stop bleeding.

*Rhus verniciflua Stokes* which is used in the present invention is one obtained by collecting the sap of the lacquer tree and drying the collected sap and is used for menstrual disorders, extravasated blood, ascariasis and the like.

Licorice is a medicinal plant, and the root has a red-brown color and penetrates deeply into soil. The stem is angular and grows upright to a height of about 1 m. Because white hairs grow thick, the plant looks like light gray, and linear dots disperse. The flowers blooms between July and August, has a length of 1.4-2.5 cm and is purple in color, and the root has a sweet taste, and thus is used as a sweetening agent or a Chinese medicinal material.

Dried ginger which is used in the present invention is used for the treatment of stomach coldness, vomiting, diarrhea and the like.

*Pharbitidis semen* which is used in the present invention refers to the seed of a morning glory having a white or black color. The seed has a bitter taste and a cold nature and facilitates urination and defecation. It is used for the treatment of constipation, edema, Juk-Chui (abdominal mass), lumbago and the like.

*Cassiae semen* which is used in the present invention refers to the seed of *Cassia obtusifolia* which is an annual plant belonging to the family Leguminosae. The stem of the plant grows a height of about 1 m, and yellow flowers bloom in summer. The fruit of the plant forms a longish capsule bent like an arrow, and the seed in the capsule is *Cassiae semen*.

*Meliae cortex* which is used in the present invention refers to the root or bark of *Picrasma quassioides*. It is used as a vermicide or the like.

*Angelica tenuissima* which is used in the present invention is a perennial plant belonging to the family Umbelliferae, grows in the deep recesses of mountains and is distributed in various regions of Korea. It grows to a height of 30-80 cm, has no hair throughout thereof and emits fragrance. The plant bears oval fruits, and the root thereof is used for medicinal purposes. In Chinese medicine, the root gathered in the fall is used after drying to headache, arthralgia, dentalgia, abdominal pain, diarrhea, eczema and the like.

*Sophora flavescens* which is used in the present invention is a perennial plant belonging to the family Leguminoseae and grows to a height of 80-100 cm. In the plant, light-yellow, butterfly-shaped flowers bloom at the stem and branch end in racemes in summer. It bears narrow fruits, and the root is used for medicinal purposes. The root of *Sophora flavescens* is mainly used, and it has a bitter taste and a cold nature, and thus is used for the treatment of jaundice, malaria, discharging blood and the like.

*Caragana chamlagu* which is used in the present invention is a deciduous broad-leaved tree belonging to the family Leguminoseae, grows to a height of about 2 m and is thorny.

The leaves are alternate and imparipinnate, and butterfly-shaped yellowish red flowers individually appear at the leaf axil. The fruit of the plant is a cylindrical narrow fruit and is ripe in the fall. The plant is cultivated for ornamental purposes and distributed in Korea, China and the like.

*Trichosanthes semen* which is used in the present invention refers to the seed of a perennial climbing plant belonging to the family Cucurbitaceae. The plant grows to a height of 3-5 m, and the leaves are alternate and divided into a palm shape. Purple flowers blossom at the leaf axil between July and August, and the fruit has a ball shape and is ripe and golden. The seed is used to facilitate milk ejection, urination and defecation or to alleviate swellings.

*Lycii fructus* which is used in the present invention is the fruit of *Lycium chinense* and has an oval shape and a length of 1.5-2.5 cm. It is ripe and turns red from July and is harvested between July and November. It is used as antipyretic and analeptic agents.

*Agastache rugosa* which is used in the present invention is a perennial plant belonging to the family Lamiaceae, and the stem is 20-30 cm in height and is hairy throughout thereof. The leaf thereof is ovate and serrated. Lip-shaped light red flowers bloom in racemes between July and September. The plant grows in mountains and is distributed mainly in Jeju, Hamgyeongbuk-do and the like of Korea.

*Selaginella involvens* which is used in the present invention is a perennial plant belonging to the family Selaginellaceae, and the stem thereof is about 30 cm in height and has many branches. The leaf has a dark green color and is scaly. In a dry environment, the branch is revolute, and in a wet environment, the branch spreads. The plant is used for the treatment of menstrual irregularity, discharging blood and the like.

The *Citrus* peel which is used in the present invention refers to the peel of *Citrus unshiu*. It has a warm nature, and thus helps digestion and has medicinal effects on coughing, diarrhea, abdominal mass and the like.

The *Lonicera japonica* flower which is used in the present invention refers to the flower of *Lonicera japonica*, acts to lower fever and neutralize poison and is used for malignant swelling.

*Chrysanthemum zawadskii* which is used in the present invention is a perennial plant belonging to the family Compositae and grows to a height of about 50 cm. Red or white flowers appear at the end of the stalk between September and November, produce achenes and are added to alcohol drinks. The dried stalk and leaf of the plant are used, and in Chinese medicine and folk remedies, all parts of the plant including the flower are used for paralysis, women's' diseases, stomach troubles and the like.

*Chrysanthemum indicum* which is used in the present invention is a perennial plant belonging to the family Compositae and grows to a height of about 1 m. It bears flowers mainly in the fall, and the followers have various shapes and colors. It is classified into dae-guk (large flower), joong-guk (medium flower), and so-guk (small flower).

*Platycodon grandiflorum* which is used in the present invention is a perennial plant belonging to the family Campanulaceae and grows to a height of 40-100 cm. The leaves of the plant are alternate and oval in shape. The root is chubby, and the stalks emerge individually or in groups. White or sky-blue flowers bloom in July or August, and the fruit is a capsule type. The root is eaten or used as antitussives or expectorants.

*Cudrania tricuspidata* which is used in the present invention is a deciduous tree belonging to the family Moraceae and is thorny at the branch, and the shoot is haired. The leaves are alternate and sometimes divided into 3 leaflets. In May or June, the male flower blooms yellow, and the female flower blooms in the shape of a ball having a diameter of about 1 cm. Several fruits are clustered together like a large fruit and are ripe and turn red in September. The plant is known to be effective in treating tinnitus.

*Raphani semen* which is used in the present invention refers to the seed of *Raphanus sativus Linne* or other plants belonging to the family Cruciferae. It is used to cure a digestive upset or phlegm.

*Arisaema amurense* which is used in the present invention is a perennial plant belonging to the family Araceae and grows to a height of 30-60 cm, and the leaves thereof are divided into several leaflets and look like a bird's foot. In the plant, green flowers are borne in spadices between May and July, and the fruit is a red berry. The plant is used for the treatment of phlegm, cough, palsy, epilepsy and the like.

*Cervi cornus colla* which is used in the present invention is a glutinous drug prepared by boiling an antler. It has the effects of supplementing blood, stopping bleeding and stabilizing fetus and is used for lumbago, gonorrhea, leucorrhea and the like.

*Phaseolus aureus* which is used in the present invention grows well in loamy soil (black soil in which sand and clay are mixed at a suitable ratio) in a mild climate. It grows a height of 30-80 cm. It is used to treat skin diseases and acts to lower fever and neutralize poison.

The antler velvet which is used in the present invention is the soft antler of a deer and is used as a restorative for uplifting yang-qi and strengthening muscle and bone.

The *Trapa japonica* fruit which is used in the present invention is the fruit of *Trapa japonica* which is an annual plant belonging to the family Trapaceae. The root thereof is fixed in the mud, and the stem grows in water in an elongated form, comes out of water and has a feather-shaped base in water. The leaves are formed in a cluster at the top of the step, are triangular in shape, and float on water, because the petiole has protruded sacs containing air. In the plant, white flowers bloom in summer, and the fruit is an edible stone fruit. The plant grows in ponds or swamps and is distributed in Korea, Japan, China and others.

*Brassica rapa* which is used in the present invention is green-yellow vegetables belonging to the family Cruciferae, and is also called "vitamins" or "vitamin vegetables", because it is rich in vitamins. In the plant, the content of carotene next to the effect of vitamin A is two-times higher than in spinach. Thus, when 100 g of the plant is eaten, it provides 80% of the recommended daily value of vitamin A. In addition, the plant is also rich in iron and calcium.

*Angelica acutiloba* which is used in the present invention is the root of an *angelica* plant which is a perennial plant belonging to the family Umbelliferae. It mainly has anti-inflammatory and analgesic effects.

*Citrus grandis osbeck* which is used in the present invention is an evergreen short tree, reaches a height of 6 m and has thorns at the stem. The leaves are large in size and long oval in shape and have a length of 10-13 cm and a width of 4-5 cm. The leaf stalk has a length of 1-2.5 cm, and the leaf axil is large in size and has a width of 0.4-1 cm. The leaf has a serrate margin. The fruit is egg-shaped, has a length of 10-12 cm and a width of 9-10 cm and contains less than 6 chambers. The fruit generally weighs about 200 g, reaches a weight of 500 g in the case of large fruits, and has some irregularities on the surface.

*Circium japonicum* which is used in the present invention is a perennial plant belonging to the family Compositae. The stem is upright, grows to a height of 50-100 cm and has cobweb-like hair together with white hair. The flowers bloom between June and August and are purple to red in color. A head flower is formed at the branch and stalk end. The plant is used as a hemostatic agent.

*Glycine semen germinatum* which is used in the present invention refers to a material obtained by germinating *Glycine max* Merrill belonging to the family Leguminosae. It is used for diplegia caused by moisture in the summer season, limb trembling, bloated conditions caused by water retention, and difficult urination. It is also used to lower the fever caused by flu and to sweat.

*Datura stramonium* which is used in the present invention is an annual dicotyledonous plant belonging to the family Solanaceae of the order Tubiflorae. The stem is purple in color and spreads thick branches, and the leaf stalk is long and has a non-uniform serrate margin. The corolla is trumpet-shaped, light purple in shape and is surrounded by a tubular sepal. The end of the corolla is divided into 5 parts and has 5 stamens and 1 pistil. The fruit is a thorny capsule, and when it is ripe in October, it is divided into 4 parts to expose black seeds.

*Zizyphus jujuba* which is used in the present invention refers to a jujube fruit. The fruit has a red surface, is ovate and has a length of about 1.5-2.5 cm, and when it is ripe and turns red, it has a sweet taste. The fruit is eaten raw or dried after being harvested. The dried fruit is used in confectionery or for cooking or medicinal purposes. In Chinese medicine, the dried fruit is used as diuretic, tonic and palliative agents.

Dae-cheong-chow which is used in the present invention is the whole plant of *Hygrophila salicifolia* (Vahl) Nees. belonging to the family Acanthaceae and has a bitter taste and a cold nature. It is known to treat epidemic fevers and jaundice, reduce phlegm, stop coughing and treat hemoptysis (Dictionary of Chinese Materia Medica). It contains about 25 wt % of oil and a very small amount of alkaloid, calcium phosphate and calcium chloride.

*Rheum undulatum* which is used in the present invention is a perennial plant belonging to the family Polygonaceae, grows to a height of about 1 m and is hollow. The leaf has a length of 25-30 cm. The flower blooms between July and August, is used for medicinal purposes, has a cold nature and a bitter taste, and is used for difficult urination and defecation, talking in delirium, sleeptalking, extravasated blood, etc.

*Persicae semen* which is used in the present invention refers a semen (a relatively large granule) contained in the peach seed. It is obtained by gathering the seed of a peach when the peach is ripe in July or August, breaking the hard seed shell, and taking out the semen contained in the seed. It is used for medicinal purposes in order to treat coughing, constipation and extravasated blood.

*Aralia continentalis Kitagawa* which is used in the present invention refers to *aralia* shoots and grows in mountains. It is about 1.5 m in height and has hair at all the parts excluding the flower. The leaves are alternate and have a length of 50-100 cm and a width of 3-20 cm, and the young leaves of the plant have a soft brown color. Small leaves of the plant are egg-shaped or oval and serrated at the margin. The leaves have a green surface, and the backside of the plant is whitish. The leaves have small cotyledons at both sides below the leaf stalk. The plant is mainly used for muscular pain, headache, partial paralysis, etc.

*Cordyceps militaris* which is used in the present invention refers to a collection of mushrooms belonging to Clavicitipitaceae. It is present as an insect in the winter season and changes into a plant in summer. It is parasitic on the dead bodies of spiders, cicadas, butterflies, bees and the like to produce fruit bodies. It includes *Cordyceps militaris, Cordyceps sobolifera*, etc.

*Eucommiae cortex* which is used in the present invention is a deciduous tree belonging to the family Eucommiaceae and grows to a height of more than 10 m, and the leaves are alternate and ovate. In Chinese medicine, the cortex is used as a restorative and tonic and acts to strengthen the cerebral and cure lungs, knee pain and damping. In folk remedies, the boiled leaves are used for neuralgia and hypertension and also used as tea.

*Ephedra sinica* which is used in the present invention is an evergreen tree belonging to the family Ephedraceae of the order Ephedrales and grows in dry elevated areas or sandy soil. It grows to a height of 30-70 cm. The stem is upright and spreads many horsetail-like branches. It has many knobs, and a pair of scaly leaves are attached to each knob. The root is hard like a wood and is reddish brown. It functions as diaphoretic, antipyetic, antitussive and diuretic agents and is used for the treatment of fever and asthma.

*Portulaca oleracea* which is used in the present invention refers to a purslane and is used as feedstuff or medicine. It is soft, has a special smell, is viscous and has a salty taste and a cold nature. It has the effects of alleviating fever, neutralizing poison and stopping bleeding, and thus is used for bacterial dysentery, swellings, piles, cervical lymphadenitis, eczema, leucorrhea, uterine hemorrhage, difficult urination, etc. It was reported that the plant has an antimicrobial action, an action of increasing the peristalsis of intestinal tracts by increasing the uterine smooth muscle contractility, and a diuretic action.

*Rhododendron brachycarpum* which is used in the present invention is an evergreen tree belonging to the family Ericaceae of the order Ericales and grows in alpine regions. It grows to a height of 1-4 m. The tree bark is grayish white. The leaves are alternate, but 5-7 leaves are clustered at the end of the branch. The leaves are ovate or oval-lanceolate and leathery in texture. The leaves have a length of 8-20 cm and a width of 2-5 cm, and the leaf margin is plain and revolute. The surface of the leaf is dark green, and soft brown hair grows thick on the backside of the leaf. The leaves have a length of 1-3 cm. It is used as a diuretic and tonic.

*Codonopsis pilosulae radix* which is used in the present invention is a climbing perennial plant belonging to the family Campanulaceae of the order Campanulales and discharges juice when being cut. The root is similar to that of a balloon flower and has a length of about 30 cm. The leaves are alternate, but opposite at the short branch, egg-shaped or oval and have fine hairs on both sides, and the backside thereof is white. The leaves have a length of 1-5 cm and a width of 1-3.5 cm, and the leaf stalk has a length of 2-3 cm and is hairy.

The malt which is used in the present invention is a barley grain obtained by germinating unhulled barley under the action of moisture, heat and oxygen and is also frequently used to prepare a medium for culturing microorganisms. It contains saccharides, such as starch, and vitamins and is rich in amylase, and thus it is used as a nutritional supplement or a digestion aid (diastase, etc.) and sometimes used as feedstuff or a raw material for preparing maltose.

*Liriopis tuber* which is used in the present invention is a monocotyledon plant belonging to the family Lilaeaceae of the order Liliales and grows in shade. The leaves come out from a short and thick rhizome to form a cluster, and the root end becomes bigger like a peanut. The stem is upright and grows to a height of 20-50 cm. The leaves are dark green and linear and have a length of 30-50 cm and a width of 8-12 mm, and the lower portion thereof becomes a leaf sheath. The flowers bloom between May and June and are purple, and 3-5 flowers are attached to each knob in spikes. It is used as anti-inflammatory, tonic, antitussive, expectorant and cardiotonic agents.

The *Chaenomeles Sinensis* fruit which is used in the present invention is the fruit of *Chaenomeles Sinensis* and has a sour taste and a warm nature. It is used for a disturbance in muscular extension and contraction, beriberi, and vomiting and diarrhea.

*Akebiae caulis* which is used in the present invention is the stem of Akebia quinata Decaisne or other plants and is obtained by peeling the plant and cutting the peeled plant in a width direction. It is used for ascites caused by pyelonephritis, cystitis and urethritis, oral eruption, red urine, paralytic pain, etc.

*Saussurea lappa* which is used in the present invention is a perennial dicotyledonous plant belonging to the family Compositae of the order Campanulales, and the stem is upright and grows to a height of 0.8-2 m. Hair grows thick throughout the plant, and the plant is used for medicinal purposes. The leaves are alternate, oval or long oval in shape and serrated at the margin, and hair grows thick on the backside of the leaf. The flowers bloom between July and August, have a diameter of 5-10 cm and are yellow, and a head flower is attached to each leaf axil. It is used as diaphoretic, diuretic and expectorant agents and contains anthelmintic components.

Mui which is used in the present invention refers to the ripe dried fruit of *Ulmus macrocarpa* belonging to the family Ulmaceae and is also called "Mu-go", "Mui-in" or "U-mui" in Korean. It is used for enterohemorrhage, piles, malignant swellings, etc.

*Moutan cortex radicis* which is used in the present invention refers to the root cortex of *Paeonia suffruticosa* and is used for menstrual irregularity, menstrual cramps, a bruise, hemoptysis, nose bleeding, bone ache caused by ischemia, blood pressure elevation, extravasated blood, injuries, inflammation, swellings, initial appendicitis, etc., and eliminates breast discomfort. Also, it was reported that the plant has analgesic, sedative, antipyretic, anticonvulsant, anti-inflammatory, antithrombotic, anti-allergic, gastric juice secretion-inhibiting and uterine bleeding-inhibiting effects and antibacterial effects.

*Mentha arvevsis* which is used in the present invention is a perennial dicotyledonous plant belonging to the family Lamiaceae of the order Tubiflorales and is called "Park-ha", "Ya-sik-hyang", "Bun-ha-chae", "In-dan-chow" or "Ku-bak-ha" in Korean. It grows in moist fields to a height of 60-100 cm. The stem is rectangular in section and hairy on the surface. The leaves are alternate simple leaves with stalks and serrated at the margin.

Bang-pung which is used in the present invention is a medicinal material made using the root and rhizome of *Saposhnikovia divaricata Schiskin* belonging to the family Umbelliferae. It means preventing "pung" (paralysis) and is very important in treating paralysis. It is cylinder-shaped and the lower portion is slightly slender. The outer surface thereof is light brown in color, and the upper portion of the rhizome has dense vertical wrinkles. In some cases, a brown hairy leaf sheath is attached to the plant. It is effective against all kinds of paralysis-associated conditions, including headache, chill, fever, systemic pain, and throat pain.

*Pinellia ternata* which is used in the present invention is a perennial plant belonging to the family Araceae of the order Arales and grows in fields to a height of about 30 cm. Although the bulb is toxic, but in Chinese medicine, the plant has expectorant and antitussive effects, and thus is used for vomiting, diarrhea, and vomiting during pregnancy.

Chinese cabbage which is used in the present invention is a biennial plant belonging to the family Cruciferae of the order Papaverales. The outer leaf is inverted-egg shape, has a white vein at the center of the leaf and is green or light green. 100 g of Chinese cabbage contains 33 IU vitamin A, 100 IU carotene, 0.05 mg vitamin $B_1$, 0.05 mg vitamin $B_2$, 0.5 mg nicotinic acid, and 40 mg vitamin C. Vitamin A is deficient in the white portion and abundant in the green portion.

Bak-gul-chae which is used in the present invention refers to the above-ground portion of *Chelidonium majus Linne* belonging to the family Papaveraceae. Opposite leaves are attached to the stem having a number of branches, and the stem is hollow and light brown in color. The whole body of the plant discharges a dark-yellow liquid gel. It was reported to the plant has an anticonvulsant effect, the effect of promoting the peristalsis of intestinal tracts and the secretion of saliva, an anti-tumor effect, an anti-hepatitis effect and an antibacterial effect.

The *Pulsatilla Koreana* root which is used in the present invention refers to the root of *Pulsatilla koreana Nakai* or others belonging to the family Ranunculoideae. The root is cylindrical in shape, and the outer surface is yellowish brown or brown and has irregular vertical wrinkles. The epidermis is easily detached to expose a yellow xylem, and there is a net-shaped pattern. The root crown is covered with white soft hair and has the stem and leaf positions. The root is hard and crumbly, and thus easily broken, and the broken surface is smooth. It is used for dysentery caused by moist heat, amoebic dysentery, cervical lymphadenitis, and bleeding caused by piles.

*Cynanchi radix* which is used in the present invention refers to the root of *Cynanchum atratum Bunge* or other plants belonging to the family Asclepiadaceae. In the plant, light-yellowish elongate roots are clustered at short rhizomes to form a bridle shape and are brittle, and the broken surface is white in color. The cortex is distinguished from the xylem. The root is used to lower the fever of blood to treat conditions in which a slight fever at the late state of fever disease or after childbirth is not removed due to the exhaustion of Qi-vessel and in which the body is languid. In addition, the root is used to treat a cough caused by fever and pulmonary fever, difficult urination, swellings, malignant boils, sore throat, and snake bites.

The *Bletilla striata* tuber which is used in the present invention is a medicinal material obtained by drying the tuber of *Bletilla striata* belonging to the family Orchidaceae. It is a hemostatic agent which is used for blood spitting caused by pulmonary fever and blood vomiting caused by gastric fever, and it is applied to an external wound in a powdered state. It is used for surgical diseases such as boils and acts to granulate. It was reported that the tuber has various pharmacological effects, including stopping local bleeding, treating stomach and duodenum, inhibiting bacteria and increasing blood pressure, as well as anticancer activity.

*Santalum album* which is used in the present invention is an evergreen broad-leaved tree belonging to the family Santalaceae, grows to a height of 6-10 m and is blue green in color and glossy. The leaves are opposite and egg-shaped. The inside of the tree is yellowish, emits a sweet fragrance and is used in incense burners, drugs, handiworks, etc.

The *Ampelopsis japonica* root which is used in the present invention refers to the root of *Ampelopsis japonica*. It is used to treat poison and a burn.

White *Poria cocos* which is used in the present invention refers to the dried sclerotium of *Poria cocos*. It grows on places from pine trees have been cut out, and it is also cultivated. It is parasitic on the root of red pine trees, has a sweet and stale taste and a mild nature. Also, it acts as a supplement and has a diuretic effect which is not strong. It has been used as a tonic, acts in the lung, spleen, heart, nerve and bladder meridians to protect the spleen, alleviates phlegm and stabilizes the spirit. According to the results of pharmacological experiments, it was found that the white *Poria cocos* has a diuretic effect, a blood glucose lowering effect, a sedative effect and an immunity activating effect.

*Aconitum koreanum* which is used in the present invention grows in grass fields or forests. The root is strongly poisonous, but in Chinese medicine, it is used as antispasmodic and analgesic agents.

*Thujae orientalis* semen which is used in the present invention refers to the seed of the *Thujae orientalis* fruit. It acts to stabilize the body and sprit and lubricate the intestines, and thus is used for palpitation, perspiration, constipation, etc.

*Hedyotis diffusa* which is used in the present invention refers to the whole plant of *Oldenlandia diffusa (Willd.) Roxburgh* belonging to the family Rubiaceae. In the plant, white flowers resembling the lingua of snakes bloom. It is an annual plant and called "Baeg-wha-sa-seol-cho" or "Baeg-un-pul" in Korean, because it was collected for the first time in Baegun Mountain, Jeollanam-do, Korea. It grows wild mainly in southern regions and Jeju-do, Korea. It is used for a cough caused by pulmonary fever, tonsillitis and a sore throat. In addition, it is also used for appendicitis, pelvic inflammatory disease, icteric hepatitis and dysentery and acts to treat boils and neutralize snake venom.

*Paeonia japonica* which is used in the present invention is a perennial plant belonging to the family Ranunculaceae. It grows in the deep recess of mountains and grows to a height of 45-50 cm. The root is used as analgesic and antispasmodic agents and for women's diseases.

The *Angelica dahurica* root which is used in the present invention refers to the root of *Angelica dahurica*. It is used for a headache or lumbago caused by flu, paranasal sinitis and the like. It is also used to treat boils.

The *Atractylodes macrocephala* rhizome which is used in the present invention is a medicinal material obtained by removing the rhizome or integument of *Atractylodes macrocephala* and drying the removed rhizome or integument. It has a special odor, is slightly bitter and sweet in taste, is viscous when being chewed, and has a warm nature. It is used for light eating caused by a weak stomach, languor, facial yellowing, discharge of loose feces, and diarrhea. In addition, it facilitates water excretion when the whole body is swelled and digestion is difficult due to water retention. Also, it is used for coughing and clear phlegm, a flu involving gastrointestinal disorders, and limb pain.

The *Rubus coreanus* fruit which is used in the present invention is the unripe fruit of *Rubus coreanus* belonging to the family Rosaceae. It is odorless and has a sour and sweet taste and a warm nature. It enhances the renal function and is used for involuntary emission of semen and a wet dream. Also, it is used for reduced visual acuity and makes the hair black. Furthermore, it also makes the skin smooth and beautiful. It was reported that the fruit has anti-inflammatory, antioxidant and anti-*Helicobacter pylori* effects.

*Poria cocos* which is used in the present invention is a mushroom belonging to the family Polyporaceae, the order Aphyllophorales, the class Basidiomycetes, and is parasitic on the root of trees such as pine trees in soil. It has a sclerotium size of 10-30 cm and is round-shaped, longish or mass-shaped. The surface is reddish-brown, light brown or dark brown in color and is generally rough, and in some cases, the root bark is broken. The fresh is white and gradually turns rose pink. It is classified, according to color, into white *Poria cocos* and red *Poria cocos*. Also, a portion part of *Poria cocos* that the pine tree root penetrates is called "Bok-sin" in Korean. It has tonic, diuretic and sedative effects and I used for renal disease, cystitis and urethritis.

*Arecae pericarpium* which is used in the present invention refers to the peel of the ripe fruit of *Areca catechu* L. belonging to the family Arceaceae and is distributed in Korea, China, Japan and others. It has an hollow pyramidal shape or a shape obtained by cutting a long oval body in a vertical direction. The outer surface is yellowish brown in color, has vertical wrinkles and is covered with a thin fiber layer. The inner surface is brown or dark brown in color and glossy and has vertical fine wrinkles. The cut surface is fibrous, and the cross-section is light yellowish brown in color. When viewed with a magnifying glass, the fiber group is shown as a light brown or dark brown point. It has other Korean names, including "Jeo-bin-rang", "Bin-rang-pi", "Bin-rang-gak", "Bok-mo", "Dae-bok-yung", and "Dae-bok-bin-rang", "Dae-bok-mo".

*Aconiti radix* which is used in the present invention refers to the tuber root of *Aconitum japonicum* belonging to the family Ranunculaceae and is also called "*Aconiti* tuber". In Chinese medicine, it is not used alone and is used in combination with *Cinnamomum cassia, Poria cocos* or licorice root as stimulant, cardiotonic, analgesic and diuretic agents. It is used to alleviate a cold sweat, a chill, paralysis, pain, neuralgia and rheumatoid arthritis, in addition to restore an extremely reduced metabolic function.

*Allium tuberosum* which is used in the present invention is a perennial plant belonging to the family Lilaeaceae. The bulb has a short rhizome at the lower portion and a blackish yellow fiber at the outside. The bulb is used to make the stomach strong and treat a burn, and a soft portion is used for eating purposes. The seed is called *Allii tuberosi semen* and used for urination in Chinese medicine.

*Ostericum sieboldii* which is used in the present invention grows in a grass field to a height of 40-70 cm. The plant contains saponin and fatty oil in the root, and thus is used to an antipyretic, analgesic or tonic and as a medicinal material for respiratory, digestive and cardiovascular diseases.

Borneol which is used in the present invention refers to a crystal obtained from borneo camphor. It is aromatic and is used to treat paralysis, congestion, a confused mind caused by fever, or a sour throat.

Sa-kwa-rak which is used in the present invention refers to the reticular fiber and vascular bindle of the fruit of *Luffa cylindrica Roemer* belonging to the family Cucurbitaceae. When the plant is ripe, the flesh becomes fibrous. The medicinal material is long cylindrical or long rhombic in shape, slightly bent, and relatively slender at both ends. The outer surface is white or yellowish white in color, and several layers of reticular fiber are entangled to form a net-like structure. The medicinal drug is lightweight, has a hard texture and is not easily broken off. The cut side has 3 ovaries having three large cavities in which some black seeds may remain. It is also called "Man-kwa" in Korean. It was reported that the medicinal material has the effects of inhibiting edema in arthritis, inhibiting inflammation in erythema, relieving pain and inhibiting skin bacterial infection.

*Adenophorae radix* ("Sa-sam") which is used in the present invention refers to the root of *Adenophora triphylla* var. *japonica* Hara or other plants belonging to the family Lilaeaceae and is known as one of five ginsengs along with "In-sam" (*ginseng*), "Hyun-sam", "Dan-sam" and "Ko-sam", because they are used for similar therapeutic proposes, even though they are processed in different ways. The "Sa-sam" was named because it is white in color and grows well in sandy soil. It is pyramidal or long conical in shape and bent, and has branched roots in some cases. The upper portion has a rhizome having vertical wrinkles. The root is lightweight and is likely to break off, and the broken surface is milky and has many pores. It was reported to have various pharmacological effects, including expectorant, antibacterial, hemolytic and cardiotonic effects.

Wild *ginseng* which is used in the present invention is a kind of *ginseng* growing naturally in the deep recesses of mountains. It is sweet and slightly bitter in taste and has a slightly warm nature. It enters the spleen and ling meridians to strengthen vigor.

*Crataegus pinnatifida* fruit which is used in the present invention is a medicinal material obtained by drying the ripe fruit of *Crataegus pinnatifida* Bunge var. *typica* Schneider belonging to the family Rosaceae. The fruit has an apple taste and is red as in the case of a small apple. It has a shape similar to that of a red jujube fruit. It was reported to have a cardiotonic effect, a blood circulation improving effect and a blood pressure lowering effect.

The *Cornus officianalis* fruit which is used in the present invention is the fruit of *Cornus officianalis*. The fruit is separated into a fresh and a seed, and the separated fresh is used as a raw material for preparing alcoholic drinks, tea and a Chinese medicine. In Chinese medicine, the fresh is used for headache, tinnitus and a lung trouble and as an antipyretic, and in folk remedies, it is used for a cold sweat and enuresis.

*Dioscorea rhizoma* which is used in the present invention is the tuber root of *Disocorea japonica* or *Disocorea batatas* belonging to the family Disocoreaceae. It is obtained by gathering the root between the 18th of the 24 seasonal divisions and the winder solstice and drying the collected root. The outer surface is white or yellowish brown in color, and the inside consists of a powdered tissue or a gelatinized horny tissue.

*Zizyphi spinosi semen* which is used in the present invention is the seed of *Zizyphi spinosi*. It is used for hypersensitivity, insomnia, forgetfulness, a cold sweat and the like and has the effects of strengthening a stomach and inhibiting anemia. It was reported that the medicinal material has various pharmacological effects, including sedative, sleeping, blood pressure-lowering, analgesic, antioxidant, immunity boosting and uterus exciting effects.

*Gardenia* fruit which is used in the present invention is the fruit of *Gardenia jasminoides* and is used as antipyretic, hemostatic and diuretic agents.

*Saururus chinensis* which is used in the present invention is a perennial dicotyledonous plant belonging to the family Saururaceae of the order Piperales and grows in damp ground. The rhizome is white and spreads sideways in mud. The stem is 50-100 cm in height. The leaves are alternate, egg-shaped, 5-15 cm long, sharp at the end, heart-shaped at the base, has 5-7 veins and are plain at the margin. The leaf surface is green, and the backside of the leaf is light white, but 2-3 leaves at the top of the stem have a white surface. The leaf stalk is 1-5 cm in length and has a broad base covering the stem. The plant is used when the body is swelled and the urine is not easily discharged. In addition, it is also used for beriberi, jaundice, hepatitis and the like.

*Atractylodes japonica Koidzumi* which is used in the present invention is a perennial dicotyledonous plant belonging to the family Compositae of the order Campanulales. The rhizome is thick, long, knotty and fragrant. The stem is upright, branched into several parts at the top and grows to a height of 30-100 cm. The leaves sprouting from the root are dried out when the flowers bloom. The leaves attached to the stem are alternate, the leaves attached to the base of the stem are divided into pieces, and the divided pieces are 3-5 in number, egg-shaped or inverted-egg shaped, glossy at the surface, white at the backside and serrated at the margin and have leaf stalks having a length of 3-8 cm. The leaves attached to the top of the stem are not divided and have no leaf stalk. The rhizome is used as a medicinal material called "chang-chool". It has diuretic and analgesic and stomach-strengthening effects, and thus is used for inappetence, indigestion, gastritis, flu and the like.

Sang-gi-saeng which is used in the present invention is a medicinal material obtained by drying the leaf, stem and branch of *Loranthus parasticus* Merr. or *Viscum album* L. var. *coloratura* Ohwi belonging to the family Loranthaceae. It is has a blood pressure-lowering effect, and thus is used for dizziness caused by hypertension. In addition, it strengthens the liver and the kidneys to strengthen bone and muscle and is used to treat the instability of fetal movement.

*Mori cortex radicis* which is used in the present invention refers to the rhizome of *Morus alba* and similar plants. It is used to treat a cough caused by pulmonary fever, and asthma, and has a diuretic effect. It is used to treat acute pyelonephritis and edema, has a blood pressure lowering effect and is also used for nasal hemorrhage and blood spitting. In addition, it is also used to treat epidemic hepatitis. It was reported to have various pharmacological effects, including antitussive, diuretic, blood pressure-lowering, sedative, analgesic, antipyretic, antispasmodic and antimicrobial effects.

*Dichroa febrifuga* which is used in the present invention is a dicotyledonous deciduous shrub belonging to the family Rutaceae of the order Geraniales and grows in mountainous districts. It grows to a height of 1.5-3 m, and the bark is grayish brown in color, and young branches are slightly hairy. The leaves are alternate, 5-13 cm long, ovate or inverted-egg shaped, sharp at the end and smooth or serrated at the margin. The leaf surface is yellowish green and glossy and has a unique smell and a short stalk. The root is used as a medicinal material called "chi-shin-yang" to treat the cough, fever and sour throat caused by flu and has effects on arthritis, dysentery, swellings and malaria.

The *Morus alba* leaf which is used in the present invention is the dried leaf of *Morus alba* L. or other plants belonging to the family Moraceae, and the young leaf of the plant is also called "sang-ji" in Korean. *Morus alba* (mulberry) which is eaten by silkworms has excellent effects, like a tree sacred to the gods. The *Morus alba* leaf is used to treat fever, headache, eyeball hyperemia, cough, thirst, skin hives and the like.

*precatorius* which is used in the present invention is called "Sang-sa-ja" or "Hong-doo" in Korean. It is used as arrow poison, because the shell contains highly toxic abrin. The leaf contains glycyrrhizin and is sweet like licorice, and thus is used to prepare beverages.

The rhizome of ginger which is used in the present invention is dried, crushed and used as spice in bread, confectionery, curry, sources and pickle. Also, after the rhizome is peeled and boiled, it is preserved in syrup and used to prepare ginger tea and ginger alcoholic beverages. In Chinese medicine, the dried rhizome has effects on indigestion, vomiting and diarrhea, promotes blood circulation and has anti-inflammatory and analgesic effects.

*Rhizoma acori graminei* which is used in the present invention is a perennial dicotyledonous plant belonging to the family Araceae of the order Arales and grows in mountainous districts or a riverside of a field. The rhizome spreads sideways, and the fibrous roots sprout from the knobs. The distance between the knobs in soil is long, but the aboveground part has a short distance between the knobs and is green in color. The leaves sprout from the rhizome in a cluster, is 30-50 cm long, stripe-shaped, has no vein and is sharp at the end. The base of the outer leaf surrounds the base of the inner leaf, and the leaves are alternately arranged in two rows. The rhizome is used as analgesic, sedative and stomachic agents, and in folk remedies, is also added to a bath.

*Agrimonia pilosa ledebour* which is used in the present invention is a perennial plant belonging to the family Rosaceae. In Chinese medicine, the whole plant is dried between the summer and the fall but before flowering and is used as hemorrhage and convergent agents and to treat uterine bleeding, poison, blood vomiting, urine bleeding, carbuncle, cancer, etc.

Seol-kyun-cho which is used in the present invention is the root of *Salvia plebeian* R.Br. belonging to the family Labiatae. It is bitter and hot in taste. It has the effect of alleviating swellings and is known to be effective in treating blood vomiting, nasal bleeding, a bruise, poison, etc.

Se-shin which is used in the present invention is a medicinal material obtained by drying the root of *Asarum sieboldii* which is a perennial plant belonging to the family Aristolochiaceae. The root is gathered between the spring and the summer, washed clean with water and dried in shade. The dried root is used for headache, nasal stuffing, fever, phlegm and breathlessness, which result from flu. It is used to treat laryngitis, nasitis and bronchitis.

*Perilla frutescens* var. *acuta* which is used in the present invention is an annual plant belonging to the family Lamiaceae. It grows to a height of 30-100 cm, and the leaves are opposite, egg-shaped and serrated at the margin. Between August and September, light purple flowers bloom at the leaf axil or stem end, and the fruit is a round achene. The leaf and stem are used for medicinal purposes, and the young leaf and seed are used for eating purposes. The plant is also called "So-yup", "Cha-zo-gi" or "Cha-ze-gi" in Korean, and the seed is called "So-ja" in Korean.

*Pinus densiflora* which is used in the present invention is an evergreen conifer tree belonging to the family Pinaceae. The leaves are used for beriberi and indigestion and as a tonic, and the flowers are used for dysentery. The rosin is used as a raw material for preparing a plaster.

*Jasminum floridum* root which is used in the present invention refers to the root of *Jasminum floridum* Bge. belonging to the family Oleaceae and is used to treat wounds.

*Anethum graveolens* which is used in the present invention is an annual plant belonging to the family Umbelliferae. Because all parts of the plant emit a unique fragrance, the flower, leaf, stem and seed of the plant are used for medicinal purposes. The seed has excellent digestive, carminative, sedative and sleeping effects and is effective in removing foul breath and preventing arteriosclerosis. The use of the seed as a pillow enables a person to sleep well.

*Euphorbia lathyris* seed which is used in the present invention is the seed of the medicinal plant *Euphorbia lathyris*. The residue remaining after removing oil from the seed is used as diuretic and laxative agents and to treat edema, ascites and food poisoning. The seed is highly toxic, and thus requires care in use.

*Dipsacus asper* which is used in the present invention is a perennial dicotyledonous plant belonging to the family Labiatae of the order Tubkflorales and grows in mountainous districts. The stem is upright and about 1-m high and has fine hair throughout thereof, and about 5 pyramidal thick tuber roots sprout from the stem. The leaves are attached opposite to each other, have long stalks and are heart-shaped or egg-shaped. The leaves are regularly serrated at the margin and have fine hair at the backside. The thick root is used to treat a cut and women's diseases.

*Tricholoma matsutake* is a typical edible mushroom belonging to the family Tricholomataceae, grows on soil in a pine-grove and has a unique fragrance and a good taste. Generally, *Tricholoma matsutake* occurs on 20-60-years old pine-groves and is a symbiotic fungus forming mycorrhiza in a state attached to the rootlets of a pine.

*Cimicifuga heracleifolia* which is used in the present invention is a perennial plant belonging to the family Ranunculaceae. In Chinese medicine, the root of the plant is used as antipyretic and antidote agents. It was reported that, when the seed is used to lower a fever caused by flu, the fever is lowered while sweating.

*Bupleurum falcatum* which is used in the present invention is a perennial dicotyledonous plant belonging to the family Umbelliferae of the order Umbellales. The root contains saponin, fatty oil and the like, and in Chinese, it is used as antipyretic, analgesic and tonic agents or to treat respiratory, digestive and cardiovascular diseases.

*Massa medicata fermentata* which is used in the present invention is called "Yuk-sin-kok" in Korean and refers to a material prepared by mixing 6 kinds of medicinal materials. It improves the function of respiratory organs, facilitates digestion and acts to make the stomach easy. It is effectively used when a person suffers from indigestion, when a person feels heavy in the chest, when vomiting and diarrhea occur and when a person has a stomachache. The results of pharmacological experiments revealed that the plant has the effect of strengthening the stomach.

*Artemisia* leaf which is used in the present invention refers to a medicinal material obtained by drying the leaf or young stem of *Artemisia argyi, Artemisia princeps* or *Artemisia mntana*. It makes Qi-blood and meridians warm, and thus is effective in retarding uterine bleeding occurring when the uterus and the abdominal region are cold and weak, bleeding during pregnancy, blood vomiting, nasal bleeding and blood spitting. Also, it is used for conditions in which the lower belly above the bladder is weak and cold and the abdomen is cold and has pain, and for menstrual irregularity and lecorrhea. In addition, it is effective in treating eczema and itching. It was reported that the plant has various pharmacological effects, including a hemostatic effect, an antibacterial effect, a bronchial smooth muscle-relaxing effect, an expectorant effect, a sleeping effect, a uterus excitation-inducting effect, and an anaphylatic shock-preventing effect.

Yakssuk which is used in the present invention refers to a wormwood required for performing moxibustion and a wormwood for medicinal purposes. In Chinese medicine, the leaf of wormwood is used as a medicinal material called "Ae-yeop" and acts to stop bleeding and inhibit the growth of bacteria and as an expectorant. Also, it is effective against menstrual pain, menstrual irregularity and leucorrhea. A solution obtained by boiling Yakssuk in water is used to wash the affected part of persons having eczema or itching.

*Lespedeza cuneata* which is used in the present invention is a dicotyledonous shrub belonging to the family Leguminosae of the order Rosales and is called "Ya-Kwwan-moon", "No-woo-keun", "Ho-ji-ja", "San-chae-ja" or "Bi-su-ri" in Korean. It is used for poor vigor, impotence, premature ejaculation, cough, pertusis, and snake bites. It was reported that the plant has various pharmacological effects, including an expectorant effect, an asthma-relieving effect, an effect on the uterus, an antibacterial effect, etc.

*Polygonum multiflorum* stem which is used in the present invention refers to the stem of *Polygonum multiflorum* which is a perennial climbing dicotyledonous plant belonging to the family Polygonaceae of the order Polygonales. It is effective as antitussive and expectorant agents and against arthritis.

*Houttuynia cordata* which is used in the present invention refers to the above-ground part of *Houttuynia cordata* belonging to the family Saururaceae. It has excellent antipyretic and wound-draining effects, and thus is used for a cough, bloody pus, pneumonia, acute and chronic bronchitis, enteritis, urinary tract infection, high fever, and difficult urination. It was reported that the plant has various pharmacological effects, including antibacterial, immunity-boosting, anti-inflammatory, diuretic and antitussive effects.

*Forsythia* fruit which is used in the present invention refers to the fruit of *Forsythia viridissima* or *Forsythia suspensa* belonging to the family Oleaceae. The fruit lowers fever and neutralizes poison, and thus is used to lower the fever of the heart in the initial stage of disease and used for high fever and numbness. Also, it is used for boils, red spots, typhlitis, lung abscess, lymphadenitis, a sore throat, etc., and has diuretic and anti-inflammatory effects. It was reported that the plant has various pharmacological effects, including antibacterial, anti-inflammatory, blood pressure-lowering, hemostatic, liver-treating, antipyretic effect, antiemetic and diuretic effects.

*Nelumbinis semen* which is used in the present invention refers to the fruit of a lotus flower. It is used for women's diseases.

*Nelumbo nucifera* seed which is used in the present invention is the seed of a lotus flower and refers to a medicinal material obtained by peeling the seed and drying the peeled seed. The dried seed has been widely used for a long period of time, because it has been known that it strengthens a stomach and raises sprit and vigor and that the internal use of the seed reduces the body weight, prevents aging, does not feel hungry and increases the length of life. It was reported that the dried seed has the effect of inhibiting nasal cancer and throat cancer.

*Litchi chinensis* which is used in the present invention is native to the southern part of China and is frequently cultivated as a fruit tree. The fruit is round and about 3-cm diameter, and the outer surface has protrusions and resembles the turtleback surface. The fruit flesh is sour and sweet, has a unique fragrance and is eaten raw. In the southern part of China, the fruit is known as the king of fruits.

*Papaver somniferum* flower which is used in the present invention refers to the flower of a poppy. In folk remedies, the fruit and plant separated from *Papaver somniferum* have been used for emergent diseases. When a person smokes opium together with tobacco, the person feels dimness, and when the person habitually smokes opium, poisoning with opium appears, leading to death in severe cases. The seed has a fat content of 45-50%, and thus is used for edible or industrial purposes. The seed contains no anesthetizing component.

*Ganoderma lucidum* which is used in the present invention is a semicircle-shaped, kidney-shaped or fan-shaped mushroom. In Chinese medicine, the mushroom is used for nervous breakdown, hypertension and various cancers, because it has tonic, antitussive and tumor-relieving effects. The mushroom is covered with a hard shell and glossy, as if it is vanished. Thus, it is valuably used as a Chinese medicinal material and also used for decorative purposes.

*Aconiti radix* which is used in the present invention refers to the tuber root of *Aconitum japonicum* belonging to the family Ranunculaceae and is also called "*Aconiti* tuber". In Chinese medicine, it is not used alone and is used in combination with *Cinnamomum cassia, Poria cocos* or licorice root as stimulant, cardiotonic, analgesic and diuretic agents. It is used to alleviate a cold sweat, a chill, paralysis, pain, neuralgia and rheumatoid arthritis, in addition to restoring an extremely reduced metabolic function.

*Acanthopanax sessiliflorus* bark which is used in the present invention refers to the bark of the root, stem and branch of *Acanthopanax sessiliflorus* or other plants belonging to the family Araliaceae. It enhances the energy of the liver and kidneys to strengthen muscle and bone. Thus, it is used for limb paralysis and convulsion, weak waist and knee, impotence of the lower limbs, a bone fracture, a bruise, edema, etc. It was reported that the bark has various pharmacological effects, including immunity-boosting, antioxidant, anti-fatigue, anti-fever, anti-stimulant, endocrine function-regulating, blood pressure-regulating, anti-radioactive and poison-neutralizing effects.

*Schizandra chinensis* fruit which is used in the present invention refers to the fruit of *Schizandra chinensis*. It has a diameter of about 1 cm and is dark red and ball-shaped. It contains red juice and 1-2 reddish brown seeds. It has five tastes, sweet, sour, bitter, salty and hot tastes, and among these tastes, the sour taste is the strongest. It contains shisandrin, gomisin, citral, malic acid, citric acid and the like, and thus is used to strengthen the heart, lower blood pressure and increase immunity and as a tonic. It acts to enhance lung functions and has antitussive and expectorant effects, and thus it is effective in treating a cough or thirst.

*Chinensis Galla* refers to an insect wax resulting from a process in which *Schlechtendalia chinensis* belonging to the family Aphididae of the order Homoptera is parasitic on the leaf of *Rhus javanica* belonging to the Anacardiaceae. It has an irregular bag shape and frequently resembles the human ear. It is hollow and very sour in taste. In Chinese medicine, it is used for the treatment of diarrhea, anal prolapse, gastric ulcer, duodenal ulcer, involuntary emission of semen, hema feces, haematuria, stomatitis, etc., because it has convergent, hemostatic and antibacterial effects. It has a tannin content of 50-60%, and thus is used as a raw material for preparing coloring agents or ink, in addition to tanning agents.

*Evodia officinalis* which is used in the present invention is a dicotyledonous deciduous tree belonging to the family Rutaceae of the order Geraniales. In Chinese medicine, a material obtained by gathering the unripe fruit of *Evodia officinalis* in September and drying the gathered fruit is used as stomachic, anthelmintic, antidotal and diuretic agents.

*Linderae radix* which is used in the present invention is the dried tuber root of *Lindera strichnifolia*. It promotes Qi circulation, eliminates cold effects and makes the bladder and kidneys warm, and thus is used for the treatment of cardio-abdominal pain, beriberi, urinary incontinence and the like.

*Maydis stigmata* which is used in the present invention refers to corn silk in Chinese medicine. It is used for adult diseases, including diabetes, hypertension and hypercholesterolemia, difficult urination, acute gastritis, nephritis, edema in pregnant women, inflammation, fever, hemorrhage, a calculus, pleurisy, ascites, cystitis, urethritis, jaundice, hepatitis, cholecystitis, cholangitis, cirrhosis, arthritis, etc.

*Polygonatum odoratum* root which is used in the present invention refers to the dried root of *Polygonatum odoratum* and has the effects of clearing away fever and improving female vigor (Yin-Qi).

*Orostachys japonicus* which is used in the present invention is a perennial dicotyledonous plant belonging to the family Crassulaceae of the order Rosales and grows on or around rocks in mountains. The whole plant is medicinally used as a tonic, and the squeezed juice is used for insect bits or burns. It has an anticancer effect, is used as antipyretic and hemostatic agents and is effective in treating hepatitis, eczema, dysentery, malignant tumors, and burns

*Solani nigri herba* which is used in the present invention is an annual dicotyledonous plant belonging to the family Solanaceae of the order Tubkflorales. In Chinese medicine, the medicinal material is obtained by collecting and drying the whole plant between the summer and the fall and is used to treat flu, chronic bronchitis, nepthritis, jaundice, boils, cancer, etc. In folk remedies, the pulverized raw plant is applied to wound sites, or the boiled raw plant is used to wash affected parts.

*Gentiana scabra BUNGE* which is used in the present invention is a perennial plant belonging to the family Gentianaceae. It is used for the treatment of jaundice caused by the damp heat of the liver and gall, dysentery, itching of the secret parts, leucorrhea, eczema, limb convulsions caused by high heat, cheek pain, headache, eye hyperemia, hard hearing, etc. It was reported that the plant has various pharmacological effects, including the effects of protecting liver functions, promoting bile secretion and inhibiting *Pseudomonas aeruginosa*, modified bacteria, *Diplococci*, *Staphylococcus aureus*, etc.

*Euphoria longana* testa which is used in the present invention refers the testa of *Euphoria longana* belonging to the family Sapindaceae. It has a soft texture, is viscous and has a sweet taste and a unique fragrance, and thus is also used as an accompaniment to a drink. Furthermore, it is used for irregular heart beating caused by too much thinking, forgetfulness, insomnia, indigestion, and discharge of loose feces. In addition, it is used for convalescent weakness, weariness, uncontrollable sweating, stagnation of Qi and blood after childbirth, and edema. The pharmacological effects of the plant include a fungal dermatitis inhibitory effect, a tonic effect, an antioxidant effect, an immunity-activating effect, etc.

*Achyranthes japonica* root which is used in the present invention refers the root of *Achyranthes japonica* Nakai belonging to the family Amaranthaceae. It is substantially odorless and is viscous. It is slightly sour in taste and has a mild taste. When it is used raw, it eliminates extravasated blood and boils, and when it is used after boiling, it strengthens the liver and kidneys to strengthen muscle and bone. Because it eliminates extravasated blood, it is used for menstrual irregularity and abdominal pain after childbirth, supplements marrow, and promotes Yin-Qi circulation to alleviate arthritis and treat the mouth and tongue rash caused by the deficiency of Yin-Qi. In addition, it was reported that the plant has various pharmacological effects, including a uterus exciting effect, a cholesterol-lowering effect, a diuretic effect, a blood glucose-lowering effect, and a liver function-improving effect.

*Polygalae radix* which is used in the present invention refers to the root of *Polygala tenuifolia* which is a perennial dicotyledonous plant belonging to the family Polygalatenuifolia of the order Geraniales. In Chinese medicine, it is used as expectorant, tonic and aphrodisiac.

*Genkwa flos* which is used in the present invention refers to the bud of *Daphne genkwa* belonging to the family Thymelaeaceae and is called "Geo-soo" or Doo-tong-hwa" in Korean. It is used to treat asthma and a cough, allows the water in the side to come down, and treat dropsy. In addition, it is used to treat abdominal distension, boils, head eruption, difficult urination, constipation, etc. It was reported that the plant has the pharmacological effects of promoting urination, inhibiting the movement of the intestinal tract and uterine and killing insects.

*Oenothera odorata* which is used in the present invention refers to an evening primrose. The root is used as a medicinal material, and for some diseases, the leaf is also used. In folk remedies, the seed oil is also used for diabetes. The root has antipyretic and anti-inflammatory effects and is effective in treating flu, a sour throat, bronchitis and dermatitis. The seed oil is effective against diabetes, hypertension and obesity, and it inhibits the excessive accumulation of lipids, including cholesterol, and thus is used for hyperlipidemia.

*Clematis mandshurica* root which is used in the present invention refers to the root of *Clematis mandshurica*. In Chinese medicine, the root is used for gout, arthritis, jaundice, tetanus, etc.

*Ulmi radicis cortex* which is used in the present invention refers to the bark of *Ulmus davidiana*. It is effective against gastric ulcer, duodenal ulcer, small bowel ulcer, colon ulcer, edema, dropsy, gastric cancer, rectal cancer, uterine cancer, difficulty urination, ozena, nasitis, a boil, a tumor, a swelling, etc.

*Brassica campestris* which is used in the present invention refers to a rape. The rapeseed contains 38-45% of oil, which is an edible oil containing 15-20% of soluble nitrogen compounds and about 20% of proteins and is consumed in the largest amount next to bean oil. The residue remaining after pressing the oil from the seed is used as feedstuff or manure. The flower is a horny plant, and fatty oil separated from the seed is used as an ointment base, a solvent for oily injection formulations or a lubricant for machines.

*Cistanche deserticola* stem which is used in the present invention is a medicinal material using the freshy stem of *Cistanche deserticola* or other similar plants belonging to the family Orobanchaceae. It has a peculiar odor and is sweet, sour, salty and slightly bitter in taste and warm in nature. It strengthens Yang-Gi and is used for constipation caused by bowel dryness, lumbago caused by deficiency of the kidney Yang-Qi, a condition in which a leg becomes weak and powerless, tinnitus, forgetfulness, involuntary emission of semen, infertility, leucorrhea, cold abdomen, excessive bleeding, perspiration, constipation, etc. It was reported that the plant has various pharmacological effects, including lowering blood pressure, promoting *salvia* secretion and alleviating respiratory paralysis.

*Gypsophila oldhamiana* root which is used in the present invention refers to the root of *Gypsophila oldhamiana* belonging to the family Caryophyllaceae. It is odorless, acrid in acrid and slightly cold in nature. It is used for a fever caused by deficiency of Yin, a fever caused by overwork, a cold sweat, fever in children and infants, abdominal distension, etc. It was reported that the plant has various pharmacological effects, including preventing atherosclerosis, preventing cholesterol accumulation and alleviating fever, as well a spermicidal effect.

Eumn-yang-gak which is used in the present invention refers to the above-ground part of *Epimedium koreanum Nakai* or other similar plants belonging to the family Berberidaceae. It is used for impotence, involuntary emission of semen, cold-uterus conditions, cold-limb conditions, skin paralysis, facial nerve paralysis, forgetfulness, hemiplegia, weak waist and knee, hypertension, infantile paralysis, etc. It was reported that the plant has various pharmacological effects, including promoting semen secretion, lowering blood pressure, increasing coronary flow, lowering blood glucose levels, lowering blood cholesterol levels, promoting immune functions, relieving asthma and activating chicken femur growth and proteoglycan synthesis, as well as an antitussive effect, an expectorant effect, a sedative effect, an antibacterial effect, an inflammatory effect.

*Coicis semen* which is used in the present invention refers to a seed obtained by removing flesh from the seed of *Coix lachryma-jobi* belonging to the family Gramineae. It is used for dropsy, beriberi, difficult urination caused by a weak stomach, diarrhea, anorexia, limb paralysis, pain, difficult bending and spreading, muscular pain, fever, wound drainage, typhlitis, etc. It was reported that the plant has various pharmacological effects, including an anticancer effect, the effect of inhibiting skeletal muscle contraction, the effect of inhibition the bowel tract and uterine smooth muscle contraction, a sedative effect, an analgesic effect, an antipyretic effect, etc.

Ik-mo-cho which is used in the present invention refers to a medicinal drug obtained by drying the above-ground part of *Leonurus japonicus Houtt* (belonging to the family Lamiaceae) at the time of flowering. It removes extravasated blood during amenorrhea, menstrual pain, and bleeding abdominal pain caused by difficult uterine contraction after childbirth, and facilitates uterine contraction. It has a light diuretic effect and is used for difficult urination and body swelling, as well as eczema, itching, a boil, etc. It was reported that the plant has various pharmacological effects, including uterine excitation, thrombolysis, increasing the heart and coronary blood flow, excitation of breathing, urination, suppressing skin fungi, etc.

*Alpinia oxyphylla* fruit which is used in the present invention is the fruit of *Alpinia oxyphylla* belonging to the family Zingiberaceae. It is used for abdominal distension caused by a weak stomach, frequent urination caused by weak kidney function, powerless defecation, children nocturnal enuresis, uterine bleeding during childbirth, and sniveling resulting from deterioration in the convergent function of the spleen. It was reported that the plant has various pharmacological effects, including increasing hart contraction, suppressing ascites tumor cells and increasing ileum contraction.

*Ginseng* which is used in the present invention is a perennial dicotyledonous plant belonging to the family Araliaceae of the order Umbellales. The root is used for medicinal purposes and is human-shaped. *Ginseng* has been said to be a medicine for eternal youth, Qi enhancement and light body.

In-jin which is used in the present invention refers to a medicinal material obtained by drying the above-ground part of *Artemisiae Capillaris* belonging to the family Compositae. It is used for jaundice caused by damp heat, and symptoms accompanied by acute hepatitis, that is, fever, yellowing of the whole body, discharge of red urine, and little urination. Also, it is used for chronic hepatitis, cirrhosis, cholecystitis and gallbladder stones. In addition, it is also used for skin diseases, such as eczema, scabies, pityriasis, psoriasis and rubella, as well as high fever and insanity caused by an infectious disease. It was reported that In-jin has various pharmacological effects, including promoting bile secretion, alleviating fever, urination, antimicrobial activity, and suppressing ascites tumor cells.

*Angelica acutiloba* root which is used in the present invention is called "Il-dang-qui", "Il-bon-dang-qui", "Oae-dang-qui", "Cha-dang-qui" or "Gat-gang-hwal" in Korean and grows well in the seashore. The root is used as a medicinal material. It has immune functions, and thus is used as an anticancer agent and for anemia, menstrual irregularity, menstrual pain, body pain, etc. It is also used as a tonic. It was reported that the root has various pharmacological effects, including blood pressure-lowering and diuretic effects.

*Securinega suffruticosa* which is used in the present invention has the effects of activating blood circulation, relaxing muscular tissue, strengthening the spleen and improving kidney functions. It is used to treat rheumatoid lumbago, limb paralysis, hemiplegia, impotence, facial never paralysis, residual poliomyelitis, etc.

*Cnidium officinale* which is used in the present invention is a perennial plant belonging to the family Umbelliferae and is called "Il-cheon-goong", "Cheon-goong", "Goong-goong yi" or "Oae-cheon-goong" in Korean. It is effective in alleviating pain, suppressing convulsions, eliminating paralysis and promoting blood circulation.

*Aster* root which is used in the present invention refers to the root of *Aster tataricus* belonging to the family Compositae. It has a peculiar odor and is acrid and slightly bitter in taste and warm in nature. It acts to strengthen lung function, and thus is used for cough, phlegm, asthma and to enhance Qi and relive asthma. Particularly, it is used to treat an old cough and bloody phlegm. In addition, it is also used for a sour throat and acute and chronic respiratory infections. It was reported that the root has various pharmacological effects, including antitussive, expectorant and antimicrobial effects, as well as the effect of suppressing ascites tumor cells.

*Lithospermum erythrorhizon* which is used in the present invention is a mushroom growing on tree branches rising above the water in lakes, ponds, swamps and the like.

*Paeonia* which is used in the present invention refers to a collection of perennial plants belonging to the family Ranunculaceae. It is cultivated for ornamental purposes in a garden, because the flowers are large and beautiful. Examples thereof include *Paeonia alviflora, Paeonia japonica, Paeonia obovata, Paeonia albiflora* and the like. It is bitter and sour in taste and slightly cold in cold. It acts to clarify blood and eliminate extravasated blood, and thus is used for fever, hemoptysis, amenorrhoea, a bruise and the like.

*Adenophora triphylla* which is used in the present invention is a perennial plant belonging to the family Campanulaceae of the order Campanulales and is called "Jan-dae", "Sa-sam", "Dak-ju" or Je-ni" in Korean. The root of the plant is used as antitussive, expectorant, antipyretic, tonic and pus-draining agents.

*Ailanthus altissima* bark which is used in the present invention refers to the root bark of *Ailanthus altissima*. In Chinese medicine, it is effective against leucorrhea, diarrhea and bloody feces.

*Grifola umbellata* which is used inn the present invention is a mushroom belonging to the family Polyporaceae of the order Aphyllophorales of the class Basidiomycetes. In Chinese medicine, it is used as a diuretic agent.

*Poria cocos* red which is used in the present invention is the sclerotium of *Poria cocos* (Polyporaceae) which is parasitic on the pine root. It refers to a medicinal material obtained by removing the outer layer of the sclerotium. It is obtained by removing the outer layer with a knife, cutting the remaining inner part to a suitable size and drying the cut material in sunlight. Herein, when the inner part is white, it is referred to as *Poria cocos* white, and when the inner part is red, it is referred to as *Poria cocos* red. *Poria cocos* is used for difficult urination, abdominal and systemic edema, a cough by phlegm, vomiting, diarrhea, forgetfulness by hypersensitivity, involuntary emission of semen, and cardiac edema. It was reported that the medicinal material has various pharmacological effects, including urination, an antifungal effect, relaxation of gastrointestinal tract muscle, ulcer prevention, lowering blood glucose levels, increasing heart contraction, boosting immunity, an antitumor effect, etc.

*Polygonum multiflorum* root which is used in the present invention refers to a medicinal material obtained by drying the root of *Polygonum multiflorum Thunberg*. It is obtained by collecting the root of *Polygonum multiflorum Thunberg* in the fall and cutting or splitting the collected root, followed by drying. It is used to protect the bowels and stop diarrhea.

Red cabbage which is used in the present invention is a kind of cabbage belonging to the family Cruciferae. It is a health food which is effective in preventing gastric ulcer and aging and in restoring liver function. It is frequently used for decorative purposes in salad because of its beautiful color and is also used as sprout vegetables. It is richer in nutrients, such as fructose, glucose, vegetable protein lysine, and vitamin C, than common white cabbage. Also, it is rich in vitamin U, and thus effective against gastric ulcer. In addition, it is also rich in selenium which functions to prevent aging and mercury poisoning and restore liver function. However, it must be avoided that a person having low body temperature and suffering from frequent diarrhea takes red cabbage in a large amount.

*Paeoniae Radix Rubra* which is used in the present invention is a kind of *Paeoniae Radix*, and when the root is cut, it is reddish.

*Anthriscus sylvestris* which is used in the present invention is perennial plant belonging to the family Umbelliferae. It grows to a height of about 1 m, and the branch is split. The leaves have long stalks and are divided into feather shapes. In Chinese medicine, it refers to the root of *Angelica decursiva* and is used for headache, cough, phlegm, etc.

*Sorbus commixta cortex* which is used in the present invention refers to the stem cortex of *Sorbus commixta* which is a deciduous dicotyledonous tree belonging to the family Rosaceae of the order Rosales of Archichlamydeae. It has tonic, paralysis-removing and antitussive effects and is used to treat body weakness, sore waist and knee, limb paralysis by rheumatism, cough, white hair, etc.

*Syzygium aromaticum* which is used in the present invention refers to a clove bud. It is known that the plant is sweet and hot in taste, and thus effective in promoting appetite.

*Gleditsiae fructus* which is used in the present invention is also called "Jo-gak" or Jo-hyup" in Korean and refers to the fruit of *Gleditsia japonica* belonging to the family Leguminosae. It has a strong expectorant effect and is used for tuberculosis, lung abscess, chronic bronchitis, etc. It is also used for mental numbness by paralysis, unconsciousness, epilepsy, a boil, skin ulcer, constipation, etc. It was reported that the medicinal material has various pharmacological effects, including stimulating gastric mucosa, promoting mucous secretion in respiratory tracts, antibacterial activity, suppressing central nervous paralysis, etc.

*Gleditsiae spina* which is used in the present invention refers to the thorn of *Gleditsia japonica* belonging to the family Leguminosae. It has strong diuretic and anti-inflammatory effects, and thus is used to treat boils and neutralize boil's poison. It was reported that the medicinal material alleviates fever in acute tonsillitis and has an anti-inflammatory effect.

*Lophatherum gracile* which is used in the present invention refers to a monocotyledon bamboo belonging to the family Gramineae of the order Graminales.

*Cistanche deserticola* stem which is used in the present invention is also called "Yuk-jong-yong" and is a medicinal material using the freshy stem of *Cistanche deserticola* or other similar plants belonging to the family Orobanchaceae. It strengthens Yang-Gi and is used for constipation caused by bowel dryness, lumbago caused by deficiency of the kidney Yang-Qi, a condition in which a leg becomes weak and powerless, tinnitus, forgetfulness, involuntary emission of semen, infertility, leucorrhea, cold abdomen, excessive bleeding, perspiration, constipation, etc. It was reported that the plant has various pharmacological effects, including lowering blood pressure, promoting *salvia* secretion and alleviating respiratory paralysis.

*Phyllostachys nigra* sheath which is used in the present invention refers to the inner sheath of *Bambusa textilis* and has the effects of lowering fever, stopping vomiting, alleviating phlegm and stabilizing a fetus.

*Lycium chinensis* root which is used in the present invention refers to the dried root bark of *Lycium chinensis*. It is used for a cold sweat caused by body weakness, a cough, asthma, hemoptysis, nasal bleeding, bloody urine, hyperglycemia, high fever, neuralgia, headache, shoulder pain, muscular pain, lumbago, weak waist and knee, etc. It was reported that the root has various pharmacological effects, including lowering blood pressure and blood glucose levels.

*Hovenia dulcis* bark which is used in the present invention refers to the stem bark of *Hovenia dulcis*. It acts to facilitate blood circulation and relax muscle. It was reported to have the pharmacological effect of protecting the liver.

*Anemarrhena asphodeloides* which is used in the present invention is a monocotyledonous plant belonging to the family Haemodraceae of the order Veneroida, and the rhizome thereof contains asphonin, sarsapogenin, etc., which can be used as medicinal components. In Chinese medicine, the rhizome is used as a medicinal material, and it is used as an antipyretic agent and was reported to be effective against chronic bronchitis, diabetes and the like.

*Kochiae fructus* which is used in the present invention is also "Ji-bu-ja", "Dae-ssa-ri" or "Bi-ssa-ri" in Korean and refers to the seed of an annual plant belonging to the family Chenopodiaceae. It is used as a tonic and a diuretic and was reported to be effective against hyperthyroidism and atopic symptoms.

*Poncirus trifoliate* fruit which is used in the present invention refers to the young fruit of *Poncirus trifoliate*. It was found to be effective against a condition in which the chest and abdomen feel filling and swelling due to Qi stagnation, a condition the chest feels heavy and feels pain when being pressed, as well as edema, indigestion, constipation, etc. It was recently found that the fruit is effective against gastroptosis, uterine prolapse, protocele, etc. It was reported that the fruit has various pharmacological effects, including uterine contraction, gastric movement acceleration, heart stimulation, urination, etc.

*Sanguisorba officinalis* which is used in the present invention is used for diarrhea, colitis, bleeding, malignant boils, burns, etc. Particularly, it has strong hemostatic activity, and thus is used to stop bleeding.

*Rehmannia radix* which is used in the present invention is a plant belonging to the family Scrophulariaceae. It is classified into raw *Rehmannia glutinosa* which is the raw root of the plant, dried *Rehmannia glutinosa* which is obtained by drying the root, and *Rehmanniae radix preparata* which is obtained by steaming and drying the root. *Rehmanniae radix preparata* is used as a hematic and for menstrual irregularity, a weak constitution, children physical retardation, dementia, premature ejaculation, impotence and the like. Raw *Rehmanniae radix* is used for a weak constitution, hemoptysis, nasal bleeding, uterine bleeding, constipation and the like, and dried *Rehmanniae radix* is effective against thirst occurring after fever disease, and a disease symptomized by thirst due to the heat of the bowels, and acts to stop hemoptysis and nasal bleeding.

*Aconitum pseudolaeve Nakai* which is used in the present invention is a plant belonging to the family Ranunculaceae. In Chinese medicine, the dried root of the plant is used as a medicinal material, and it was reported to have paralysis-removing, analgesic and diuretic effects, and thus is used for arthritis, convulsions of muscle and bone, jaundice, difficult urination, etc.

Jin-o-ga-pi which is used in the present invention refers to a kind of *Acanthopanax*. It acts to eliminate wind-damp, promote blood circulation and relieve pain and functions to enhance kidney function to strengthen muscle and bone.

*Phyllanthus urinaria* which is used in the present invention is an annual plant of the family Euphorbiaceae, which grows in fields or grass fields. It is also called "Jin-ju-cho", "Yeo-woo-gu-seul", "Il-gae-ya-pye", "Sip-ja-jin-ju-cho", "Um-yang-cho", "Ga-yu-gam", "Jeuk-eo-cho", "Ho-su-su", "No-a-ju", "Ya-hap-jin-ju", "Rak-ji-yu-gam", "So-ri-gam", "Hal-cho", "Ya-hap-cho", "San-j o-gak", "Yup-hu-ju", "Yu-gam-cho" or "Eo-rin-cho" in Korean. It is known to be effective against chronic hepatitis, nephritis, enteritis and dysentery and has the effect of improving eyesight.

*Citrus unshiu* peel which is used in the present invention refers to the fruit peel of *Citrus unshiu*. It acts to relax Qi and enhance the function of fat, and thus is used to treat abdominal distension, belching, vomiting, nauseating, indigestion, flatulence and languishing, and loose feces. It relives cough and phlegm and facilitates urination. It was reported that the essential oil components of the peel has various pharmacological effects, including stimulating the digestive organs, promoting digestion, loosening phlegm, antiulcer activity, inhibiting gastric juice secretion, stimulating the heart, elevating blood pressure, antiallergic activity, promoting bile secretion, inhibiting uterine smooth muscle contraction, antimicrobial activity, etc.

*Plantaginis semen* which is used in the present invention refers to the seed of *Plantago asiatica*. It is used to facilitate urination, alleviate diarrhea, improve eyesight and stop coughing.

*Xanthium strumarium* fruit which is used in the present invention refers to the fruit of *Xanthium strumarium* belonging to the family Compositae. It is a medicinal material for eliminating "wind-cold" and is used for ozena, nasitis, headache, pyrexia, coughing, limb paralysis, difficult bending and spreading, itching, otitis media and the like. It was reported that the fruit has various pharmacological effects, including a toxic response to essential oil and alkaloid, lowering blood glucose levels, preventing the reduction of leucocytes, antitussive activity, promoting cardiovascular exercise, etc.

*Cnidii rhizoma* which is used in the present invention is a plant belonging to the family Umbelliferae. In Chinese medicine, the rhizome of the plant is used for headache, anemia, women's diseases and the like, because it has sedative, analgesic and tonic effects.

*Gastrodia elata* which is used in the present invention refers to a perennial monocotyledonous plant belonging to the family Orchidaceae of the order Orchidales. The whole plant is used as a tonic and for nervous breakdown, dizziness, headache, etc.

*Asparagus cochinchinensis* which is used in the present invention is a plant belonging to the family Veneridae. The soft shoot of the plant is used for eating purposes, and the root is used as antitussive, diuretic and tonic agents. It was reported that the plant must not be used for a person whose body is cold and who has a bowel trouble and thus suffers from diarrhea.

*Zanthoxyli frustus* which is used in the present invention is called "Cheon-cho" or "San-cho" and is the fruit peel of *Zanthoxylum piperitum* belonging to the family Rutaceae, which is obtained by removing a seed from the fruit. It is used for an abdominal pain caused by the chill of the abdomen, diarrhea, toothache, lumbago, etc. Also, it has insecticidal activity, and thus is used for scabies, scabs, itching of the secret parts, scrotal eczema, etc. It was reported that the fruit feel has various pharmacological effects, including regional anesthesia, gastrointestinal tract peristalsis, antibacterial activity, etc.

*Semiaquilegia adoxoides* which is used in the present invention is called "frog claw" in Korea and grows to a height of 20-30 cm in the mountain base. In Chinese medicine, it is used for difficult urination, urinary stones, inflammation of the lymphatic gland, piles, uteritis, gonorrhea, epilepsy and the like. In fork remedies, it is pulverized and applied to snake or insect bites.

*Opuntia humifusa* which is used in the present invention is also called dracaena, and about 50 kinds of dracaena are distributed in the tropics. The leaves are parallel veined, leathery, and lanceolate or broad-ovate. The leaves are 30-50 cm in length and 6-10 cm in width and have stalks. The stem is woody and upright, and spikelets are attached to the end of the stem. Small flowers, each having 6 flower leaves, grow in clusters.

*Dioscorea nipponica* Makino which is used in the present invention is also called "Cheon-san-ryoung" or "Dan-pung-ma" in Korean. In Chinese medicine, the rhizome of the plant is immersed in an alcoholic beverage and used for a condition resulting from the clotting and coagulation of extravasated blood. Also, it is used for coronary artery disorders caused by extravasated blood, acts to alleviate the coughing and asthma caused by the lung fever and to lower the blood fever, and thus is used for boils and rashes on the skin.

*Saussurea involucrata* which is used in the present invention is a perennial plant of the family Ranunculoideae, which grows in Tian Shan Mountain in China. In the plant, fibrous roots spread out from a thick and short rhizome in clusters, the stem is upright, and the base of the stem is surrounded by scaly leaves. It is known that the plant aids the rejuvenation of the male and is highly effective against women's diseases, cold-related diseases, kidney disease, arthritis, diabetes, wind-damp, uterine coldness, sickliness, etc.

*Trichosanthes kirilowii* root which is used in the present invention is called "Cheon-wha-boon" or "Kual-ru-keun" in Korean and refers to the root of *Trichosanthes kirilowii Maximowicz* or *Trichosanthes kirilowii Max.* var. *japonica Kitamura* of the family Cucurbitaceae, from which the cortex has been removed. It is used to treat a disease symptomized by thirst, which occurs when body fluid is deficient due to fever, as well as boils and pus. It acts to bring down the fever of mainly the lungs and the stomach and to make body fluid so as to relieve thirst and comfort the body. It was reported that the plant has various pharmacological effects, including suppressing squamous cell carcinoma, stimulating uterine smooth muscle contraction, inhibiting liver cells, lowering blood glucose levels, and inhibiting bacteria.

*Artemisia apiaceae Herba* which is used in the present invention is called "Cheong-Ho" in Korean. It acts to reduce hemorrhagic fever to treat malaria and the nausea, headache and vomiting caused by hot weather. Also, it is used to treat bone pain caused by consumptive fever, symptoms involving a slight fever, and a summer cold. In addition, it acts to improve the face color and make white hair black. It was reported that the plant has various pharmacological effects, including inhibiting malarial parasites and distoma hepaticum, lowering blood pressure, alleviating fever and inhibiting dermatomycosis, as well as antitussive, expectorant, asthma-relieving, bile-secreting and immunity-regulating effects.

*Amomi tsao-ko fructus* which is used in the present invention refers to the fruit of *Amomum tsao-ko CREVOST* belonging to the family Zingiberaceae. It acts to warm the stomach and spleen and remove damp and is used for abdominal pain, abdominal distension, nausea, vomiting, diarrhea, etc.

*Aconiti ciliare tuber* which is used in the present invention refers to the tuber root of *Aconitum cliliare* or other plants belonging to the family Ranunculaceae. It is used for headache, abdominal pain, boils, hemiplegia, unconsciousness and Bell's palsy. Also, it is used to treat the paralysis or unconsciousness caused by wind-damp disease, rheumatoid arthritis, neuralgia, lumbago, tetanus, an abdominal pain caused by abdominal coldness, etc. It was reported that the plant has various pharmacological effects, including analgesic, sedative, anti-inflammatory and partial paralysis-relieving effects and stimulates the heart work, when it is administered in a large amount.

*Gardeniae fructus* which is used in the present invention refers to the fruit of *Gardenia jasminoides* which is an evergreen shrub belonging to the family Rubiaceae. In Chinese medicine, it is used to treat insomnia and jaundice and has anti-inflammatory, hemostatic and diuretic effects.

*Celosiae semen* which is used in the present invention refers to the seed of *Celosia argentea Linne* belonging to the family Amaranthaceae. It brings down liver fever, and thus is used for congestion, white coating, hypertension, headache, etc. It is pharmacologically used for ophthalmic diseases and skin boils.

*Althaea rosea* which is used in the present invention refers to a hollyhock belonging to the family Malvaceae. It is used for leucorrhea, abdominal coldness, difficult urination and defecation, uterine bleeding, redness of the nasal tip, etc. It was reported to have a pharmacological effect against malaria.

*Aquillaria agallocha* which is used in the present invention is an evergreen tree belonging to the family Thymelaeaceae. In Chinese medicine, the stem is medicinally used and has sedative, stomachic and Qi-circulating effects. In addition, it is effective against indigestion, inappetence, vomiting, bronchial asthma, premature ejaculation, a decline in energy, etc.

Taek-ran which is used in the present invention refers to the above-ground part of *Lycopus lucidus* belonging to the family Labiatae before the time of flowering. It is used for amenorrhoea caused by extravasated blood, menstrual pain, abdominal pain after childbirth, and a bruise, and is effective against boils, liver function disturbance, and difficult urination after childbirth. It has an advantage in that it expels extravasated blood without damaging sprit and energy, and thus it is frequently used in gynecology. It was reported to have a cardiotonic effect.

*Alisma canaliculatum* which is used in the present invention is "Taek-sa" or "Swe-tae-na-mul" in Korean. In Chinese medicine, the rhizome is used as a diuretic agent and for dropsy and gonorrhea.

*Ponciri fructus* which is used in the present invention is the fruit of *Poncirus trifoliate*. It smells good and is also used for medicinal purposes.

*Smilacis chinae radix* which is used in the present invention refers to the root of *Smilax china Linne*. It contains a large amount of starch and is known to be effective against constipation, syphilis, gonorrhea, infant eczema, malignant boils, chronic dermatitis, mercury poisoning, flu, neuralgia, etc.

*Cuscutae semen* which is used in the present invention refers to the seed of *Cuscuta japonica* which is an annual climbing plant belonging to the family Convolvulaceae. It is known as a medicinal material which protects the liver and kidneys, improves eyesight, promotes Yang-qi and strengthens the kidneys. It is effective against male impotence caused by kidney weakness, spontaneous semen emission, a wet dream, etc. It acts to strengthen bone and the waist, and the sourness and pain of the waist and knee caused by weak kidney function. Also, it was reported that the plant is effective in treating diseases, involving urinary incontinence and difficult urination, and diabetes.

*Ligusticum rhizome* which is used in the present invention is the root of *Ligusticum chuanxiong*. It has antispasmodic, sedative, blood pressure lowering, vasodilator and antibacterial effects.

*Tetrapanacis medulla* which is used in the present invention refers to the stem of *Tetrapanax papyriferus* belonging to the family Araliaceae. It is known to bring down fever and increase urination. Thus, it is used to treat gonorrhea, urethritis and cystitis and promotes milk secretion after childbirth.

*Morinda offcinalis How* which is used in the present invention is called "Pa-keuk-cheon" or "No-ni" in Korean. In folk remedies, the leaf, stem, flower, fruit and seed of the plant have been used. In the ancient literature known in the South Pacific area, the plant is recorded as the best natural therapeutic agent. It was, in fact, found that the plant contains anthraquinone, serotonin and the like, and thus promotes digestion, alleviates pain and is effective against hypertension and cancer. It grows mainly in volcanic soil while taking root deep.

*Tiglii semen* which is used in the present invention refers to the seed of *Croton tiglium* which is an evergreen broadleaved shrub belonging to the family Euphorbiaceae. It is hot in taste and poisonous and is used for constipation or a condition in which the abdomen feels bloated due to filling of the abdomen with fluids.

*Taraxaci Herba* which is used in the present invention refers to the dried whole plant of *Taraxacum platycarpum* or other plants belonging to the same family. It acts to alleviate fever-poison and resolve boils and is used for boils, mastitis, a sore throat, carbuncles (appendicitis, Lung abscesses, and peritonitis), eyeball congestion, acute hepatitis, jaundice, difficult urination caused by fever, etc. It was reported that the plant has various pharmacological effects, including antibacterial, immune function-enhancing, bile-secreting, liver function-protecting and diuretic effects.

*Typhae pollen* which is used in the present invention refers to the pollen of *Typha orientalis* or other plants belonging to the family Typhaceae. It acts to bring down hemorrhagic fever and has convergent and hemostatic effects. It is used for hemoptysis, nasal bleeding and uterine bleeding. Also, it acts to improve blood circulation, and thus is used for the heart and abdominal pain caused by blood aggregation in the chest, a pain caused by extravasated blood after childbirth, and menstrual pain. It was reported that the plant has various pharmacological effects, including stimulating uterine contraction, lowering blood pressure, antimuscarinic activity, shortening the blood coagulation time, inhibiting the growth of tubercle bacilli, and lowering cholesterol levels.

*Calypso bulbosa* which is used in the present invention is called "Pung-seon-nan-cho", "Pung-seon-ran" or "Po-dae-ran" in Korean. It grows in coniferous forests to a height of about 30 cm. The rhizome is fleshy and ovate, and one leaf and stem come out from the tip of the rhizome. The leaf has a stalk and is egg-shaped or ovate. Also, the leaf is sharp at the end, round at the base, wrinkled vertically, and purple at the backside.

*Polygonum multiflorum* tuber which is used in the present invention is native to China and cultivated for medicinal purposes. It is reddish brown in color and used as a tonic, an aphrodisiac and a palliative. The leaf of the plant is used as seasoned vegetables, and the raw leaf is applied to a boil so as to absorb the pus.

*Aeschynomene indica* which is used in the present invention is called "Hap-maeng" or "Ja-gui-pul" in Korean. It grows in swampy land, and the stem is upright and grows to a height of 50-80 cm. The stem is branched and hollow at the top. The leaves are alternate and pinnately compound leaves. The leaflets consist of 20-30 pairs are ovate, plain at the margin and whitish at the backside.

*Armeniacae semen* which is used in the present invention refers to an apricot seed and is used for coughing, asthma, constipation and the like.

*Helianthus annus* seed which is used in the present invention refers to the seed of sunflower and acts to lower cholesterol levels and prevent cardiovascular diseases and arteriosclerosis. Also, it is rich in minerals, such as calcium, potassium and iron, and is highly effective for people whose respiratory organs are weak and body is cold and weak. In addition, it is rich in vitamin B antibody, and thus highly effective against hypertension or hypersensitivity.

*Cyperus rotundus* which is used in the present invention is a perennial plant belonging to the family Cyperaceae. The tuber root of the plant contains essential oil and fatty oil, and in Chinese medicine, it is used for headache, abdominal pain and menstrual irregularity. In folk remedies, it is also used as an antitussive in tuberculosis.

*Elsholtzia ciliata* which is used in the present invention is a plant belonging to the family Labiatae and is called "Hyang-yu" or "No-ya-gi" in Korean. In Chinese medicine, a medicinal material obtained by drying the whole plant at the time of flowering is used as diaphoretic, antipyretic, diuretic and hemostatic agents and for boils, beriberi, dropsy, gastritis, nasitis and bad breath.

*Cedrela sinensis* fruit which is used in the present invention refers to the fruit of *Cedrela sinensis*. It has the effects of removing paralysis, dispersing cold and relieving pain and is used to treat a disease caused by exogenous wind-cold, a heart or stomach pain, rheumatoid arthritis, and abdominal and waist pains.

*Typha orientalis* pollen which is used in the present invention is called "Hyang-po" or "Po-hwang" in Korean and refers to the pollen of *Typha orientalis* or other plants belonging to the family Typhaceae. It acts to bring down hemorrhagic fever and has convergent and hemostatic effects. It is used for hemoptysis, nasal bleeding and uterine bleeding. Also, it acts to improve blood circulation, and thus is used for the heart and abdominal pain caused by blood aggregation in the chest, a pain caused by extravasated blood after childbirth, and menstrual pain. It was reported that the plant has various pharmacological effects, including stimulating uterine contraction, lowering blood pressure, antimuscarinic activity, shortening the blood coagulation time, inhibiting the growth of tubercle bacilli, and lowering cholesterol levels.

*Scrophulariae radix* which is used in the present invention is a perennial plant belonging to the family Scrophulariaceae and is called "Hyun-sam", "Joong-dae", "Hyun-dae", "Gui-jang" or "Chook-ma" in Korean. In Chinese medicine, the root is used as an antipyretic and for a sore throat, boils, inflammation of the lymphatic gland, etc.

*Geranium nepalense* which is used in the present invention is an annual plant belonging to the family Geraniaceae. It acts to remove wind-damp and promote blood circulation to strengthen bone and muscle, and thus is used for paralytic pain, joint discomfort, a bruise, etc. In addition, it is effective against dysentery, chronic diarrhea and abdominal pain, enteritis, itching, scabies, malignant boils, etc.

*Corydalis turtschaninovii* which is used in the present invention is a perennial plant belonging to the family Fumariaceae of the order Papaverales and is "Hyun-ho-sac", "Nam-wha-chae" or "Won-ho" in Korean. In Chinese medicine, the tuber is used as a hematocathartic, an antispasmodic and an analgesic.

*Schizonepeta tenuifolia* which is used in the present invention is an annual plant belonging to the family Lamiaceae. In Chinese medicine, the dried whole plant is used for headache, a sore throat, and the case where boil sites bleed.

*Sesamum indicum* which is used in the present invention refers to sesame or black sesame. It acts to protect the liver and kidneys and is effective for people who have boils or a lot of gray hair.

*Trigonella foenum-graecum* which is used in the present invention is an annual plant belonging to the family Leguminosae of the order Rosales and grows to a height of about 50 cm. The *Trigonella* seed is medicinally used, after it is generally dried in sunlight. The seed contains a very small amount of essential oil which contains about 40 components, including alkaloids, proteins, fats, etc. It is warm in nature and non-poisonous, and thus has been used to treat diseases of the bladder and kidneys in Africa, the Middle East, India and others. It has also been used to treat a cold sweat or abdominal distension. These days, it is being actively studied, because it is effective in maintaining the balance between glucose and insulin in the body and regulating bodyweight.

*Cucurbita* spp which is used in the present invention is an annual climbing plant belonging to the Cucurbitaceae. It is known that the plant has the highest starch content among fruits and vegetables and the calorie value thereof is ranked next to potatoes, sweet potatoes and beans. It is generally used for cooking, and the ripened pumpkin is very important as a vitamin source, because it contains a large amount of vitamin A and some amounts of vitamins B and C.

*Acanthopanax giraldii* which is used in the present invention refers to *Acanthopanax senticosus* whose thorn is purplish red in color.

Red *ginseng* which is used in the present invention is obtained by steaming and drying fresh *ginseng*. It performs sedative action and stimulant action in the central nerve and acts on the circulating system to prevent hypertension or arteriosclerosis. Also, it has a hematopoietic effect, lowers blood glucose levels, protects the liver, acts on the endocrine system to act indirectly on sexual behavior or generative function, has anti-inflammatory and anti-tumor effects and a defense effect against radiation, and protects and smoothes the skin. One important effect of red *ginseng* is an adaptogen effect, and it has been scientifically proved that red *ginseng* has the ability to increase the defense ability of the living body against various harmful effects (stress, etc.) from the surrounding environment so as to allow the living body to more easily adapt to the environment.

Kombucha which is used in the present invention is a tea containing sugar, is prepared by culturing yeast and has an acid taste similar to that of lemon tea. Most of the acid taste is acetic acid, and Kombucha also contains organic acids such as gluconic acid.

*Herba Trifolii pratensis* which is used in the present invention is a perennial plant belonging to the family Leguminosae and is called "Hong-cha-chook-cho", "red clover" or "Keum-wha-chae" in Korean. In folk remedies, the whole plant is used as diuretic, analgesic, digestant, stomachic, expectorant and hemostatic agents, etc.

*Carthamus tinctorius* which is used in the present invention is the dried flower of *Carthamus tinctorius*. In Chinese medicine, it is used for women's diseases, menorrhalgia and abdominal pain, and the seed oil is used as lamp-oil and for eating purposes. The seed oil is rich in linolic acid, and thus effective in preventing and treating arteriosclerosis caused by hypercholesterolemia.

The floral envelop which is used in the present invention is a floral element which is located outside a stamen and a pistil so as to protect the stamen and the pistil.

*Scutellaria baicalensis* Georgi which is used in the present invention is a perennial plant belonging to the family Lamiaceae. In Chinese medicine, the root of the plant is used as antipyretic, diuretic, antidiarrheal, expectorant and anti-inflammatory agents.

*Astragalus membranaceus* which is used in the present invention refers to a perennial plant belonging to the family Leguminosae. It is frequently cultivated as an herb, and in Chinese medicine, it is obtained by collecting the plant in the fall, removing the head and root hairs from the collected plant and drying the residue in sunlight. It has tonic, antiperspirant, diuretic and anti-tumor effects, and thus is used for body weakness, fatigue, languor, deficiency of Qi blood, proctocele, uterine prolapse, a cold sweat, a peripheral nerve, etc.

*Coptis chinensis Franch* which is used in the present invention is cultivated for medicinal purposes. In Chinese medicine, it is obtained by collecting the root of a 5-6-old-year plant in November and drying the collected root in sunlight. It has stomachic, sedative, anti-inflammatory and antibacterial effects, and thus is used to treat indigestion, gastritis, enteritis, abdominal pain, vomiting, dysentery, heart palpitation, a febrile disease, mental anxiety, throat pain, hemoptysis, nasal bleeding, blood discharging, burns, etc.

*Polygonatum lasianthum* radix which is used in the present invention the root of *Polygonatum lasianthum*. It is used for body weakness, languidness, and weight loss.

*Lindera obtusiloba* branch which is used in the present invention refers to the dried branch of *Lindera obtusiloba*. In Chinese medicine, it is used for extravasated blood, afterpain, abdominal pain, and phlegm.

*Phellodendron amurense* bark which is used in the present invention refers to the dried bark of *Phellodendron amurense* belonging to the family Rutaceae and is "Hyang-baek" or "Hyang-kyung-pi" in Korean. It is obtained by collecting the bark from the tree stem, removing a coarse bark from the collected bark or cutting the bark, and drying the resulting bark in sunlight. The bark is medicinally used, acts to lower blood glucose levels, inhibit the growth of *Pneumococcus, mycobacterium tuberculosis, Staphylococcus* and the like and suppress the growth of tumor cells, and has a bactericidal effect. When it is administered, it stimulates the secretion of gastric juice by the acceleration of taste reflex and promotes appetite. Because it has no systemic action, unlike general alkaloids, it has no side effects, even when it is administered in a large amount. Thus, it can be used as intestinal antiseptic and stomachic agents. Also, because various kinds of bacteria do not tolerate the medicinal material, it can be used as an eye washing and sterilizing drug. In addition, it was reported to have the effects of lowering blood pressure, suppressing the central nervous system and inhibiting inflammation, and thus Hwang-ryun-hae-dok-tang, Si-ho-cheong-gan-tang, Hyeong-gae-yeon-gyo-tang and the like in Chinese medicine.

*Magnolia obovata* which is used in the present invention is an evergreen dicotyledonous tree belonging to the family Lauraceae of the order Ranales. In Chinese medicine, the bark of the tree is used for asthma and stomach trouble.

Black *Pharbitis semen* which is used in the present invention refers to the black seed of *Pharbitis nil Choisy*. It is obtained by collecting the seeds between September and October, drying the collected seeds, selecting only seeds having a dried fresh from the dried seeds, and drying the dried seeds. The dried seeds are classified into white *Pharbitis semen* having a white outer surface and black *Pharbitis semen* having a red outer surface. White *Pharbitis semen* and black *Pharbitis semen* have the same medicinal effects.

*Siegesbeckiae Herba* which is used in the present invention refers to the above-ground part of *Siegesbeckia glabrescens Makino* or *Siegesbeckia pubescens Makino* belonging to the family Compositae. It acts to remove wind-damp and is used for arthritis, limb pain and paralysis, difficult bending and spreading, lower-limb languidness, and hemiplegia. In addition, it is also used for boils, rashes, itching, eczema, hypertension, headache, dizziness, acute hepatitis, etc. It was reported to have various pharmacological effects, including inhibiting joint edema and lowering blood pressure.

The method for extracting medicinal plants, which is used in the present invention, is as follows.

(1) Step of Processing Medicinal Plants

Medicinal plants are processed by boiling or steaming, roasting, baking or heating them.

Specifically, processing is carried out at 60-100° C. for 2-10 hours for boiling, 100-150° C. for 30 minutes to 12 hours for steaming, 100-180° C. for 10 minutes to 5 hours for roasting, and 150-300° C. for 5-24 hours for baking.

If the processing conditions are out of the above-specified ranges, it will be difficult to obtain the desired effects, or the degree of improvement in effects will be insufficient.

(2) Step of Obtaining Extracts

Extracts of the medicinal plants processed in step (1) are obtained using water or an organic solvent. The organic solvent may be at least one selected from the group consisting of ethanol, methanol, butanol, ether, ethyl acetate and chloroform. Alternatively, a mixed solvent of the organic solvent with water may also be used. Preferably, 80% ethanol may be used.

The cosmetic composition of the present invention contains, as an active ingredient, the medicinal plant extract prepared as described above, in an amount of 0.001-30 wt % based on the total weight of the composition. If the content of the extract is less than 0.001 wt %, it will be difficult to obtain the desired effects, and if the content is more than 30 wt %, the change in effects will be insufficient.

Advantageous Effects

The inventive composition for skin external application, which contains an extract of a processed medicinal plant, shows an excellent antioxidant effect by inhibiting DPPH oxidation. Thus, the extract can be contained in a cosmetic composition or a pharmaceutical composition so as to provide an excellent antioxidant effect.

BEST MODE

Hereinafter, the present invention will be described in further detail with reference to examples and test examples. It is to be understood, however, that these examples are for illustrative purposes and are not to be construed to limit the scope of the present invention.

Comparative Example 1: Preparation of Unprocessed *Terminalia chebula Retz* Flesh Product 1 kg of dried *Terminalia chebula Retz* flesh was added to 5 L of 80% ethanol aqueous solution, extracted three times under reflux, and then maintained at 15° C. for 1 day. Following this, the solution was filtered through filter cloth and centrifuged into the residue and a filtrate. The separated filtrate was concentrated under reduced pressure, thus obtaining a *Terminalia chebula Retz* flesh extract.

Example 1-1: Preparation of Salted *Terminalia chebula Retz* Flesh 1 kg of dried *Terminalia chebula Retz* flesh was mixed well with brine (2-3% salt), closed and allowed to stand such that the brine was completely absorbed into the plant. Then, the plant was placed in a vessel at 100-180° C. and roasted for 10 minutes to 1 hour, followed by drying in the shade. The dried material was added to 5 L of 80% ethanol aqueous solution, extracted three times under reflux, and then maintained at 15° C. for 1 day. Then, the solution was filtered through filter cloth and centrifuged into the residue and a filtrate, and the separated filtrate was concentrated under reduced pressure, thus obtaining an extract of salted *Terminalia chebula Retz* flesh.

Example 1-2: Carbonized *Terminalia chebula Retz* Flesh

The surface of 1 kg of dried *Terminalia chebula Retz* flesh was carbonized by heating at 230-300° C., and when the surface was turned black, the heating was stopped and the plant was cooled at room temperature. Then, the carbonized plant was added to 5 L of 80% ethanol aqueous solution, extracted three times under reflux, and then maintained at 15° C. for 1 day. Then, the solution was filtered through filter cloth and centrifuged into the residue and a filtrate, and the separated filtrate was concentrated under reduced pressure, thus obtaining an extract of carbonized *Terminalia chebula Retz* flesh.

Example 1-3: Preparation of Vinegared *Terminalia chebula Retz* Flesh 1 kg of dried *Terminalia chebula Retz* flesh was sufficiently absorbed with 200-300 g of vinegar, and was then roasted at 100-160° C. for 10 minutes to 1 hour and dried in the shade. The dried plant was added to 5 L of 80% ethanol aqueous solution, extracted three times under reflux, and then maintained at 15° C. for 1 day. The, the solution was filtered through filter cloth and centrifuged into the residue and a filtrate, and the separated filtrate was concentrated under reduced pressure, thus obtaining an extract of vinegared *Terminalia chebula Retz* flesh.

Example 1-4: Preparation of Alcohol Steamed *Terminalia chebula Retz* Flesh 1 kg of dried *Terminalia chebula Retz* flesh was immersed in a given amount of huang-chiew (brewed alcoholic beverage), such that it was wet. The wet plant was steamed in a steamer for 30 minutes to 2 hours, and then dried in the shade. The steamed plant was added to 5 L of 80% ethanol aqueous solution, extracted three times under reflux, and then maintained at 15° C. for 1 day. Then, the solution was filtered through filter cloth and centrifuged into the residue and a filtrate, and the separated filtrate was concentrated under reduced pressure, thus obtaining an extract of alcohol steamed *Terminalia chebula Retz* flesh.

Example 1-5: Preparation of Gingered *Terminalia chebula Retz* Flesh

Fresh ginger was pulverized, added to a two-fold volume of water, pressed and then juiced. This was repeated 2-3 times to prepare a ginger juice. 100-150 g of the ginger juice was uniformly sprayed onto 1 kg of *Terminalia chebula Retz* flesh, and as the plant was impregnated with the ginger plant, it was roasted in a vessel at 100-180° C. for 10 minutes to 1 hour, and then dried in the shade. The dried material was added to 5 L of 80% ethanol aqueous solution, extracted three times under reflux, and then maintained at 15° C. for 1 day. Then, the solution was filtered through filter cloth and centrifuged into the residue and a filtrate, and the separated filtrate was concentrated under reduced pressure, thus obtaining an extract of gingered *Terminalia chebula Retz* flesh.

Example 1-6: Preparation of Honeyed *Terminalia chebula Retz* Flesh 1 kg of dried *Terminalia chebula Retz* flesh was sufficiently absorbed with 200-300 g of honey, and was then roasted at 100-160° C. for 10 minutes to 1 hour and dried in the shade. The dried plant was added to 5 L of 80% ethanol aqueous solution, extracted three times under reflux, and then maintained at 15° C. for 1 day. Then, the solution was filtered through filter cloth and centrifuged into the residue and a filtrate, and the separated filtrate was concentrated under reduced pressure, thus obtaining an extract of honeyed *Terminalia chebula Retz* flesh.

Comparative Examples 2 to 238: Preparation of Unprocessed Medicinal Plant Products 1 kg of each of the following medicinal plants was treated in the same manner as in Comparative Example 1, thus obtaining extracts of Comparative Examples 2 to 238 corresponding to the medicinal plants, respectively:

Dried *Pueraria* root, *Angelica koreana*, *Chrysanthemum indicum*, *Rehmanniae radix*, *Rhus verniciflua Stokes*, licorice, dried ginger, *Pharbitidis semen*, *Cassiae semen*, *Meliae cortex*, *Angelica tenuissima*, *Sophora flavescens*, *Caragana chamlagu*, *Trichosanthes semen*, *Lycii fructus*, *Agastache rugosa*, *Selaginella involvens*, *Citrus* peel, *Lonicera japonica* flower, *Chrysanthemum zawadskii*, *Chrysanthemum indicum*, *Platycodon grandiflorum*, *Cudrania tricuspidata*, *Raphani semen*, *Arisaema amurense*, *Cervi cornus colla*, *Phaseolus aureus*, antler velvet, *Trapa japonica* fruit, *Brassica rapa*, *Angelica acutiloba*, *Citrus grandis osbeck*, *Circium japonicum*, *Glycine semen germinatum*, *Datura stramonium*, *Zizyphus jujuba*, Dae-cheong-chow, *Rheum undulatum*, *Persicae semen*, *Aralia continentalis Kitagawa*, *Cordyceps militaris*, *Eucommiae cortex*, *Ephedra sinica*, *Portulaca oleracea*, *Rhododendron brachycarpum*, *Codonopsis pilosulae radix*, malt, *Liriopis tuber*, *Chaenomeles Sinensis* fruit, *Akebiae caulis*, *Saussurea lappa*, Mui, *Moutan cortex radicis*, *Mentha arvevsis*, Bang-pung, *Pinellia ternata*, Chinese cabbage, Bak-gul-chae, *Pulsatilla Koreana* root, *Cynanchi radix*, *Bletilla striata* tuber, *Santalum album*, *Ampelopsis japonica* root, white *Poria cocos*, *Aconitum koreanum*, *Thujae orientalis semen*, *Hedyotis diffusa*, *Paeonia japonica*, *Angelica dahurica* root, *Atractylodes macrocephala* rhizome, *Rubus coreanus* fruit, *Poria cocos*, *Arecae pericarpium*, *Aconiti radix*, *Allium tuberosum*, *Ostericum sieboldii*, borneol, Sa-kwa-rak, *Adenophorae radix*, wild ginseng radix, *Crataegus pinnatifida* fruit, *Cornus officianalis* fruit, *Dioscorea rhizoma*, *Zizyphi spinosi semen*, *Gardenia fructus*, *Saururus chinensis*, *Atractylodes japonica Koidzumi*, Sang-gi-saeng, *Mori cortex radicis*, *Dichroa febrifuga*, *Morus alba* leaf, *Abrus precatorius*, ginger, *Rhizoma acori graminei*, *Agrimonia pilosa ledebour*, Seol-kyun-cho, *Asarum sieboldi*, *Perilla frutescens* var. *acuta*, *Pinus densiflora*, *Jasminum floridum* root, *Anethum graveolens*, *Euphorbia lathyris* seed, *Dipsacus asper*, *Tricholoma matsutake*, *Cimicifuga heracleifolia*, *Bupleurum falcatum*, *Massa medicata fermentata*, *Artemisia* leaf, Yakssuk, *Lespedeza cuneata*, *Polygonum multiflorum* root, *Houttuynia cordata*, *Forsythia* fruit, *Nelumbinis semen*, *Nelumbo nucifera* seed, *Litchi chinensis*, *Papaver somniferum* flower, *Ganoderma lucidum*, *Aconitum carmichaeli*, *Acanthopanax sessiliflorus* bark, *Schizandra chinensis* fruit, *Chinensis Galla*, *Evodia officinalis*, *Linderae radix*, *Maydis stigmata*, *Polygonatum odoratum* root, *Orostachys japonicus*, *Solani nigri herba*, *Gentiana scabra BUNGE*, *Euphoria longana* testa, *Achyranthes japonica* root, *Polygalae radix*, *Genkwa flos*, *Oenothera odorata*, *Clematis mandshurica*, *Ulmi radicis cortex*, *Brassica campestris*, *Cistanche deserticola* stem, *Gypsophila oldhamiana* root, Eumn-yang-qwak, *Coicis semen*, Ik-mo-cho, *Alpinia oxyphylla* fruit, ginseng, In-jin, *Angelica acutiloba* root, *Securinega suffruticosa*, *Cnidium officinale*, *Aster* root, *Lithospermum erythrorhizon*, *Paeonia*, *Adenophora triphylla*, *ilanthus altissima* bark, *Grifola umbellata*, *Poria cocos* red, *Polygonum multiflorum Thunberg*, red cabbage, *Paeoniae Radix Rubra*, *Anthriscus sylvestris*, *Sorbus commixta cortex*, *Syzygium aromaticum*, *Gleditsiae fructus*, *Gleditsiae spina*, *Lophatherum gracile*, *Cistanche deserticola*, *Phyllostachys nigra* sheath, *Lycium chinensis* root, *Hovenia dulcis* bark, *Anemarrhena asphodeloides*, *Kochiae fructus*, *Poncirus trifoliate* fruit, *Sanguisorba officinalis*, *Rehmannia glutinosa*, *Aconitum pseudolaeve Nakai*, Jin-O-ga-pi, *Phyllanthus urinaria*, *Citrus unshiu* peel, *Plantaginis semen*, *Xanthium strumarium* fruit, *Cnidii rhizoma*, *Gastrodia elata*, *Asparagus cochinchinensis*, *Zanthoxyli fructus*, *Semiaquilegia adoxoides*, *Opuntia humifusa*, *Dioscorea nipponica Makino*, *Saussurea involucrata*, *Trichosanthes kirilowii* root, *Artemisia apiaceae Herba*, *Amomi tsao-ko fructus*, *Aconiti ciliare tuber*, *Gardeniae fructus*, *Celosiae semen*, *Althaea rosea*, *Aquillaria agallocha*, Taek-ran, *Alisma canaliculatum*, *Ponciri fructus*, *Smilacis chinae radix*, *Cuscutae semen*, *Ligusticum rhizome*, *Tetrapanacis medulla*, *Morinda offcinalis How*, *Tiglii semen*, *Taraxaci Herba*, *Typhae pollen*, *Calypso bulbosa*, *Polygonum multiflorum* tuber, *Aeschynomene indica*, *Armeniacae semen*, *Helianthus annus* seed, *Cyperus rotundus*, *Elsholtzia ciliata*, *Cedrela sinensis* fruit, *Typha orientalis* pollen, *Scrophulariae radix*, *Geranium nepalense*, *Corydalis turtschaninovii*, *Schizonepeta tenuifolia*, *Sesamum indicum*, *Trigonella foenum-graecum*, *Cucurbita* spp, *Acanthopanax giraldii*, red ginseng, Kombucha, *Herba Trifolii pratensis*, *Carthamus tinctorius*, floral envelop, *Scutellaria baicalensis Georgi*, *Astragalus membranaceus*, *Coptis chinensis Franch*, *Polygonatum lasianthum radix*, *Lindera obtusiloba* branch, *Phellodendron amurense* bark, *Magnolia obovata*, black *Pharbitis semen*, and *Siegesbeckiae Herba*.

Examples 2-1 to 238-1: Preparation of Salted Medicinal Plants 1 kg of each of the following medicinal plants was treated in the same manner as in Example 1-1, thus obtaining extracts of Examples 2-1 to 238-1 corresponding to the medicinal plants, respectively:

Dried *Pueraria* root, *Angelica koreana*, *Chrysanthemum indicum*, *Rehmanniae radix*, *Rhus verniciflua Stokes*, licorice, dried ginger, *Pharbitidis semen*, *Cassiae semen*, *Meliae cortex*, *Angelica tenuissima*, *Sophora flavescens*, *Caragana chamlagu*, *Trichosanthes semen*, *Lycii fructus*, *Agastache rugosa*, *Selaginella involvens*, *Citrus* peel, *Lonicera japonica* flower, *Chrysanthemum zawadskii*, *Chrysanthemum indicum*, *Platycodon grandiflorum*, *Cudrania tricuspidata*, *Raphani semen*, *Arisaema amurense*, *Cervi cornus colla*, *Phaseolus aureus*, antler velvet, *Trapa japonica* fruit, *Brassica rapa*, *Angelica acutiloba*, *Citrus grandis osbeck*, *Circium japonicum*, *Glycine semen germinatum*, *Datura stramonium*, *Zizyphus jujuba*, Dae-cheong-chow, *Rheum undulatum*, *Persicae semen*, *Aralia continentalis Kitagawa*, *Cordyceps militaris*, *Eucommiae cortex*, *Ephedra sinica*, *Portulaca oleracea*, *Rhododendron brachycarpum*, *Codonopsis pilosulae radix*, malt, *Liriopis tuber*, *Chaenomeles Sinensis* fruit, *Akebiae caulis*, *Saussurea lappa*, Mui, *Moutan cortex radicis*, *Mentha arvevsis*, Bang-pung, *Pinellia ternata*, Chinese cabbage, Bak-gul-chae, *Pulsatilla Koreana* root, *Cynanchi radix*, *Bletilla striata* tuber, *Santalum album*, *Ampelopsis japonica* root, white *Poria cocos*, *Aconitum koreanum*, *Thujae orientalis* semen, *Hedyotis diffusa*, *Paeonia japonica*, *Angelica dahurica* root, *Atractylodes macrocephala* rhizome, *Rubus coreanus* fruit, *Poria cocos*, *Arecae pericarpium*, *Aconiti radix*, *Allium tuberosum*, *Ostericum sieboldii*, borneol, Sa-kwa-rak, *Adenophorae radix*, wild ginseng radix, *Crataegus pinnatifida* fruit, *Cornus officianalis* fruit, *Dioscorea rhizoma*, *Zizyphi spinosi semen*, *Gardenia fructus*, *Saururus chinensis*, *Atractylodes japonica Koid-* zumi, Sang-gi-saeng, *Mori cortex radicis*, *Dichroa febrifuga*, *Morus alba* leaf, *Abrus precatorius*, ginger, *Rhizoma acori graminei*, *Agrimonia pilosa ledebour*, Seol-kyun-cho, *Asarum sieboldi*, *Perilla frutescens* var. *acuta*, *Pinus densiflora*, *Jasminum floridum* root, *Anethum graveolens*, *Euphorbia lathyris* seed, *Dipsacus asper*, *Tricholoma matsutake*, *Cimicifuga heracleifolia*, *Bupleurum falcatum*, *Massa medicata fermentata*, *Artemisia* leaf, Yakssuk, *Lespedeza cuneata*, *Polygonum multiflorum* root, *Houttuynia cordata*, *Forsythia* fruit, *Nelumbinis semen*, *Nelumbo nucifera* seed, *Litchi chinensis*, *Papaver somniferum* flower, *Ganoderma lucidum*, *Aconitum carmichaeli*, *Acanthopanax sessiliflorus* bark, *Schizandra chinensis* fruit, *Chinensis Galla*, *Evodia officinalis*, *Linderae radix*, *Maydis stigmata*, *Polygonatum odoratum* root, *Orostachys japonicus*, *Solani nigri herba*, *Gentiana scabra BUNGE*, *Euphoria longana* testa, *Achyranthes japonica* root, *Polygalae radix*, *Genkwa flos*, *Oenothera odorata*, *Clematis mandshurica*, *Ulmi radicis cortex*, *Brassica campestris*, *Cistanche deserticola* stem, *Gypsophila oldhamiana* root, Eumn-yang-qwak, *Coicis semen*, Ik-mo-cho, *Alpinia oxyphylla* fruit, ginseng, In-jin, *Angelica acutiloba* root, *Securinega suffruticosa*, *Cnidium officinale*, *Aster* root, *Lithospermum erythrorhizon*, *Paeonia*, *Adenophora triphylla*, *ilanthus altissima* bark, *Grifola umbellata*, *Poria cocos* red, *Polygonum multiflorum Thunberg*, red cabbage, *Paeoniae Radix Rubra*, *Anthriscus sylvestris*, *Sorbus commixta cortex*, *Syzygium aromaticum*, *Gleditsiae fructus*, *Gleditsiae spina*, *Lophatherum gracile*, *Cistanche deserticola*, *Phyllostachys nigra* sheath, *Lycium chinensis* root, *Hovenia dulcis* bark, *Anemarrhena asphodeloides*, *Kochiae fructus*, *Poncirus trifoliate* fruit, *Sanguisorba officinalis*, *Rehmannia glutinosa*, *Aconitum pseudolaeve Nakai*, Jin-O-ga-pi, *Phyllanthus urinaria*, *Citrus unshiu* peel, *Plantaginis semen*, *Xanthium strumarium* fruit, *Cnidii rhizoma*, *Gastrodia elata*, *Asparagus cochinchinensis*, *Zanthoxyli fructus*, *Semiaquilegia adoxoides*, *Opuntia humifusa*, *Dioscorea nipponica Makino*, *Saussurea involucrata*, *Trichosanthes kirilowii* root, *Artemisia apiaceae Herba*, *Amomi tsao-ko fructus*, *Aconiti ciliare tuber*, *Gardeniae fructus*, *Celosiae semen*, *Althaea rosea*, *Aquillaria agallocha*, Taek-ran, *Alisma canaliculatum*, *Ponciri fructus*, *Smilacis chinae radix*, *Cuscutae semen*, *Ligusticum rhizome*, *Tetrapanacis medulla*, *Morinda offcinalis How*, *Tiglii semen*, *Taraxaci Herba*, *Typhae pollen*, *Calypso bulbosa*, *Polygonum multiflorum* tuber, *Aeschynomene indica*, *Armeniacae semen*, *Helianthus annus* seed, *Cyperus rotundus*, *Elsholtzia ciliata*, *Cedrela sinensis* fruit, *Typha orientalis* pollen, *Scrophulariae radix*, *Geranium nepalense*, *Corydalis turtschaninovii*, *Schizonepeta tenuifolia*, *Sesamum indicum*, *Trigonella foenum-graecum*, *Cucurbita* spp., *Acanthopanax giraldii*, red ginseng, Kombucha, *Herba Trifolii pratensis*, *Carthamus tinctorius*, floral envelop, *Scutellaria baicalensis Georgi*, *Astragalus membranaceus*, *Coptis chinensis Franch*, *Polygonatum lasianthum radix*, *Lindera obtusiloba* branch, *Phellodendron amurense* bark, *Magnolia obovata*, black *Pharbitis semen*, and *Siegesbeckiae Herba*.

Examples 2-2 to 238-2: Preparation of Carbonized Medicinal Plants 1 kg of each of the following medicinal plants was treated in the same manner as in Example 1-2, thus obtaining extracts of Examples 2-2 to 238-2 corresponding to the medicinal plants, respectively:

Dried *Pueraria* root, *Angelica koreana*, *Chrysanthemum indicum*, *Rehmanniae radix*, *Rhus verniciflua Stokes*, licorice, dried ginger, *Pharbitidis semen*, *Cassiae semen*, *Meliae cortex*, *Angelica tenuissima*, *Sophora flavescens*, *Caragana chamlagu*, *Trichosanthes semen*, *Lycii fructus*, *Agastache rugosa*, *Selaginella involvens*, *Citrus* peel, *Lonicera japonica* flower, *Chrysanthemum zawadskii*, *Chrysanthemum indicum*, *Platycodon grandiflorum*, *Cudrania tricuspidata*, *Raphani semen*, *Arisaema amurense*, *Cervi cornus colla*, *Phaseolus aureus*, antler velvet, *Trapa japonica* fruit, *Brassica rapa*, *Angelica acutiloba*, *Citrus grandis osbeck*, *Circium japonicum*, *Glycine semen germinatum*, *Datura stramonium*, *Zizyphus jujuba*, Dae-cheong-chow, *Rheum undulatum*, *Persicae semen*, *Aralia continentalis Kitagawa*, *Cordyceps militaris*, *Eucommiae cortex*, *Ephedra sinica*, *Portulaca oleracea*, *Rhododendron brachycarpum*, *Codonopsis pilosulae radix*, malt, *Liriopis tuber*, *Chaenomeles Sinensis* fruit, *Akebiae caulis*, *Saussurea lappa*, Mui, *Moutan cortex radicis*, *Mentha arvevsis*, Bang-pung, *Pinellia ternata*, Chinese cabbage, Bak-gul-chae, *Pulsatilla Koreana* root, *Cynanchi radix*, *Bletilla striata* tuber, *Santalum album*, *Ampelopsis japonica* root, white *Poria cocos*, *Aconitum koreanum*, *Thujae orientalis semen*, *Hedyotis diffusa*, *Paeonia japonica*, *Angelica dahurica* root, *Atractylodes macrocephala* rhizome, *Rubus coreanus* fruit, *Poria cocos*, *Arecae pericarpium*, *Aconiti radix*, *Allium tuberosum*, *Ostericum sieboldii*, borneol, Sa-kwa-rak, *Adenophorae radix*, wild ginseng radix, *Crataegus pinnatifida* fruit, *Cornus officianalis* fruit, *Dioscorea rhizoma*, *Zizyphi spinosi semen*, *Gardenia fructus*, *Saururus chinensis*, *Atractylodes japonica Koidzumi*, Sang-gi-saeng, *Mori cortex radicis*, *Dichroa febrifuga*, *Morus alba* leaf, *Abrus precatorius*, ginger, *Rhizoma acori graminei*, *Agrimonia pilosa ledebour*, Seol-kyun-cho, *Asarum sieboldi*, *Perilla frutescens* var. *acuta*, *Pinus densiflora*, *Jasminum floridum* root, *Anethum graveolens*, *Euphorbia lathyris* seed, *Dipsacus asper*, *Tricholoma matsutake*, *Cimicifuga heracleifolia*, *Bupleurum falcatum*, *Massa medicata fermentata*, *Artemisia* leaf, Yakssuk, *Lespedeza cuneata*, *Polygonum multiflorum* root, *Houttuynia cordata*, *Forsythia* fruit, *Nelumbinis semen*, *Nelumbo nucifera* seed, *Litchi chinensis*, *Papaver somniferum* flower, *Ganoderma lucidum*, *Aconitum carmichaeli*, *Acanthopanax sessiliflorus* bark, *Schizandra chinensis* fruit, *Chinensis Galla*, *Evodia officinalis*, *Linderae radix*, *Maydis stigmata*, *Polygonatum odoratum* root, *Orostachys japonicus*, *Solani nigri herba*, *Gentiana scabra BUNGE*, *Euphoria longana* testa, *Achyranthes japonica* root, *Polygalae radix*, *Genkwa flos*, *Oenothera odorata*, *Clematis mandshurica*, *Ulmi radicis cortex*, *Brassica campestris*, *Cistanche deserticola* stem, *Gypsophila oldhamiana* root, Eumn-yang-qwak, *Coicis semen*, Ik-mo-cho, *Alpinia oxyphylla* fruit, ginseng, In-jin, *Angelica acutiloba* root, *Securinega suffruticosa*, *Cnidium officinale*, *Aster* root, *Lithospermum erythrorhizon*, *Paeonia*, *Adenophora triphylla*, *ilanthus altissima* bark, *Grifola umbellata*, *Poria cocos* red, *Polygonum multiflorum Thunberg*, red cabbage, *Paeoniae Radix Rubra*, *Anthriscus sylvestris*, *Sorbus commixta cortex*, *Syzygium aromaticum*, *Gleditsiae fructus*, *Gleditsiae spina*, *Lophatherum gracile*, *Cistanche deserticola*, *Phyllostachys nigra* sheath, *Lycium chinensis* root, *Hovenia dulcis* bark, *Anemarrhena asphodeloides*, *Kochiae fructus*, *Poncirus trifoliate* fruit, *Sanguisorba officinalis*, *Rehmannia glutinosa*, *Aconitum pseudolaeve Nakai*, Jin-O-ga-pi, *Phyllanthus urinaria*, *Citrus unshiu* peel, *Plantaginis semen*, *Xanthium strumarium* fruit, *Cnidii rhizoma*, *Gastrodia elata*, *Asparagus cochinchinensis*, *Zanthoxyli fructus*, *Semiaquilegia adoxoides*, *Opuntia humifusa*, *Dioscorea nipponica Makino*, *Saussurea involucrata*, *Trichosanthes kirilowii* root, *Artemisia apiaceae Herba*, *Amomi tsao-ko fructus*, *Aconiti ciliare tuber*, *Gardeniae fructus*, *Celosiae semen*, *Althaea rosea*,

*Aquillaria agallocha*, Taek-ran, *Alisma canaliculatum, Ponciri fructus, Smilacis chinae radix, Cuscutae semen, Ligusticum rhizome, Tetrapanacis medulla, Morinda offcinalis How, Tiglii semen, Taraxaci Herba, Typhae pollen, Calypso bulbosa, Polygonum multiflorum* tuber, *Aeschynomene indica, Armeniacae semen, Helianthus annus* seed, *Cyperus rotundus, Elsholtzia ciliata, Cedrela sinensis* fruit, *Typha orientalis* pollen, *Scrophulariae radix, Geranium nepalense, Corydalis turtschaninovii, Schizonepeta tenuifolia, Sesamum indicum, Trigonella foenum-graecum, Cucurbita* spp, *Acanthopanax giraldii*, red *ginseng*, Kombucha, *Herba Trifolii pratensis, Carthamus tinctorius*, floral envelop, *Scutellaria baicalensis Georgi, Astragalus membranaceus, Coptis chinensis Franch, Polygonatum lasianthum radix, Lindera obtusiloba* branch, *Phellodendron amurense* bark, *Magnolia obovata*, black *Pharbitis semen*, and *Siegesbeckiae Herba*.

Examples 2-3 to 238-3: Preparation of Vinegared Medicinal Plants 1 kg of each of the following medicinal plants was treated in the same manner as in Example 1-3, thus obtaining extracts of Examples 2-3 to 238-3 corresponding to the medicinal plants, respectively:

Dried *Pueraria* root, *Angelica koreana, Chrysanthemum indicum, Rehmanniae radix, Rhus verniciflua Stokes*, licorice, dried ginger, *Pharbitidis semen, Cassiae semen, Meliae cortex, Angelica tenuissima, Sophora flavescens, Caragana chamlagu, Trichosanthes semen, Lycii fructus, Agastache rugosa, Selaginella involvens, Citrus* peel, *Lonicera japonica* flower, *Chrysanthemum zawadskii, Chrysanthemum indicum, Platycodon grandiflorum, Cudrania tricuspidata, Raphani semen, Arisaema amurense, Cervi cornus colla, Phaseolus aureus*, antler velvet, *Trapa japonica* fruit, *Brassica rapa, Angelica acutiloba, Citrus grandis osbeck, Circium japonicum, Glycine semen germinatum, Datura stramonium, Zizyphus jujuba*, Dae-cheong-chow, *Rheum undulatum, Persicae semen, Aralia continentalis Kitagawa, Cordyceps militaris, Eucommiae cortex, Ephedra sinica, Portulaca oleracea, Rhododendron brachycarpum, Codonopsis pilosulae radix*, malt, *Liriopis tuber, Chaenomeles Sinensis* fruit, *Akebiae caulis, Saussurea lappa*, Mui, *Moutan cortex radicis, Mentha arvevsis*, Bang-pung, *Pinellia ternata*, Chinese cabbage, Bak-gul-chae, *Pulsatilla Koreana* root, *Cynanchi radix, Bletilla striata* tuber, *Santalum album, Ampelopsis japonica* root, white *Poria cocos, Aconitum koreanum, Thujae orientalis semen, Hedyotis diffusa, Paeonia japonica, Angelica dahurica* root, *Atractylodes macrocephala* rhizome, *Rubus coreanus* fruit, *Poria cocos, Arecae pericarpium, Aconiti radix, Allium tuberosum, Ostericum sieboldii*, borneol, Sa-kwa-rak, *Adenophorae radix*, wild *ginseng* radix, *Crataegus pinnatifida* fruit, *Cornus officianalis* fruit, *Dioscorea rhizoma, Zizyphi spinosi semen, Gardenia fructus, Saururus chinensis, Atractylodes japonica Koidzumi*, Sang-gi-saeng, *Mori cortex radicis, Dichroa febrifuga, Morus alba* leaf, *Abrus precatorius*, ginger, *Rhizoma acori graminei, Agrimonia pilosa ledebour*, Seolkyun-cho, *Asarum sieboldi, Perilla frutescens* var. *acuta, Pinus densiflora, Jasminum floridum* root, *Anethum graveolens, Euphorbia lathyris* seed, *Dipsacus asper, Tricholoma matsutake, Cimicifuga heracleifolia, Bupleurum falcatum, Massa medicata fermentata, Artemisia* leaf, Yakssuk, *Lespedeza cuneata, Polygonum multiflorum* root, *Houttuynia cordata, Forsythia* fruit, *Nelumbinis semen, Nelumbo nucifera* seed, *Litchi chinensis, Papaver somniferum* flower, *Ganoderma lucidum, Aconitum carmichaeli, Acanthopanax sessiliflorus* bark, *Schizandra chinensis* fruit, *Chinensis Galla, Evodia officinalis, Linderae radix, Maydis stigmata, Polygonatum odoratum* root, *Orostachys japonicus, Solani nigri herba, Gentiana scabra BUNGE, Euphoria longana* testa, *Achyranthes japonica* root, *Polygalae radix, Genkwa flos, Oenothera odorata, Clematis mandshurica, Ulmi radicis cortex, Brassica campestris, Cistanche deserticola* stem, *Gypsophila oldhamiana* root, Eumn-yang-qwak, *Coicis semen*, Ik-mo-cho, *Alpinia oxyphylla* fruit, *ginseng*, In-jin, *Angelica acutiloba* root, *Securinega suffruticosa, Cnidium officinale, Aster* root, *Lithospermum erythrorhizon, Paeonia, Adenophora triphylla, ilanthus altissima* bark, *Grifola umbellata, Poria cocos* red, *Polygonum multiflorum Thunberg*, red cabbage, *Paeoniae Radix Rubra, Anthriscus sylvestris, Sorbus commixta cortex, Syzygium aromaticum, Gleditsiae fructus, Gleditsiae spina, Lophatherum gracile, Cistanche deserticola, Phyllostachys nigra* sheath, *Lycium chinensis* root, *Hovenia dulcis* bark, *Anemarrhena asphodeloides, Kochiae fructus, Poncirus trifoliate* fruit, *Sanguisorba officinalis, Rehmannia glutinosa, Aconitum pseudolaeve Nakai*, Jin-O-ga-pi, *Phyllanthus urinaria, Citrus unshiu* peel, *Plantaginis semen, Xanthium strumarium* fruit, *Cnidii rhizoma, Gastrodia elata, Asparagus cochinchinensis, Zanthoxyli fructus, Semiaquilegia adoxoides, Opuntia humifusa, Dioscorea nipponica Makino, Saussurea involucrata, Trichosanthes kirilowii* root, *Artemisia apiaceae Herba, Amomi tsao-ko fructus, Aconiti ciliare* tuber, *Gardeniae fructus, Celosiae semen, Althaea rosea, Aquillaria agallocha*, Taek-ran, *Alisma canaliculatum, Ponciri fructus, Smilacis chinae radix, Cuscutae semen, Ligusticum rhizome, Tetrapanacis medulla, Morinda offcinalis How, Tiglii semen, Taraxaci Herba, Typhae pollen, Calypso bulbosa, Polygonum multiflorum* tuber, *Aeschynomene indica, Armeniacae semen, Helianthus annus* seed, *Cyperus rotundus, Elsholtzia ciliata, Cedrela sinensis* fruit, *Typha orientalis* pollen, *Scrophulariae radix, Geranium nepalense, Corydalis turtschaninovii, Schizonepeta tenuifolia, Sesamum indicum, Trigonella foenum-graecum, Cucurbita* spp, *Acanthopanax giraldii*, red *ginseng*, Kombucha, *Herba Trifolii pratensis, Carthamus tinctorius*, floral envelop, *Scutellaria baicalensis Georgi, Astragalus membranaceus, Coptis chinensis Franch, Polygonatum lasianthum radix, Lindera obtusiloba* branch, *Phellodendron amurense* bark, *Magnolia obovata*, black *Pharbitis semen*, and *Siegesbeckiae Herba*.

Examples 2-4 to 238-4: Preparation of Alcohol Steamed Medicinal Plants 1 kg of each of the following medicinal plants was treated in the same manner as in Example 1-4, thus obtaining extracts of Examples 2-4 to 238-4 corresponding to the medicinal plants, respectively:

Dried *Pueraria* root, *Angelica koreana, Chrysanthemum indicum, Rehmanniae radix, Rhus verniciflua Stokes*, licorice, dried ginger, *Pharbitidis semen, Cassiae semen, Meliae cortex, Angelica tenuissima, Sophora flavescens, Caragana chamlagu, Trichosanthes semen, Lycii fructus, Agastache rugosa, Selaginella involvens, Citrus* peel, *Lonicera japonica* flower, *Chrysanthemum zawadskii, Chrysanthemum indicum, Platycodon grandiflorum, Cudrania tricuspidata, Raphani semen, Arisaema amurense, Cervi cornus colla, Phaseolus aureus*, antler velvet, *Trapa japonica* fruit, *Brassica rapa, Angelica acutiloba, Citrus grandis osbeck, Circium japonicum, Glycine semen germinatum, Datura stramonium, Zizyphus jujuba*, Dae-cheong-chow, *Rheum undulatum, Persicae semen, Aralia continentalis Kitagawa, Cordyceps militaris, Eucommiae cortex, Ephedra sinica, Portulaca oleracea, Rhododendron brachycarpum, Codon-* opsis pilosulae radix, malt, *Liriopis tuber, Chaenomeles Sinensis* fruit, *Akebiae caulis, Saussurea lappa,* Mui, *Moutan cortex radicis, Mentha arvevsis,* Bang-pung, *Pinellia ternata,* Chinese cabbage, Bak-gul-chae, *Pulsatilla Koreana* root, *Cynanchi radix, Bletilla striata* tuber, *Santalum album, Ampelopsis japonica* root, white *Poria cocos, Aconitum koreanum, Thujae orientalis semen, Hedyotis diffusa, Paeonia japonica, Angelica dahurica* root, *Atractylodes macrocephala* rhizome, *Rubus coreanus* fruit, *Poria cocos, Arecae pericarpium, Aconiti radix, Allium tuberosum, Ostericum sieboldii,* borneol, Sa-kwa-rak, *Adenophorae radix,* wild ginseng radix, *Crataegus pinnatifida* fruit, *Cornus officianalis* fruit, *Dioscorea rhizoma, Zizyphi spinosi semen, Gardenia fructus, Saururus chinensis, Atractylodes japonica Koidzumi,* Sang-gi-saeng, *Mori cortex radicis, Dichroa febrifuga, Morus alba* leaf, *Abrus precatorius,* ginger, *Rhizoma acori graminei, Agrimonia pilosa ledebour,* Seolkyun-cho, *Asarum sieboldi, Perilla frutescens* var. *acuta, Pinus densiflora, Jasminum floridum* root, *Anethum graveolens, Euphorbia lathyris* seed, *Dipsacus asper, Tricholoma matsutake, Cimicifuga heracleifolia, Bupleurum falcatum, Massa medicata fermentata, Artemisia* leaf, Yakssuk, *Lespedeza cuneata, Polygonum multiflorum* root, *Houttuynia cordata, Forsythia* fruit, *Nelumbinis semen, Nelumbo nucifera* seed, *Litchi chinensis, Papaver somniferum* flower, *Ganoderma lucidum, Aconitum carmichaeli, Acanthopanax sessiliflorus* bark, *Schizandra chinensis* fruit, *Chinensis Galla, Evodia officinalis, Linderae radix, Maydis stigmata, Polygonatum odoratum* root, *Orostachys japonicus, Solani nigri herba, Gentiana scabra BUNGE, Euphoria longana* testa, *Achyranthes japonica* root, *Polygalae radix, Genkwa flos, Oenothera odorata, Clematis mandshurica, Ulmi radicis cortex, Brassica campestris, Cistanche deserticola* stem, *Gypsophila oldhamiana* root, Eumn-yang-qwak, *Coicis semen,* Ik-mo-cho, *Alpinia oxyphylla* fruit, ginseng, In-jin, *Angelica acutiloba* root, *Securinega suffruticosa, Cnidium officinale, Aster* root, *Lithospermum erythrorhizon, Paeonia, Adenophora triphylla, ilanthus altissima* bark, *Grifola umbellata, Poria cocos* red, *Polygonum multiflorum Thunberg,* red cabbage, *Paeoniae Radix Rubra, Anthriscus sylvestris, Sorbus commixta cortex, Syzygium aromaticum, Gleditsiae fructus, Gleditsiae spina, Lophatherum gracile, Cistanche deserticola, Phyllostachys nigra* sheath, *Lycium chinensis* root, *Hovenia dulcis* bark, *Anemarrhena asphodeloides, Kochiae fructus, Poncirus trifoliate* fruit, *Sanguisorba officinalis, Rehmannia glutinosa, Aconitum pseudolaeve Nakai,* Jin-O-ga-pi, *Phyllanthus urinaria, Citrus unshiu* peel, *Plantaginis semen, Xanthium strumarium* fruit, *Cnidii rhizoma, Gastrodia elata, Asparagus cochinchinensis, Zanthoxyli fructus, Semiaquilegia adoxoides, Opuntia humifusa, Dioscorea nipponica Makino, Saussurea involucrata, Trichosanthes kirilowii* root, *Artemisia apiaceae Herba, Amomi tsao-ko fructus, Aconiti ciliare tuber, Gardeniae fructus, Celosiae semen, Althaea rosea, Aquillaria agallocha,* Taek-ran, *Alisma canaliculatum, Ponciri fructus, Smilacis chinae radix, Cuscutae semen, Ligusticum rhizome, Tetrapanacis medulla, Morinda offcinalis How, Tiglii semen, Taraxaci Herba, Typhae pollen, Calypso bulbosa, Polygonum multiflorum* tuber, *Aeschynomene indica, Armeniacae semen, Helianthus annus* seed, *Cyperus rotundus, Elsholtzia ciliata, Cedrela sinensis* fruit, *Typha orientalis* pollen, *Scrophulariae radix, Geranium nepalense, Corydalis turtschaninovii, Schizonepeta tenuifolia, Sesamum indicum, Trigonella foenum-graecum, Cucurbita* spp, *Acanthopanax giraldii,* red ginseng, Kombucha, *Herba Trifolii pratensis, Carthamus tinctorius,* floral envelop, *Scutellaria baicalensis Georgi, Astragalus membranaceus, Coptis chinensis Franch, Polygonatum lasianthum radix, Lindera obtusiloba* branch, *Phellodendron amurense* bark, *Magnolia obovata,* black *Pharbitis semen,* and *Siegesbeckiae Herba.*

Examples 2-5 to 238-5: Preparation of Gingered Medicinal Plants 1 kg of each of the following medicinal plants was treated in the same manner as in Example 1-5, thus obtaining extracts of Examples 2-5 to 238-5 corresponding to the medicinal plants, respectively:

Dried *Pueraria* root, *Angelica koreana, Chrysanthemum indicum, Rehmanniae radix, Rhus verniciflua Stokes,* licorice, dried ginger, *Pharbitidis semen, Cassiae semen, Meliae cortex, Angelica tenuissima, Sophora flavescens, Caragana chamlagu, Trichosanthes semen, Lycii fructus, Agastache rugosa, Selaginella involvens, Citrus* peel, *Lonicera japonica* flower, *Chrysanthemum zawadskii, Chrysanthemum indicum, Platycodon grandiflorum, Cudrania tricuspidata, Raphani semen, Arisaema amurense, Cervi cornus colla, Phaseolus aureus,* antler velvet, *Trapa japonica* fruit, *Brassica rapa, Angelica acutiloba, Citrus grandis osbeck, Circium japonicum, Glycine semen germinatum, Datura stramonium, Zizyphus jujuba,* Dae-cheong-chow, *Rheum undulatum, Persicae semen, Aralia continentalis Kitagawa, Cordyceps militaris, Eucommiae cortex, Ephedra sinica, Portulaca oleracea, Rhododendron brachycarpum, Codonopsis pilosulae radix,* malt, *Liriopis tuber, Chaenomeles Sinensis* fruit, *Akebiae caulis, Saussurea lappa,* Mui, *Moutan cortex radicis, Mentha arvevsis,* Bang-pung, *Pinellia ternata,* Chinese cabbage, Bak-gul-chae, *Pulsatilla Koreana* root, *Cynanchi radix, Bletilla striata* tuber, *Santalum album, Ampelopsis japonica* root, white *Poria cocos, Aconitum koreanum, Thujae orientalis* semen, *Hedyotis diffusa, Paeonia japonica, Angelica dahurica* root, *Atractylodes macrocephala* rhizome, *Rubus coreanus* fruit, *Poria cocos, Arecae pericarpium, Aconiti radix, Allium tuberosum, Ostericum sieboldii,* borneol, Sa-kwa-rak, *Adenophorae radix,* wild ginseng radix, *Crataegus pinnatifida* fruit, *Cornus officianalis* fruit, *Dioscorea rhizoma, Zizyphi spinosi semen, Gardenia fructus, Saururus chinensis, Atractylodes japonica Koidzumi,* Sang-gi-saeng, *Mori cortex radicis, Dichroa febrifuga, Morus alba* leaf, *Abrus precatorius,* ginger, *Rhizoma acori graminei, Agrimonia pilosa ledebour,* Seolkyun-cho, *Asarum sieboldi, Perilla frutescens* var. *acuta, Pinus densiflora, Jasminum floridum* root, *Anethum graveolens, Euphorbia lathyris* seed, *Dipsacus asper, Tricholoma matsutake, Cimicifuga heracleifolia, Bupleurum falcatum, Massa medicata fermentata, Artemisia* leaf, Yakssuk, *Lespedeza cuneata, Polygonum multiflorum* root, *Houttuynia cordata, Forsythia* fruit, *Nelumbinis semen, Nelumbo nucifera* seed, *Litchi chinensis, Papaver somniferum* flower, *Ganoderma lucidum, Aconitum carmichaeli, Acanthopanax sessiliflorus* bark, *Schizandra chinensis* fruit, *Chinensis Galla, Evodia officinalis, Linderae radix, Maydis stigmata, Polygonatum odoratum* root, *Orostachys japonicus, Solani nigri herba, Gentiana scabra BUNGE, Euphoria longana* testa, *Achyranthes japonica* root, *Polygalae radix, Genkwa flos, Oenothera odorata, Clematis mandshurica, Ulmi radicis cortex, Brassica campestris, Cistanche deserticola* stem, *Gypsophila oldhamiana* root, Eumn-yang-qwak, *Coicis semen,* Ik-mo-cho, *Alpinia oxyphylla* fruit, ginseng, In-jin, *Angelica acutiloba* root, *Securinega suffruticosa, Cnidium officinale, Aster* root, *Lithospermum erythrorhizon, Paeonia, Adenophora triphylla, ilanthus altissima* bark, *Grifola umbellata, Poria cocos* red, *Polygonum multiflorum Thunberg,* red cabbage, *Paeoniae Radix Rubra, Anthriscus syl-* vestris, *Sorbus commixta cortex, Syzygium aromaticum, Gleditsiae fructus, Gleditsiae spina, Lophatherum gracile, Cistanche deserticola, Phyllostachys nigra* sheath, *Lycium chinensis* root, *Hovenia dulcis* bark, *Anemarrhena asphodeloides, Kochiae fructus, Poncirus trifoliate* fruit, *Sanguisorba officinalis, Rehmannia glutinosa, Aconitum pseudolaeve Nakai*, Jin-O-ga-pi, *Phyllanthus urinaria, Citrus unshiu* peel, *Plantaginis semen, Xanthium strumarium* fruit, *Cnidii rhizoma, Gastrodia elata, Asparagus cochinchinensis, Zanthoxyli fructus, Semiaquilegia adoxoides, Opuntia humifusa, Dioscorea nipponica Makino, Saussurea involucrata, Trichosanthes kirilowii* root, *Artemisia apiaceae Herba, Amomi tsao-ko fructus, Aconiti ciliare tuber, Gardeniae fructus, Celosiae semen, Althaea rosea, Aquillaria agallocha*, Taek-ran, *Alisma canaliculatum, Ponciri fructus, Smilacis chinae radix, Cuscutae semen, Ligusticum rhizome, Tetrapanacis medulla, Morinda offcinalis How, Tiglii semen, Taraxaci Herba, Typhae pollen, Calypso bulbosa, Polygonum multiflorum* tuber, *Aeschynomene indica, Armeniacae semen, Helianthus annus* seed, *Cyperus rotundus, Elsholtzia ciliata, Cedrela sinensis* fruit, *Typha orientalis* pollen, *Scrophulariae radix, Geranium nepalense, Corydalis turtschaninovii, Schizonepeta tenuifolia, Sesamum indicum, Trigonella foenum-graecum, Cucurbita* spp, *Acanthopanax giraldii*, red *ginseng*, Kombucha, *Herba Trifolii pratensis, Carthamus tinctorius*, floral envelop, *Scutellaria baicalensis Georgi, Astragalus membranaceus, Coptis chinensis Franch, Polygonatum lasianthum radix, Lindera obtusiloba* branch, *Phellodendron amurense* bark, *Magnolia obovata*, black *Pharbitis semen*, and *Siegesbeckiae Herba*.

Examples 2-6 to 238-6: Preparation of Honeyed Medicinal Plants 1 kg of each of the following medicinal plants was treated in the same manner as in Example 1-6, thus obtaining extracts of Examples 2-6 to 238-6 corresponding to the medicinal plants, respectively:

Dried *Pueraria* root, *Angelica koreana, Chrysanthemum indicum, Rehmanniae radix, Rhus verniciflua Stokes*, licorice, dried ginger, *Pharbitidis semen, Cassiae semen, Meliae cortex, Angelica tenuissima, Sophora flavescens, Caragana chamlagu, Trichosanthes semen, Lycii fructus, Agastache rugosa, Selaginella involvens, Citrus* peel, *Lonicera japonica* flower, *Chrysanthemum zawadskii, Chrysanthemum indicum, Platycodon grandiflorum, Cudrania tricuspidata, Raphani semen, Arisaema amurense, Cervi cornus colla, Phaseolus aureus*, antler velvet, *Trapa japonica* fruit, *Brassica rapa, Angelica acutiloba, Citrus grandis osbeck, Circium japonicum, Glycine semen germinatum, Datura stramonium, Zizyphus jujuba*, Dae-cheong-chow, *Rheum undulatum, Persicae semen, Aralia continentalis Kitagawa, Cordyceps militaris, Eucommiae cortex, Ephedra sinica, Portulaca oleracea, Rhododendron brachycarpum, Codonopsis pilosulae radix*, malt, *Liriopis tuber, Chaenomeles Sinensis* fruit, *Akebiae caulis, Saussurea lappa*, Mui, *Moutan cortex radicis, Mentha arvevsis*, Bang-pung, *Pinellia ternata*, Chinese cabbage, Bak-gul-chae, *Pulsatilla Koreana* root, *Cynanchi radix, Bletilla striata* tuber, *Santalum album, Ampelopsis japonica* root, white *Poria cocos, Aconitum koreanum, Thujae orientalis semen, Hedyotis diffusa, Paeonia japonica, Angelica dahurica* root, *Atractylodes macrocephala* rhizome, *Rubus coreanus* fruit, *Poria cocos, Arecae pericarpium, Aconiti radix, Allium tuberosum, Ostericum sieboldii*, borneol, Sa-kwa-rak, *Adenophorae radix*, wild *ginseng* radix, *Crataegus pinnatifida* fruit, *Cornus officianalis* fruit, *Dioscorea rhizoma, Zizyphi spinosi semen, Gardenia fructus, Saururus chinensis, Atractylodes japonica Koidzumi*, Sang-gi-saeng, *Mori cortex radicis, Dichroa febrifuga, Morus alba* leaf, *Abrus precatorius*, ginger, *Rhizoma acori graminei, Agrimonia pilosa ledebour*, Seolkyun-cho, *Asarum sieboldi, Perilla frutescens* var. *acuta, Pinus densiflora, Jasminum floridum* root, *Anethum graveolens, Euphorbia lathyris* seed, *Dipsacus asper, Tricholoma matsutake, Cimicifuga heracleifolia, Bupleurum falcatum, Massa medicata fermentata, Artemisia* leaf, Yakssuk, *Lespedeza cuneata, Polygonum multiflorum* root, *Houttuynia cordata, Forsythia* fruit, *Nelumbinis semen, Nelumbo nucifera* seed, *Litchi chinensis, Papaver somniferum* flower, *Ganoderma lucidum, Aconitum carmichaeli, Acanthopanax sessiliflorus* bark, *Schizandra chinensis* fruit, *Chinensis Galla, Evodia officinalis, Linderae radix, Maydis stigmata, Polygonatum odoratum* root, *Orostachys japonicus, Solani nigri herba, Gentiana scabra BUNGE, Euphoria longana* testa, *Achyranthes japonica* root, *Polygalae radix, Genkwa flos, Oenothera odorata, Clematis mandshurica, Ulmi radicis cortex, Brassica campestris, Cistanche deserticola* stem, *Gypsophila oldhamiana* root, Eumn-yang-qwak, *Coicis semen*, Ik-mo-cho, *Alpinia oxyphylla* fruit, *ginseng*, In-jin, *Angelica acutiloba* root, *Securinega suffruticosa, Cnidium officinale, Aster* root, *Lithospermum erythrorhizon, Paeonia, Adenophora triphylla, ilanthus altissima* bark, *Grifola umbellata, Poria cocos* red, *Polygonum multiflorum Thunberg*, red cabbage, *Paeoniae Radix Rubra, Anthriscus sylvestris, Sorbus commixta cortex, Syzygium aromaticum, Gleditsiae fructus, Gleditsiae spina, Lophatherum gracile, Cistanche deserticola, Phyllostachys nigra* sheath, *Lycium chinensis* root, *Hovenia dulcis* bark, *Anemarrhena asphodeloides, Kochiae fructus, Poncirus trifoliate* fruit, *Sanguisorba officinalis, Rehmannia glutinosa, Aconitum pseudolaeve Nakai*, Jin-O-ga-pi, *Phyllanthus urinaria, Citrus unshiu* peel, *Plantaginis semen, Xanthium strumarium* fruit, *Cnidii rhizoma, Gastrodia elata, Asparagus cochinchinensis, Zanthoxyli fructus, Semiaquilegia adoxoides, Opuntia humifusa, Dioscorea nipponica Makino, Saussurea involucrata, Trichosanthes kirilowii* root, *Artemisia apiaceae Herba, Amomi tsao-ko fructus, Aconiti ciliare tuber, Gardeniae fructus, Celosiae semen, Althaea rosea, Aquillaria agallocha*, Taek-ran, *Alisma canaliculatum, Ponciri fructus, Smilacis chinae radix, Cuscutae semen, Ligusticum rhizome, Tetrapanacis medulla, Morinda offcinalis How, Tiglii semen, Taraxaci Herba, Typhae pollen, Calypso bulbosa, Polygonum multiflorum* tuber, *Aeschynomene indica, Armeniacae semen, Helianthus annus* seed, *Cyperus rotundus, Elsholtzia ciliata, Cedrela sinensis* fruit, *Typha orientalis* pollen, *Scrophulariae radix, Geranium nepalense, Corydalis turtschaninovii, Schizonepeta tenuifolia, Sesamum indicum, Trigonella foenum-graecum, Cucurbita* spp, *Acanthopanax giraldii*, red *ginseng*, Kombucha, *Herba Trifolii pratensis, Carthamus tinctorius*, floral envelop, *Scutellaria baicalensis Georgi, Astragalus membranaceus, Coptis chinensis Franch, Polygonatum lasianthum radix, Lindera obtusiloba* branch, *Phellodendron amurense* bark, *Magnolia obovata*, black *Pharbitis semen*, and *Siegesbeckiae Herba*.

Test Example 1: Antioxidant Effect Test (DPPH Test)

Antioxidant activity was evaluated by the change in absorbance resulting from the reduction of the organic radical, 1,1-diphenyl-2-picryl hydrazyl (DPPH), (an antioxidant was oxidized). The degree of a reduction in absorbance as compared to the control group due to the inhibition of DPPH oxidation in each of the extracts of processed products of Examples and the extracts of unprocessed products of Comparative Examples was measured, and the concentration showing an absorbance which was 50% lower than that of the control group was recorded as effective antioxidant concentration.

190 μl of 100 μM DPPH solution in ethanol was mixed with 10 μl of each of the materials prepared in Examples and Comparative Examples and a control sample to make a reaction solution. Each of the reaction solutions was allowed to react at 37° C. for 30 minutes, and then measured for absorbance at 540 nm. As the control sample, the synthetic antioxidant Trolox was used. DPPH analysis results for each of the materials are shown in Tables 1 to 12 below. In Tables, $IC_{50}$ means the sample concentration at which the absorbance was reduced by 50% due to the addition of the sample.

TABLE 1

| DPPH analysis results (inhibition %) | |
|---|---|
| Sample | $IC_{50}$ (ppm) |
| Trolox | 45 |
| Comp. Exam. 1 | 180 |
| Example 1-1 | 40 |
| Example 1-2 | 44 |
| Example 1-3 | 36 |
| Example 1-4 | 31 |
| Example 1-5 | 37 |
| Example 1-6 | 41 |
| Comp. Exam. 2 | 160 |
| Example 2-1 | 30 |
| Example 2-2 | 44 |
| Example 2-3 | 35 |
| Example 2-4 | 37 |
| Example 2-5 | 23 |
| Example 2-6 | 34 |
| Comp. Exam. 3 | 240 |
| Example 3-1 | 45 |
| Example 3-2 | 42 |
| Example 3-3 | 34 |
| Example 3-4 | 21 |
| Example 3-5 | 47 |
| Example 3-6 | 41 |
| Comp. Exam. 4 | 135 |
| Example 4-1 | 37 |
| Example 4-2 | 23 |
| Example 4-3 | 34 |
| Example 4-4 | 37 |
| Example 4-5 | 23 |
| Example 4-6 | 34 |
| Comp. Exam. 5 | 123 |
| Example 5-1 | 31 |
| Example 5-2 | 44 |
| Example 5-3 | 33 |
| Example 5-4 | 37 |
| Example 5-5 | 56 |
| Example 5-6 | 23 |
| Comp. Exam. 6 | 174 |
| Example 6-1 | 45 |
| Example 6-2 | 42 |
| Example 6-3 | 44 |
| Example 6-4 | 33 |
| Example 6-5 | 37 |
| Example 6-6 | 56 |
| Comp. Exam. 7 | 166 |
| Example 7-1 | 37 |
| Example 7-2 | 37 |
| Example 7-3 | 23 |
| Example 7-4 | 34 |
| Example 7-5 | 23 |
| Example 7-6 | 34 |
| Comp. Exam. 8 | 173 |
| Example 8-1 | 31 |
| Example 8-2 | 44 |
| Example 8-3 | 73 |
| Example 8-4 | 37 |
| Example 8-5 | 56 |

TABLE 1-continued

| DPPH analysis results (inhibition %) | |
|---|---|
| Sample | $IC_{50}$ (ppm) |
| Example 8-6 | 23 |
| Comp. Exam. 9 | 184 |
| Example 9-1 | 40 |
| Example 9-2 | 42 |
| Example 9-3 | 44 |
| Example 9-4 | 33 |
| Example 9-5 | 37 |
| Example 9-6 | 56 |
| Comp. Exam. 10 | 121 |
| Example 10-1 | 37 |
| Example 10-2 | 33 |
| Example 10-3 | 23 |
| Example 10-4 | 34 |
| Example 10-5 | 23 |
| Example 10-6 | 34 |
| Comp. Exam. 11 | 165 |
| Example 11-1 | 30 |
| Example 11-2 | 44 |
| Example 11-3 | 35 |
| Example 11-4 | 31 |
| Example 11-5 | 23 |
| Example 11-6 | 34 |
| Comp. Exam. 12 | 115 |
| Example 12-1 | 45 |
| Example 12-2 | 42 |
| Example 12-3 | 34 |
| Example 12-4 | 21 |
| Example 12-5 | 46 |
| Example 12-6 | 41 |
| Comp. Exam. 13 | 135 |
| Example 13-1 | 37 |
| Example 13-2 | 34 |
| Example 13-3 | 37 |
| Example 13-4 | 37 |
| Example 13-5 | 23 |
| Example 13-6 | 34 |
| Comp. Exam. 14 | 123 |
| Example 14-1 | 21 |
| Example 14-2 | 44 |
| Example 14-3 | 79 |
| Example 14-4 | 37 |
| Example 14-5 | 56 |
| Example 14-6 | 23 |
| Comp. Exam. 15 | 243 |
| Example 15-1 | 37 |
| Example 15-2 | 23 |
| Example 15-3 | 34 |
| Example 15-4 | 37 |
| Example 15-5 | 23 |
| Example 15-6 | 34 |
| Comp. Exam. 16 | 153 |
| Example 16-1 | 31 |
| Example 16-2 | 44 |
| Example 16-3 | 33 |
| Example 16-4 | 37 |
| Example 16-5 | 56 |
| Example 16-6 | 23 |
| Comp. Exam. 17 | 211 |
| Example 17-1 | 45 |
| Example 17-2 | 42 |
| Example 17-3 | 44 |
| Example 17-4 | 33 |
| Example 17-5 | 37 |
| Example 17-6 | 56 |
| Comp. Exam. 18 | 142 |
| Example 18-1 | 40 |
| Example 18-2 | 42 |
| Example 18-3 | 44 |
| Example 18-4 | 33 |
| Example 18-5 | 37 |
| Example 18-6 | 56 |
| Comp. Exam. 19 | 229 |
| Example 19-1 | 37 |
| Example 19-2 | 33 |
| Example 19-3 | 23 |
| Example 19-4 | 34 |

TABLE 1-continued

DPPH analysis results (inhibition %)

| Sample | IC$_{50}$ (ppm) |
|---|---|
| Example 19-5 | 23 |
| Example 19-6 | 34 |
| Comp. Exam. 20 | 224 |
| Example 20-1 | 31 |
| Example 20-2 | 44 |
| Example 20-3 | 33 |
| Example 20-4 | 37 |
| Example 20-5 | 56 |
| Example 20-6 | 23 |
| Comp. Exam. 21 | 104 |
| Example 21-1 | 45 |
| Example 21-2 | 42 |
| Example 21-3 | 44 |
| Example 21-4 | 33 |
| Example 21-5 | 37 |
| Example 21-6 | 56 |

TABLE 2

| Sample | IC$_{50}$ (ppm) |
|---|---|
| Comp. Exam. 22 | 123 |
| Example 22-1 | 31 |
| Example 22-2 | 44 |
| Example 22-3 | 73 |
| Example 22-4 | 37 |
| Example 22-5 | 56 |
| Example 22-6 | 23 |
| Comp. Exam. 23 | 143 |
| Example 23-1 | 40 |
| Example 23-2 | 42 |
| Example 23-3 | 44 |
| Example 23-4 | 33 |
| Example 23-5 | 37 |
| Example 23-6 | 56 |
| Comp. Exam. 24 | 121 |
| Example 24-1 | 37 |
| Example 24-2 | 33 |
| Example 24-3 | 23 |
| Example 24-4 | 34 |
| Example 24-5 | 23 |
| Example 24-6 | 34 |
| Comp. Exam. 25 | 155 |
| Example 25-1 | 30 |
| Example 25-2 | 44 |
| Example 25-3 | 35 |
| Example 25-4 | 31 |
| Example 25-5 | 23 |
| Example 2-6 | 34 |
| Comp. Exam. 26 | 165 |
| Example 26-1 | 45 |
| Example 26-2 | 42 |
| Example 26-3 | 34 |
| Example 26-4 | 21 |
| Example 26-5 | 46 |
| Example 26-6 | 41 |
| Comp. Exam. 27 | 115 |
| Example 27-1 | 37 |
| Example 27-2 | 34 |
| Example 27-3 | 32 |
| Example 27-4 | 37 |
| Example 27-5 | 23 |
| Example 27-6 | 34 |
| Comp. Exam. 28 | 126 |
| Example 28-1 | 21 |
| Example 28-2 | 44 |
| Example 28-3 | 79 |
| Example 28-4 | 37 |
| Example 28-5 | 22 |
| Example 28-6 | 23 |
| Comp. Exam. 29 | 180 |
| Example 29-1 | 40 |
| Example 29-2 | 44 |

TABLE 2-continued

| Sample | IC$_{50}$ (ppm) |
|---|---|
| Example 29-3 | 36 |
| Example 29-4 | 31 |
| Example 29-5 | 37 |
| Example 29-6 | 41 |
| Comp. Exam. 30 | 160 |
| Example 30-1 | 30 |
| Example 30-2 | 44 |
| Example 30-3 | 35 |
| Example 30-4 | 37 |
| Example 30-5 | 23 |
| Example 30-6 | 34 |
| Comp. Exam. 31 | 222 |
| Example 31-1 | 45 |
| Example 31-2 | 42 |
| Example 31-3 | 34 |
| Example 31-4 | 21 |
| Example 31-5 | 47 |
| Example 31-6 | 41 |
| Comp. Exam. 32 | 135 |
| Example 32-1 | 37 |
| Example 32-2 | 23 |
| Example 32-3 | 34 |
| Example 32-4 | 37 |
| Example 32-5 | 23 |
| Example 32-6 | 34 |
| Comp. Exam. 33 | 332 |
| Example 33-1 | 31 |
| Example 33-2 | 44 |
| Example 33-3 | 83 |
| Example 33-4 | 47 |
| Example 33-5 | 56 |
| Example 33-6 | 23 |
| Comp. Exam. 34 | 174 |
| Example 34-1 | 45 |
| Example 34-2 | 42 |
| Example 34-3 | 44 |
| Example 34-4 | 55 |
| Example 34-5 | 37 |
| Example 34-6 | 56 |
| Comp. Exam. 35 | 166 |
| Example 35-1 | 37 |
| Example 35-2 | 65 |
| Example 35-3 | 23 |
| Example 35-4 | 34 |
| Example 35-5 | 23 |
| Example 35-6 | 34 |
| Comp. Exam. 36 | 114 |
| Example 36-1 | 31 |
| Example 36-2 | 44 |
| Example 36-3 | 73 |
| Example 36-4 | 37 |
| Example 36-5 | 56 |
| Example 36-6 | 23 |
| Comp. Exam. 37 | 144 |
| Example 37-1 | 40 |
| Example 37-2 | 42 |
| Example 37-3 | 34 |
| Example 37-4 | 33 |
| Example 37-5 | 37 |
| Example 37-6 | 56 |
| Comp. Exam. 38 | 134 |
| Example 38-1 | 37 |
| Example 38-2 | 33 |
| Example 38-3 | 54 |
| Example 38-4 | 34 |
| Example 38-5 | 23 |
| Example 38-6 | 34 |
| Comp. Exam. 39 | 143 |
| Example 39-1 | 30 |
| Example 39-2 | 44 |
| Example 39-3 | 35 |
| Example 39-4 | 31 |
| Example 39-5 | 23 |
| Example 39-6 | 34 |
| Comp. Exam. 40 | 176 |
| Example 40-1 | 45 |
| Example 40-2 | 42 |
| Example 40-3 | 53 |

TABLE 2-continued

| Sample | IC$_{50}$ (ppm) |
|---|---|
| Example 40-4 | 21 |
| Example 40-5 | 46 |
| Example 40-6 | 41 |
| Comp. Exam. 41 | 235 |
| Example 41-1 | 37 |
| Example 41-2 | 34 |
| Example 41-3 | 44 |
| Example 41-4 | 65 |
| Example 41-5 | 23 |
| Example 41-6 | 34 |
| Comp. Exam. 42 | 123 |
| Example 42-1 | 21 |
| Example 42-2 | 44 |
| Example 42-3 | 69 |
| Example 42-4 | 37 |
| Example 42-5 | 56 |
| Example 42-6 | 47 |

TABLE 3

| Sample | IC$_{50}$ (ppm) |
|---|---|
| Comp. Exam. 43 | 133 |
| Example 43-1 | 40 |
| Example 43-2 | 44 |
| Example 43-3 | 36 |
| Example 43-4 | 31 |
| Example 43-5 | 37 |
| Example 43-6 | 41 |
| Comp. Exam. 44 | 160 |
| Example 44-1 | 30 |
| Example 44-2 | 44 |
| Example 44-3 | 35 |
| Example 44-4 | 37 |
| Example 44-5 | 13 |
| Example 44-6 | 34 |
| Comp. Exam. 45 | 222 |
| Example 45-1 | 45 |
| Example 45-2 | 42 |
| Example 45-3 | 34 |
| Example 45-4 | 21 |
| Example 45-5 | 47 |
| Example 45-6 | 41 |
| Comp. Exam. 46 | 135 |
| Example 46-1 | 37 |
| Example 46-2 | 23 |
| Example 46-3 | 34 |
| Example 46-4 | 55 |
| Example 46-5 | 23 |
| Example 46-6 | 34 |
| Comp. Exam. 47 | 332 |
| Example 47-1 | 31 |
| Example 47-2 | 44 |
| Example 47-3 | 83 |
| Example 47-4 | 55 |
| Example 47-5 | 56 |
| Example 47-6 | 23 |
| Comp. Exam. 48 | 174 |
| Example 48-1 | 45 |
| Example 48-2 | 42 |
| Example 48-3 | 43 |
| Example 48-4 | 55 |
| Example 48-5 | 37 |
| Example 48-6 | 56 |
| Comp. Exam. 49 | 166 |
| Example 49-1 | 37 |
| Example 49-2 | 65 |
| Example 49-3 | 23 |
| Example 49-4 | 34 |
| Example 49-5 | 23 |
| Example 49-6 | 34 |
| Comp. Exam. 50 | 143 |
| Example 50-1 | 37 |
| Example 50-2 | 23 |
| Example 50-3 | 34 |

TABLE 3-continued

| Sample | IC$_{50}$ (ppm) |
|---|---|
| Example 50-4 | 37 |
| Example 50-5 | 23 |
| Example 50-6 | 34 |
| Comp. Exam. 51 | 153 |
| Example 51-1 | 31 |
| Example 51-2 | 44 |
| Example 51-3 | 65 |
| Example 51-4 | 37 |
| Example 51-5 | 56 |
| Example 51-6 | 23 |
| Comp. Exam. 52 | 211 |
| Example 52-1 | 45 |
| Example 52-2 | 42 |
| Example 52-3 | 44 |
| Example 52-4 | 33 |
| Example 52-5 | 37 |
| Example 52-6 | 56 |
| Comp. Exam. 53 | 142 |
| Example 53-1 | 40 |
| Example 53-2 | 42 |
| Example 53-3 | 44 |
| Example 53-4 | 33 |
| Example 53-5 | 37 |
| Example 53-6 | 56 |
| Comp. Exam. 54 | 229 |
| Example 54-1 | 37 |
| Example 54-2 | 33 |
| Example 54-3 | 23 |
| Example 54-4 | 43 |
| Example 54-5 | 23 |
| Example 54-6 | 34 |
| Comp. Exam. 55 | 224 |
| Example 55-1 | 31 |
| Example 55-2 | 44 |
| Example 55-3 | 65 |
| Example 55-4 | 37 |
| Example 55-5 | 56 |
| Example 55-6 | 23 |
| Comp. Exam. 56 | 104 |
| Example 56-1 | 45 |
| Example 56-2 | 42 |
| Example 56-3 | 55 |
| Example 56-4 | 33 |
| Example 56-5 | 37 |
| Example 56-6 | 56 |
| Comp. Exam. 57 | 175 |
| Example 57-1 | 30 |
| Example 57-2 | 44 |
| Example 57-3 | 35 |
| Example 57-4 | 43 |
| Example 57-5 | 23 |
| Example 57-6 | 34 |
| Comp. Exam. 58 | 165 |
| Example 58-1 | 65 |
| Example 58-2 | 42 |
| Example 58-3 | 43 |
| Example 58-4 | 21 |
| Example 58-5 | 46 |
| Example 58-6 | 41 |
| Comp. Exam. 59 | 115 |
| Example 59-1 | 37 |
| Example 59-2 | 34 |
| Example 59-3 | 32 |
| Example 59-4 | 37 |
| Example 59-5 | 23 |
| Example 59-6 | 34 |
| Comp. Exam. 60 | 126 |
| Example 60-1 | 33 |
| Example 60-2 | 44 |
| Example 60-3 | 79 |
| Example 60-4 | 37 |
| Example 60-5 | 22 |
| Example 60-6 | 23 |
| Comp. Exam. 61 | 160 |
| Example 61-1 | 30 |
| Example 61-2 | 44 |
| Example 61-3 | 35 |
| Example 61-4 | 37 |

TABLE 3-continued

| Sample | IC$_{50}$ (ppm) |
|---|---|
| Example 61-5 | 23 |
| Example 61-6 | 34 |
| Comp. Exam. 62 | 222 |
| Example 62-1 | 45 |
| Example 62-2 | 42 |
| Example 62-3 | 34 |
| Example 62-4 | 21 |
| Example 62-5 | 65 |
| Example 62-6 | 41 |
| Comp. Exam. 63 | 224 |
| Example 63-1 | 31 |
| Example 63-2 | 44 |
| Example 63-3 | 33 |
| Example 63-4 | 37 |
| Example 63-5 | 56 |
| Example 63-6 | 23 |

TABLE 4

| Sample | IC$_{50}$ (ppm) |
|---|---|
| Comp. Exam. 64 | 174 |
| Example 64-1 | 45 |
| Example 64-2 | 42 |
| Example 64-3 | 44 |
| Example 64-4 | 55 |
| Example 64-5 | 37 |
| Example 64-6 | 56 |
| Comp. Exam. 65 | 166 |
| Example 65-1 | 37 |
| Example 65-2 | 65 |
| Example 65-3 | 23 |
| Example 65-4 | 34 |
| Example 65-5 | 23 |
| Example 65-6 | 34 |
| Comp. Exam. 66 | 222 |
| Example 66-1 | 45 |
| Example 66-2 | 42 |
| Example 66-3 | 34 |
| Example 66-4 | 21 |
| Example 66-5 | 47 |
| Example 66-6 | 41 |
| Comp. Exam. 67 | 135 |
| Example 67-1 | 37 |
| Example 67-2 | 23 |
| Example 67-3 | 34 |
| Example 67-4 | 55 |
| Example 67-5 | 23 |
| Example 67-6 | 34 |
| Comp. Exam. 68 | 332 |
| Example 68-1 | 31 |
| Example 68-2 | 44 |
| Example 68-3 | 83 |
| Example 68-4 | 55 |
| Example 68-5 | 56 |
| Example 68-6 | 23 |
| Comp. Exam. 69 | 142 |
| Example 69-1 | 40 |
| Example 69-2 | 42 |
| Example 69-3 | 44 |
| Example 69-4 | 33 |
| Example 69-5 | 37 |
| Example 69-6 | 56 |
| Comp. Exam. 70 | 229 |
| Example 70-1 | 37 |
| Example 70-2 | 33 |
| Example 70-3 | 23 |
| Example 70-4 | 34 |
| Example 70-5 | 23 |
| Example 70-6 | 34 |
| Comp. Exam. 71 | 114 |
| Example 71-1 | 31 |
| Example 71-2 | 44 |
| Example 71-3 | 73 |
| Example 71-4 | 37 |

TABLE 4-continued

| Sample | IC$_{50}$ (ppm) |
|---|---|
| Example 71-5 | 56 |
| Example 71-6 | 23 |
| Comp. Exam. 72 | 144 |
| Example 72-1 | 40 |
| Example 72-2 | 42 |
| Example 72-3 | 34 |
| Example 72-4 | 33 |
| Example 72-5 | 37 |
| Example 72-6 | 56 |
| Comp. Exam. 73 | 134 |
| Example 73-1 | 37 |
| Example 73-2 | 33 |
| Example 73-3 | 54 |
| Example 73-4 | 34 |
| Example 73-5 | 23 |
| Example 73-6 | 34 |
| Comp. Exam. 74 | 143 |
| Example 74-1 | 30 |
| Example 74-2 | 44 |
| Example 74-3 | 35 |
| Example 74-4 | 31 |
| Example 74-5 | 23 |
| Example 74-6 | 34 |
| Comp. Exam. 75 | 176 |
| Example 75-1 | 45 |
| Example 75-2 | 42 |
| Example 75-3 | 53 |
| Example 75-4 | 21 |
| Example 75-5 | 46 |
| Example 75-6 | 41 |
| Comp. Exam. 76 | 235 |
| Example 76-1 | 37 |
| Example 76-2 | 34 |
| Example 76-3 | 44 |
| Example 76-4 | 65 |
| Example 76-5 | 23 |
| Example 76-6 | 34 |
| Comp. Exam. 77 | 123 |
| Example 77-1 | 21 |
| Example 77-2 | 44 |
| Example 77-3 | 69 |
| Example 77-4 | 37 |
| Example 77-5 | 56 |
| Example 77-6 | 47 |
| Comp. Exam. 78 | 135 |
| Example 78-1 | 37 |
| Example 78-2 | 23 |
| Example 78-3 | 34 |
| Example 78-4 | 55 |
| Example 78-5 | 23 |
| Example 78-6 | 34 |
| Comp. Exam. 79 | 332 |
| Example 79-1 | 31 |
| Example 79-2 | 44 |
| Example 79-3 | 83 |
| Example 79-4 | 55 |
| Example 79-5 | 56 |
| Example 79-6 | 23 |
| Comp. Exam. 80 | 174 |
| Example 80-1 | 45 |
| Example 80-2 | 42 |
| Example 80-3 | 56 |
| Example 80-4 | 55 |
| Example 80-5 | 37 |
| Example 80-6 | 56 |
| Comp. Exam. 81 | 166 |
| Example 81-1 | 37 |
| Example 81-2 | 65 |
| Example 81-3 | 23 |
| Example 81-4 | 34 |
| Example 81-5 | 23 |
| Example 81-6 | 34 |
| Comp. Exam. 82 | 160 |
| Example 82-1 | 30 |
| Example 82-2 | 44 |
| Example 82-3 | 35 |
| Example 82-4 | 37 |
| Example 82-5 | 23 |

TABLE 4-continued

| Sample | IC$_{50}$ (ppm) |
|---|---|
| Example 82-6 | 34 |
| Comp. Exam. 83 | 222 |
| Example 83-1 | 45 |
| Example 83-2 | 42 |
| Example 83-3 | 34 |
| Example 83-4 | 21 |
| Example 83-5 | 47 |
| Example 83-6 | 41 |
| Comp. Exam. 84 | 135 |
| Example 84-1 | 37 |
| Example 84-2 | 23 |
| Example 84-3 | 34 |
| Example 84-4 | 37 |
| Example 84-5 | 23 |
| Example 84-6 | 34 |

TABLE 5

| Sample | IC$_{50}$ (ppm) |
|---|---|
| Comp. Exam. 85 | 173 |
| Example 85-1 | 31 |
| Example 85-2 | 44 |
| Example 85-3 | 73 |
| Example 85-4 | 37 |
| Example 85-5 | 56 |
| Example 85-6 | 23 |
| Comp. Exam. 86 | 173 |
| Example 86-1 | 40 |
| Example 86-2 | 42 |
| Example 86-3 | 44 |
| Example 86-4 | 33 |
| Example 86-5 | 37 |
| Example 86-6 | 56 |
| Comp. Exam. 87 | 121 |
| Example 87-1 | 37 |
| Example 87-2 | 12 |
| Example 87-3 | 23 |
| Example 87-4 | 34 |
| Example 87-5 | 23 |
| Example 87-6 | 34 |
| Comp. Exam. 88 | 165 |
| Example 88-1 | 30 |
| Example 88-2 | 44 |
| Example 88-3 | 35 |
| Example 88-4 | 31 |
| Example 88-5 | 23 |
| Example 88-6 | 34 |
| Comp. Exam. 89 | 115 |
| Example 89-1 | 45 |
| Example 89-2 | 42 |
| Example 89-3 | 19 |
| Example 89-4 | 21 |
| Example 89-5 | 46 |
| Example 89-6 | 41 |
| Comp. Exam. 90 | 135 |
| Example 90-1 | 37 |
| Example 90-2 | 34 |
| Example 90-3 | 37 |
| Example 90-4 | 37 |
| Example 90-5 | 23 |
| Example 90-6 | 34 |
| Comp. Exam. 91 | 123 |
| Example 91-1 | 21 |
| Example 91-2 | 44 |
| Example 91-3 | 79 |
| Example 91-4 | 37 |
| Example 91-5 | 56 |
| Example 91-6 | 23 |
| Comp. Exam. 92 | 180 |
| Example 92-1 | 40 |
| Example 92-2 | 44 |
| Example 92-3 | 36 |
| Example 92-4 | 31 |
| Example 92-5 | 37 |

TABLE 5-continued

| Sample | IC$_{50}$ (ppm) |
|---|---|
| Example 92-6 | 41 |
| Comp. Exam. 93 | 160 |
| Example 93-1 | 30 |
| Example 93-2 | 54 |
| Example 93-3 | 35 |
| Example 93-4 | 37 |
| Example 93-5 | 23 |
| Example 93-6 | 34 |
| Comp. Exam. 94 | 240 |
| Example 94-1 | 45 |
| Example 94-2 | 42 |
| Example 94-3 | 34 |
| Example 94-4 | 21 |
| Example 94-5 | 47 |
| Example 94-6 | 33 |
| Comp. Exam. 95 | 135 |
| Example 95-1 | 37 |
| Example 95-2 | 23 |
| Example 95-3 | 34 |
| Example 95-4 | 37 |
| Example 95-5 | 23 |
| Example 95-6 | 34 |
| Comp. Exam. 96 | 123 |
| Example 96-1 | 31 |
| Example 96-2 | 44 |
| Example 96-3 | 33 |
| Example 96-4 | 37 |
| Example 96-5 | 56 |
| Example 96-6 | 23 |
| Comp. Exam. 97 | 174 |
| Example 97-1 | 45 |
| Example 97-2 | 42 |
| Example 97-3 | 44 |
| Example 97-4 | 33 |
| Example 97-5 | 37 |
| Example 97-6 | 56 |
| Comp. Exam. 98 | 166 |
| Example 98-1 | 37 |
| Example 98-2 | 55 |
| Example 98-3 | 23 |
| Example 98-4 | 34 |
| Example 98-5 | 23 |
| Example 98-6 | 34 |
| Comp. Exam. 99 | 165 |
| Example 99-1 | 30 |
| Example 99-2 | 44 |
| Example 99-3 | 35 |
| Example 99-4 | 31 |
| Example 99-5 | 23 |
| Example 99-6 | 34 |
| Comp. Exam. 100 | 134 |
| Example 100-1 | 37 |
| Example 100-2 | 33 |
| Example 100-3 | 54 |
| Example 100-4 | 34 |
| Example 100-5 | 23 |
| Example 100-6 | 34 |
| Comp. Exam. 101 | 143 |
| Example 101-1 | 30 |
| Example 101-2 | 14 |
| Example 101-3 | 35 |
| Example 101-4 | 31 |
| Example 101-5 | 23 |
| Example 101-6 | 34 |
| Comp. Exam. 102 | 176 |
| Example 102-1 | 45 |
| Example 102-2 | 42 |
| Example 102-3 | 53 |
| Example 102-4 | 21 |
| Example 102-5 | 46 |
| Example 102-6 | 41 |
| Comp. Exam. 103 | 235 |
| Example 103-1 | 37 |
| Example 103-2 | 34 |
| Example 103-3 | 44 |
| Example 103-4 | 65 |
| Example 103-5 | 23 |
| Example 103-6 | 34 |

TABLE 5-continued

| Sample | IC$_{50}$ (ppm) |
|---|---|
| Comp. Exam. 104 | 123 |
| Example 104-1 | 21 |
| Example 104-2 | 44 |
| Example 104-3 | 69 |
| Example 104-4 | 37 |
| Example 104-5 | 56 |
| Example 104-6 | 47 |
| Comp. Exam. 105 | 160 |
| Example 105-1 | 30 |
| Example 105-2 | 44 |
| Example 105-3 | 35 |
| Example 105-4 | 35 |
| Example 105-5 | 23 |
| Example 105-6 | 34 |

TABLE 6

| Sample | IC$_{50}$ (ppm) |
|---|---|
| Comp. Exam. 106 | 137 |
| Example 106-1 | 30 |
| Example 106-2 | 44 |
| Example 106-3 | 35 |
| Example 106-4 | 37 |
| Example 106-5 | 23 |
| Example 106-6 | 34 |
| Comp. Exam. 107 | 121 |
| Example 107-1 | 37 |
| Example 107-2 | 33 |
| Example 107-3 | 23 |
| Example 107-4 | 34 |
| Example 107-5 | 23 |
| Example 107-6 | 34 |
| Comp. Exam. 108 | 165 |
| Example 108-1 | 30 |
| Example 108-2 | 44 |
| Example 108-3 | 35 |
| Example 108-4 | 31 |
| Example 108-5 | 23 |
| Example 108-6 | 34 |
| Comp. Exam. 109 | 115 |
| Example 109-1 | 45 |
| Example 109-2 | 42 |
| Example 109-3 | 34 |
| Example 109-4 | 21 |
| Example 109-5 | 46 |
| Example 109-6 | 41 |
| Comp. Exam. 110 | 123 |
| Example 110-1 | 21 |
| Example 110-2 | 44 |
| Example 110-3 | 69 |
| Example 110-4 | 37 |
| Example 110-5 | 56 |
| Example 110-6 | 47 |
| Comp. Exam. 111 | 160 |
| Example 111-1 | 30 |
| Example 111-2 | 44 |
| Example 111-3 | 35 |
| Example 111-4 | 37 |
| Example 111-5 | 23 |
| Example 111-6 | 34 |
| Comp. Exam. 112 | 135 |
| Example 112-1 | 37 |
| Example 112-2 | 34 |
| Example 112-3 | 37 |
| Example 112-4 | 37 |
| Example 112-5 | 23 |
| Example 112-6 | 34 |
| Comp. Exam. 113 | 144 |
| Example 113-1 | 40 |
| Example 113-2 | 42 |
| Example 113-3 | 34 |
| Example 113-4 | 33 |
| Example 113-5 | 37 |
| Example 113-6 | 56 |

TABLE 6-continued

| Sample | IC$_{50}$ (ppm) |
|---|---|
| Comp. Exam. 114 | 134 |
| Example 114-1 | 37 |
| Example 114-2 | 33 |
| Example 114-3 | 54 |
| Example 114-4 | 34 |
| Example 114-5 | 23 |
| Example 114-6 | 34 |
| Comp. Exam. 115 | 177 |
| Example 115-1 | 45 |
| Example 115-2 | 42 |
| Example 115-3 | 56 |
| Example 115-4 | 55 |
| Example 115-5 | 37 |
| Example 115-6 | 56 |
| Comp. Exam. 116 | 166 |
| Example 116-1 | 37 |
| Example 116-2 | 65 |
| Example 116-3 | 23 |
| Example 116-4 | 34 |
| Example 116-5 | 23 |
| Example 116-6 | 34 |
| Comp. Exam. 115 | 160 |
| Example 117-1 | 30 |
| Example 117-2 | 44 |
| Example 117-3 | 35 |
| Example 117-4 | 37 |
| Example 117-5 | 23 |
| Example 117-6 | 34 |
| Comp. Exam. 118 | 115 |
| Example 118-1 | 45 |
| Example 118-2 | 42 |
| Example 118-3 | 64 |
| Example 118-4 | 21 |
| Example 118-5 | 46 |
| Example 118-6 | 41 |
| Comp. Exam. 119 | 123 |
| Example 119-1 | 21 |
| Example 119-2 | 44 |
| Example 119-3 | 55 |
| Example 119-4 | 37 |
| Example 119-5 | 56 |
| Example 119-6 | 47 |
| Comp. Exam. 120 | 121 |
| Example 120-1 | 37 |
| Example 120-2 | 33 |
| Example 120-3 | 23 |
| Example 120-4 | 34 |
| Example 120-5 | 23 |
| Example 120-6 | 34 |
| Comp. Exam. 121 | 165 |
| Example 121-1 | 30 |
| Example 121-2 | 44 |
| Example 121-3 | 35 |
| Example 121-4 | 31 |
| Example 121-5 | 23 |
| Example 121-6 | 34 |
| Comp. Exam. 122 | 154 |
| Example 122-1 | 37 |
| Example 122-2 | 33 |
| Example 122-3 | 23 |
| Example 122-4 | 34 |
| Example 122-5 | 23 |
| Example 122-6 | 34 |
| Comp. Exam. 123 | 155 |
| Example 123-1 | 30 |
| Example 123-2 | 44 |
| Example 123-3 | 35 |
| Example 123-4 | 31 |
| Example 123-5 | 23 |
| Example 123-6 | 34 |
| Comp. Exam. 124 | 165 |
| Example 124-1 | 45 |
| Example 124-2 | 42 |
| Example 124-3 | 34 |
| Example 124-4 | 21 |
| Example 124-5 | 46 |
| Example 124-6 | 41 |
| Comp. Exam. 125 | 123 |

TABLE 6-continued

| Sample | IC$_{50}$ (ppm) |
|---|---|
| Example 125-1 | 31 |
| Example 125-2 | 44 |
| Example 125-3 | 33 |
| Example 125-4 | 37 |
| Example 125-5 | 56 |
| Example 125-6 | 23 |
| Comp. Exam. 126 | 174 |
| Example 126-1 | 45 |
| Example 126-2 | 42 |
| Example 126-3 | 44 |
| Example 126-4 | 33 |
| Example 126-5 | 37 |
| Example 126-6 | 56 |

TABLE 7

| Sample | IC$_{50}$ (ppm) |
|---|---|
| Comp. Exam. 127 | 153 |
| Example 127-1 | 31 |
| Example 127-2 | 44 |
| Example 127-3 | 65 |
| Example 127-4 | 37 |
| Example 127-5 | 56 |
| Example 127-6 | 23 |
| Comp. Exam. 128 | 211 |
| Example 128-1 | 45 |
| Example 128-2 | 42 |
| Example 128-3 | 44 |
| Example 128-4 | 33 |
| Example 128-5 | 37 |
| Example 128-6 | 56 |
| Comp. Exam. 129 | 129 |
| Example 129-1 | 40 |
| Example 129-2 | 42 |
| Example 129-3 | 44 |
| Example 129-4 | 33 |
| Example 129-5 | 37 |
| Example 129-6 | 56 |
| Comp. Exam. 130 | 229 |
| Example 130-1 | 37 |
| Example 130-2 | 33 |
| Example 130-3 | 23 |
| Example 130-4 | 43 |
| Example 130-5 | 23 |
| Example 130-6 | 34 |
| Comp. Exam. 131 | 224 |
| Example 131-1 | 31 |
| Example 131-2 | 44 |
| Example 131-3 | 65 |
| Example 131-4 | 37 |
| Example 131-5 | 56 |
| Example 131-6 | 23 |
| Comp. Exam. 132 | 104 |
| Example 132-1 | 45 |
| Example 132-2 | 42 |
| Example 132-3 | 55 |
| Example 132-4 | 33 |
| Example 132-5 | 37 |
| Example 132-6 | 56 |
| Comp. Exam. 133 | 143 |
| Example 133-1 | 37 |
| Example 133-2 | 23 |
| Example 133-3 | 34 |
| Example 133-4 | 37 |
| Example 133-5 | 23 |
| Example 133-6 | 34 |
| Comp. Exam. 134 | 224 |
| Example 134-1 | 31 |
| Example 134-2 | 44 |
| Example 134-3 | 65 |
| Example 134-4 | 37 |
| Example 134-5 | 56 |
| Example 134-6 | 23 |
| Comp. Exam. 135 | 104 |

TABLE 7-continued

| Sample | IC$_{50}$ (ppm) |
|---|---|
| Example 135-1 | 45 |
| Example 135-2 | 42 |
| Example 135-3 | 55 |
| Example 135-4 | 33 |
| Example 135-5 | 37 |
| Example 135-6 | 56 |
| Comp. Exam. 136 | 211 |
| Example 136-1 | 45 |
| Example 136-2 | 42 |
| Example 136-3 | 44 |
| Example 136-4 | 33 |
| Example 136-5 | 37 |
| Example 136-6 | 56 |
| Comp. Exam. 137 | 142 |
| Example 137-1 | 40 |
| Example 137-2 | 42 |
| Example 137-3 | 44 |
| Example 137-4 | 33 |
| Example 137-5 | 37 |
| Example 137-6 | 56 |
| Comp. Exam. 138 | 229 |
| Example 138-1 | 37 |
| Example 138-2 | 33 |
| Example 138-3 | 23 |
| Example 138-4 | 43 |
| Example 138-5 | 23 |
| Example 138-6 | 34 |
| Comp. Exam. 139 | 123 |
| Example 139-1 | 21 |
| Example 139-2 | 44 |
| Example 139-3 | 69 |
| Example 139-4 | 37 |
| Example 139-5 | 56 |
| Example 139-6 | 47 |
| Comp. Exam. 140 | 165 |
| Example 140-1 | 30 |
| Example 140-2 | 44 |
| Example 140-3 | 35 |
| Example 140-4 | 31 |
| Example 140-5 | 23 |
| Example 140-6 | 34 |
| Comp. Exam. 141 | 123 |
| Example 141-1 | 31 |
| Example 141-2 | 44 |
| Example 141-3 | 73 |
| Example 141-4 | 37 |
| Example 141-5 | 56 |
| Example 141-6 | 23 |
| Comp. Exam. 142 | 143 |
| Example 142-1 | 40 |
| Example 142-2 | 42 |
| Example 142-3 | 44 |
| Example 142-4 | 33 |
| Example 142-5 | 37 |
| Example 142-6 | 56 |
| Comp. Exam. 143 | 121 |
| Example 143-1 | 37 |
| Example 143-2 | 33 |
| Example 143-3 | 23 |
| Example 143-4 | 34 |
| Example 143-5 | 23 |
| Example 143-6 | 34 |
| Comp. Exam. 144 | 155 |
| Example 144-1 | 30 |
| Example 144-2 | 44 |
| Example 144-3 | 35 |
| Example 144-4 | 31 |
| Example 144-5 | 23 |
| Example 144-6 | 34 |
| Comp. Exam. 145 | 165 |
| Example 145-1 | 45 |
| Example 145-2 | 42 |
| Example 145-3 | 34 |
| Example 145-4 | 21 |
| Example 145-5 | 46 |
| Example 145-6 | 41 |
| Comp. Exam. 146 | 145 |
| Example 146-1 | 37 |

TABLE 7-continued

| Sample | IC$_{50}$ (ppm) |
|---|---|
| Example 146-2 | 34 |
| Example 146-3 | 32 |
| Example 146-4 | 37 |
| Example 146-5 | 23 |
| Example 146-6 | 34 |
| Comp. Exam. 147 | 134 |
| Example 147-1 | 21 |
| Example 147-2 | 44 |
| Example 147-3 | 79 |
| Example 147-4 | 37 |
| Example 147-5 | 22 |
| Example 147-6 | 23 |

TABLE 8

| Sample | IC$_{50}$ (ppm) |
|---|---|
| Comp. Exam. 148 | 141 |
| Example 148-1 | 37 |
| Example 148-2 | 23 |
| Example 148-3 | 34 |
| Example 148-4 | 37 |
| Example 148-5 | 23 |
| Example 148-6 | 34 |
| Comp. Exam. 149 | 153 |
| Example 149-1 | 31 |
| Example 149-2 | 44 |
| Example 149-3 | 65 |
| Example 149-4 | 37 |
| Example 149-5 | 56 |
| Example 149-6 | 23 |
| Comp. Exam. 150 | 211 |
| Example 150-1 | 45 |
| Example 150-2 | 42 |
| Example 150-3 | 44 |
| Example 150-4 | 33 |
| Example 150-5 | 37 |
| Example 150-6 | 56 |
| Comp. Exam. 151 | 142 |
| Example 151-1 | 40 |
| Example 151-2 | 42 |
| Example 151-3 | 44 |
| Example 151-4 | 33 |
| Example 151-5 | 37 |
| Example 151-6 | 56 |
| Comp. Exam. 152 | 229 |
| Example 152-1 | 37 |
| Example 152-2 | 33 |
| Example 152-3 | 23 |
| Example 152-4 | 43 |
| Example 152-5 | 23 |
| Example 152-6 | 34 |
| Comp. Exam. 153 | 224 |
| Example 153-1 | 31 |
| Example 153-2 | 44 |
| Example 153-3 | 65 |
| Example 153-4 | 37 |
| Example 153-5 | 56 |
| Example 153-6 | 23 |
| Comp. Exam. 154 | 104 |
| Example 154-1 | 45 |
| Example 154-2 | 42 |
| Example 154-3 | 55 |
| Example 154-4 | 33 |
| Example 154-5 | 37 |
| Example 154-6 | 56 |
| Comp. Exam. 155 | 178 |
| Example 155-1 | 30 |
| Example 155-2 | 44 |
| Example 155-3 | 35 |
| Example 155-4 | 43 |
| Example 155-5 | 23 |
| Example 155-6 | 34 |
| Comp. Exam. 156 | 165 |
| Example 156-1 | 65 |

TABLE 8-continued

| Sample | IC$_{50}$ (ppm) |
|---|---|
| Example 156-2 | 42 |
| Example 156-3 | 43 |
| Example 156-4 | 21 |
| Example 156-5 | 46 |
| Example 156-6 | 41 |
| Comp. Exam. 157 | 115 |
| Example 157-1 | 37 |
| Example 157-2 | 34 |
| Example 157-3 | 32 |
| Example 157-4 | 37 |
| Example 157-5 | 23 |
| Example 157-6 | 34 |
| Comp. Exam. 158 | 126 |
| Example 158-1 | 33 |
| Example 158-2 | 44 |
| Example 158-3 | 79 |
| Example 158-4 | 37 |
| Example 158-5 | 22 |
| Example 158-6 | 23 |
| Comp. Exam. 159 | 160 |
| Example 159-1 | 30 |
| Example 159-2 | 44 |
| Example 159-3 | 35 |
| Example 159-4 | 37 |
| Example 159-5 | 23 |
| Example 159-6 | 34 |
| Comp. Exam. 160 | 222 |
| Example 160-1 | 45 |
| Example 160-2 | 42 |
| Example 160-3 | 34 |
| Example 160-4 | 21 |
| Example 160-5 | 65 |
| Example 160-6 | 41 |
| Comp. Exam. 161 | 224 |
| Example 161-1 | 31 |
| Example 161-2 | 44 |
| Example 161-3 | 33 |
| Example 161-4 | 37 |
| Example 161-5 | 56 |
| Example 161-6 | 23 |
| Comp. Exam. 162 | 137 |
| Example 162-1 | 30 |
| Example 162-2 | 44 |
| Example 162-3 | 35 |
| Example 162-4 | 37 |
| Example 162-5 | 23 |
| Example 162-6 | 34 |
| Comp. Exam. 163 | 121 |
| Example 163-1 | 37 |
| Example 163-2 | 33 |
| Example 163-3 | 23 |
| Example 163-4 | 34 |
| Example 163-5 | 23 |
| Example 163-6 | 34 |
| Comp. Exam. 164 | 165 |
| Example 164-1 | 30 |
| Example 164-2 | 44 |
| Example 164-3 | 35 |
| Example 164-4 | 31 |
| Example 164-5 | 23 |
| Example 164-6 | 34 |
| Comp. Exam. 165 | 115 |
| Example 165-1 | 45 |
| Example 165-2 | 42 |
| Example 165-3 | 34 |
| Example 165-4 | 21 |
| Example 165-5 | 46 |
| Example 165-6 | 41 |
| Comp. Exam. 166 | 123 |
| Example 166-1 | 21 |
| Example 166-2 | 44 |
| Example 166-3 | 69 |
| Example 166-4 | 37 |
| Example 166-5 | 56 |
| Example 166-6 | 47 |
| Comp. Exam. 167 | 160 |
| Example 167-1 | 30 |
| Example 167-2 | 44 |

TABLE 8-continued

| Sample | IC$_{50}$ (ppm) |
|---|---|
| Example 167-3 | 35 |
| Example 167-4 | 37 |
| Example 167-5 | 23 |
| Example 167-6 | 34 |
| Comp. Exam. 168 | 135 |
| Example 168-1 | 37 |
| Example 168-2 | 34 |
| Example 168-3 | 37 |
| Example 168-4 | 37 |
| Example 168-5 | 23 |
| Example 168-6 | 34 |

TABLE 9

| Sample | IC$_{50}$ (ppm) |
|---|---|
| Comp. Exam. 169 | 188 |
| Example 169-1 | 40 |
| Example 169-2 | 24 |
| Example 169-3 | 36 |
| Example 169-4 | 31 |
| Example 169-5 | 37 |
| Example 169-6 | 41 |
| Comp. Exam. 170 | 160 |
| Example 170-1 | 30 |
| Example 170-2 | 44 |
| Example 170-3 | 42 |
| Example 170-4 | 37 |
| Example 170-5 | 23 |
| Example 170-6 | 34 |
| Comp. Exam. 171 | 222 |
| Example 171-1 | 45 |
| Example 171-2 | 42 |
| Example 171-3 | 34 |
| Example 171-4 | 21 |
| Example 171-5 | 47 |
| Example 171-6 | 41 |
| Comp. Exam. 172 | 135 |
| Example 172-1 | 37 |
| Example 172-2 | 23 |
| Example 172-3 | 34 |
| Example 172-4 | 37 |
| Example 172-5 | 23 |
| Example 172-6 | 34 |
| Comp. Exam. 173 | 332 |
| Example 173-1 | 31 |
| Example 173-2 | 44 |
| Example 173-3 | 42 |
| Example 173-4 | 47 |
| Example 173-5 | 56 |
| Example 173-6 | 23 |
| Comp. Exam. 174 | 174 |
| Example 174-1 | 45 |
| Example 174-2 | 42 |
| Example 174-3 | 44 |
| Example 174-4 | 55 |
| Example 174-5 | 37 |
| Example 174-6 | 56 |
| Comp. Exam. 175 | 166 |
| Example 175-1 | 37 |
| Example 175-2 | 65 |
| Example 175-3 | 23 |
| Example 175-4 | 24 |
| Example 175-5 | 23 |
| Example 175-6 | 34 |
| Comp. Exam. 176 | 137 |
| Example 176-1 | 30 |
| Example 176-2 | 44 |
| Example 176-3 | 35 |
| Example 176-4 | 37 |
| Example 176-5 | 23 |
| Example 176-6 | 34 |
| Comp. Exam. 177 | 121 |
| Example 177-1 | 37 |
| Example 177-2 | 33 |

TABLE 9-continued

| Sample | IC$_{50}$ (ppm) |
|---|---|
| Example 177-3 | 23 |
| Example 177-4 | 34 |
| Example 177-5 | 23 |
| Example 177-6 | 34 |
| Comp. Exam. 178 | 165 |
| Example 178-1 | 30 |
| Example 178-2 | 44 |
| Example 178-3 | 35 |
| Example 178-4 | 31 |
| Example 178-5 | 23 |
| Example 178-6 | 34 |
| Comp. Exam. 179 | 115 |
| Example 179-1 | 45 |
| Example 179-2 | 42 |
| Example 179-3 | 34 |
| Example 179-4 | 21 |
| Example 179-5 | 46 |
| Example 179-6 | 41 |
| Comp. Exam. 180 | 123 |
| Example 180-1 | 21 |
| Example 180-2 | 44 |
| Example 180-3 | 69 |
| Example 180-4 | 37 |
| Example 180-5 | 56 |
| Example 180-6 | 47 |
| Comp. Exam. 181 | 160 |
| Example 181-1 | 30 |
| Example 181-2 | 44 |
| Example 181-3 | 35 |
| Example 181-4 | 37 |
| Example 181-5 | 23 |
| Example 181-6 | 34 |
| Comp. Exam. 182 | 135 |
| Example 182-1 | 37 |
| Example 182-2 | 34 |
| Example 182-3 | 37 |
| Example 182-4 | 37 |
| Example 182-5 | 23 |
| Example 182-6 | 34 |
| Comp. Exam. 183 | 174 |
| Example 183-1 | 31 |
| Example 183-2 | 44 |
| Example 183-3 | 65 |
| Example 183-4 | 37 |
| Example 183-5 | 56 |
| Example 183-6 | 23 |
| Comp. Exam. 184 | 104 |
| Example 184-1 | 45 |
| Example 184-2 | 42 |
| Example 184-3 | 55 |
| Example 184-4 | 33 |
| Example 184-5 | 37 |
| Example 184-6 | 56 |
| Comp. Exam. 185 | 211 |
| Example 185-1 | 45 |
| Example 185-2 | 42 |
| Example 185-3 | 44 |
| Example 185-4 | 33 |
| Example 185-5 | 37 |
| Example 185-6 | 56 |
| Comp. Exam. 186 | 142 |
| Example 186-1 | 40 |
| Example 186-2 | 42 |
| Example 186-3 | 44 |
| Example 186-4 | 33 |
| Example 186-5 | 37 |
| Example 186-6 | 56 |
| Comp. Exam. 187 | 229 |
| Example 187-1 | 37 |
| Example 187-2 | 33 |
| Example 187-3 | 23 |
| Example 187-4 | 43 |
| Example 187-5 | 23 |
| Example 187-6 | 34 |
| Comp. Exam. 188 | 123 |
| Example 188-1 | 21 |
| Example 188-2 | 44 |
| Example 188-3 | 69 |

TABLE 9-continued

| Sample | IC$_{50}$ (ppm) |
|---|---|
| Example 188-4 | 37 |
| Example 188-5 | 56 |
| Example 188-6 | 47 |
| Comp. Exam. 189 | 165 |
| Example 189-1 | 30 |
| Example 189-2 | 44 |
| Example 189-3 | 35 |
| Example 189-4 | 31 |
| Example 189-5 | 23 |
| Example 189-6 | 34 |

TABLE 10

| Sample | IC$_{50}$ (ppm) |
|---|---|
| Comp. Exam. 190 | 174 |
| Example 190-1 | 45 |
| Example 190-2 | 42 |
| Example 190-3 | 44 |
| Example 190-4 | 55 |
| Example 190-5 | 37 |
| Example 190-6 | 56 |
| Comp. Exam. 191 | 166 |
| Example 191-1 | 37 |
| Example 191-2 | 65 |
| Example 191-3 | 23 |
| Example 191-4 | 34 |
| Example 191-5 | 23 |
| Example 191-6 | 34 |
| Comp. Exam. 192 | 222 |
| Example 192-1 | 45 |
| Example 192-2 | 42 |
| Example 192-3 | 34 |
| Example 192-4 | 21 |
| Example 192-5 | 47 |
| Example 192-6 | 41 |
| Comp. Exam. 193 | 138 |
| Example 193-1 | 37 |
| Example 193-2 | 23 |
| Example 193-3 | 34 |
| Example 193-4 | 55 |
| Example 193-5 | 23 |
| Example 193-6 | 34 |
| Comp. Exam. 194 | 332 |
| Example 194-1 | 31 |
| Example 194-2 | 44 |
| Example 194-3 | 33 |
| Example 194-4 | 55 |
| Example 194-5 | 56 |
| Example 194-6 | 23 |
| Comp. Exam. 195 | 142 |
| Example 195-1 | 40 |
| Example 195-2 | 42 |
| Example 195-3 | 44 |
| Example 195-4 | 33 |
| Example 195-5 | 37 |
| Example 195-6 | 56 |
| Comp. Exam. 196 | 229 |
| Example 196-1 | 37 |
| Example 196-2 | 33 |
| Example 196-3 | 23 |
| Example 196-4 | 34 |
| Example 196-5 | 23 |
| Example 196-6 | 34 |
| Comp. Exam. 197 | 178 |
| Example 197-1 | 30 |
| Example 197-2 | 44 |
| Example 197-3 | 35 |
| Example 197-4 | 43 |
| Example 197-5 | 23 |
| Example 197-6 | 34 |
| Comp. Exam. 198 | 165 |
| Example 198-1 | 65 |
| Example 198-2 | 42 |
| Example 198-3 | 43 |

TABLE 10-continued

| Sample | IC$_{50}$ (ppm) |
|---|---|
| Example 198-4 | 21 |
| Example 198-5 | 46 |
| Example 198-6 | 41 |
| Comp. Exam. 199 | 126 |
| Example 199-1 | 37 |
| Example 199-2 | 34 |
| Example 199-3 | 43 |
| Example 199-4 | 37 |
| Example 199-5 | 23 |
| Example 199-6 | 34 |
| Comp. Exam. 200 | 126 |
| Example 200-1 | 33 |
| Example 200-2 | 44 |
| Example 200-3 | 79 |
| Example 200-4 | 37 |
| Example 200-5 | 22 |
| Example 200-6 | 23 |
| Comp. Exam. 201 | 160 |
| Example 201-1 | 30 |
| Example 201-2 | 44 |
| Example 201-3 | 35 |
| Example 201-4 | 37 |
| Example 201-5 | 34 |
| Example 201-6 | 34 |
| Comp. Exam. 202 | 222 |
| Example 202-1 | 45 |
| Example 202-2 | 42 |
| Example 202-3 | 34 |
| Example 202-4 | 21 |
| Example 202-5 | 65 |
| Example 202-6 | 41 |
| Comp. Exam. 203 | 224 |
| Example 203-1 | 31 |
| Example 203-2 | 44 |
| Example 203-3 | 33 |
| Example 203-4 | 37 |
| Example 203-5 | 56 |
| Example 203-6 | 23 |
| Comp. Exam. 204 | 121 |
| Example 204-1 | 37 |
| Example 204-2 | 33 |
| Example 204-3 | 23 |
| Example 204-4 | 34 |
| Example 204-5 | 23 |
| Example 204-6 | 34 |
| Comp. Exam. 205 | 161 |
| Example 205-1 | 30 |
| Example 205-2 | 44 |
| Example 205-3 | 35 |
| Example 205-4 | 31 |
| Example 205-5 | 23 |
| Example 205-6 | 34 |
| Comp. Exam. 206 | 154 |
| Example 206-1 | 37 |
| Example 206-2 | 33 |
| Example 206-3 | 23 |
| Example 206-4 | 45 |
| Example 206-5 | 23 |
| Example 206-6 | 34 |
| Comp. Exam. 207 | 155 |
| Example 207-1 | 30 |
| Example 207-2 | 44 |
| Example 207-3 | 35 |
| Example 207-4 | 31 |
| Example 207-5 | 23 |
| Example 207-6 | 34 |
| Comp. Exam. 208 | 165 |
| Example 208-1 | 45 |
| Example 208-2 | 42 |
| Example 208-3 | 34 |
| Example 208-4 | 21 |
| Example 208-5 | 46 |
| Example 208-6 | 41 |
| Comp. Exam. 209 | 123 |
| Example 209-1 | 31 |
| Example 209-2 | 44 |
| Example 209-3 | 33 |
| Example 209-4 | 37 |

TABLE 10-continued

| Sample | IC$_{50}$ (ppm) |
|---|---|
| Example 209-5 | 56 |
| Example 209-6 | 23 |
| Comp. Exam. 210 | 174 |
| Example 210-1 | 45 |
| Example 210-2 | 42 |
| Example 210-3 | 44 |
| Example 210-4 | 33 |
| Example 210-5 | 37 |
| Example 210-6 | 56 |

TABLE 11

| Sample | IC$_{50}$ (ppm) |
|---|---|
| Comp. Exam. 211 | 133 |
| Example 211-1 | 31 |
| Example 211-2 | 44 |
| Example 211-3 | 73 |
| Example 211-4 | 37 |
| Example 211-5 | 56 |
| Example 211-6 | 23 |
| Comp. Exam. 212 | 184 |
| Example 212-1 | 40 |
| Example 212-2 | 42 |
| Example 212-3 | 44 |
| Example 212-4 | 33 |
| Example 212-5 | 37 |
| Example 212-6 | 56 |
| Comp. Exam. 213 | 121 |
| Example 213-1 | 37 |
| Example 213-2 | 33 |
| Example 213-3 | 23 |
| Example 213-4 | 34 |
| Example 213-5 | 23 |
| Example 213-6 | 34 |
| Comp. Exam. 214 | 165 |
| Example 214-1 | 30 |
| Example 214-2 | 44 |
| Example 214-3 | 35 |
| Example 214-4 | 31 |
| Example 214-5 | 23 |
| Example 214-6 | 34 |
| Comp. Exam. 215 | 115 |
| Example 215-1 | 45 |
| Example 215-2 | 42 |
| Example 215-3 | 34 |
| Example 215-4 | 21 |
| Example 215-5 | 46 |
| Example 215-6 | 41 |
| Comp. Exam. 216 | 135 |
| Example 216-1 | 37 |
| Example 216-2 | 34 |
| Example 216-3 | 37 |
| Example 216-4 | 37 |
| Example 216-5 | 23 |
| Example 216-6 | 34 |
| Comp. Exam. 217 | 123 |
| Example 217-1 | 21 |
| Example 217-2 | 44 |
| Example 217-3 | 79 |
| Example 217-4 | 37 |
| Example 217-5 | 56 |
| Example 217-6 | 23 |
| Comp. Exam. 218 | 145 |
| Example 218-1 | 37 |
| Example 218-2 | 23 |
| Example 218-3 | 34 |
| Example 218-4 | 37 |
| Example 218-5 | 23 |
| Example 218-6 | 34 |
| Comp. Exam. 219 | 153 |
| Example 219-1 | 31 |
| Example 219-2 | 44 |
| Example 219-3 | 65 |
| Example 219-4 | 37 |

TABLE 11-continued

| Sample | IC$_{50}$ (ppm) |
|---|---|
| Example 219-5 | 56 |
| Example 219-6 | 23 |
| Comp. Exam. 220 | 211 |
| Example 220-1 | 45 |
| Example 220-2 | 42 |
| Example 220-3 | 44 |
| Example 220-4 | 33 |
| Example 220-5 | 37 |
| Example 220-6 | 56 |
| Comp. Exam. 221 | 142 |
| Example 221-1 | 40 |
| Example 221-2 | 42 |
| Example 221-3 | 44 |
| Example 221-4 | 33 |
| Example 221-5 | 37 |
| Example 221-6 | 56 |
| Comp. Exam. 222 | 154 |
| Example 222-1 | 37 |
| Example 222-2 | 33 |
| Example 222-3 | 23 |
| Example 222-4 | 43 |
| Example 222-5 | 23 |
| Example 222-6 | 34 |
| Comp. Exam. 223 | 224 |
| Example 223-1 | 31 |
| Example 223-2 | 44 |
| Example 223-3 | 65 |
| Example 223-4 | 37 |
| Example 223-5 | 56 |
| Example 223-6 | 23 |
| Comp. Exam. 224 | 104 |
| Example 224-1 | 45 |
| Example 224-2 | 42 |
| Example 224-3 | 55 |
| Example 224-4 | 33 |
| Example 224-5 | 37 |
| Example 224-6 | 56 |
| Comp. Exam. 225 | 180 |
| Example 225-1 | 40 |
| Example 225-2 | 44 |
| Example 225-3 | 36 |
| Example 225-4 | 31 |
| Example 225-5 | 37 |
| Example 225-6 | 41 |
| Comp. Exam. 226 | 160 |
| Example 226-1 | 30 |
| Example 226-2 | 54 |
| Example 226-3 | 35 |
| Example 226-4 | 37 |
| Example 226-5 | 23 |
| Example 226-6 | 34 |
| Comp. Exam. 227 | 114 |
| Example 227-1 | 45 |
| Example 227-2 | 42 |
| Example 227-3 | 34 |
| Example 227-4 | 21 |
| Example 227-5 | 47 |
| Example 227-6 | 33 |
| Comp. Exam. 228 | 135 |
| Example 228-1 | 37 |
| Example 228-2 | 23 |
| Example 228-3 | 34 |
| Example 228-4 | 37 |
| Example 228-5 | 23 |
| Example 228-6 | 34 |
| Comp. Exam. 229 | 123 |
| Example 229-1 | 31 |
| Example 229-2 | 44 |
| Example 229-3 | 33 |
| Example 229-4 | 37 |
| Example 229-5 | 56 |
| Example 229-6 | 23 |
| Comp. Exam. 230 | 174 |
| Example 230-1 | 45 |
| Example 230-2 | 42 |
| Example 230-3 | 44 |
| Example 230-4 | 33 |
| Example 230-5 | 37 |

TABLE 11-continued

| Sample | IC$_{50}$ (ppm) |
|---|---|
| Example 230-6 | 56 |
| Comp. Exam. 231 | 166 |
| Example 231-1 | 37 |
| Example 231-2 | 55 |
| Example 231-3 | 23 |
| Example 231-4 | 34 |
| Example 231-5 | 23 |
| Example 231-6 | 34 |

TABLE 12

| Sample | IC$_{50}$ (ppm) |
|---|---|
| Comp. Exam. 232 | 115 |
| Example 232-1 | 45 |
| Example 232-2 | 42 |
| Example 232-3 | 34 |
| Example 232-4 | 21 |
| Example 232-5 | 46 |
| Example 232-6 | 41 |
| Comp. Exam. 233 | 123 |
| Example 233-1 | 21 |
| Example 233-2 | 44 |
| Example 233-3 | 69 |
| Example 233-4 | 37 |
| Example 233-5 | 56 |
| Example 233-6 | 47 |
| Comp. Exam. 234 | 160 |
| Example 234-1 | 22 |
| Example 234-2 | 88 |
| Example 234-3 | 35 |
| Example 234-4 | 64 |
| Example 234-5 | 55 |
| Example 234-6 | 38 |
| Comp. Exam. 235 | 135 |
| Example 235-1 | 37 |
| Example 235-2 | 23 |
| Example 235-3 | 34 |
| Example 235-4 | 37 |
| Example 235-5 | 23 |
| Example 235-6 | 34 |
| Comp. Exam. 236 | 332 |
| Example 236-1 | 31 |
| Example 236-2 | 44 |
| Example 236-3 | 42 |
| Example 236-4 | 47 |
| Example 236-5 | 56 |
| Example 236-6 | 64 |
| Comp. Exam. 237 | 178 |
| Example 237-1 | 30 |
| Example 237-2 | 44 |
| Example 237-3 | 35 |
| Example 237-4 | 43 |
| Example 237-5 | 23 |
| Example 237-6 | 34 |
| Comp. Exam. 238 | 165 |
| Example 238-1 | 65 |
| Example 238-2 | 42 |
| Example 238-3 | 43 |
| Example 238-4 | 21 |
| Example 238-5 | 46 |
| Example 238-6 | 41 |

As can be seen in Tables 1 to 12 above, the extracts of processed medicinal plants according to Examples of the present invention showed a significant inhibition of DPPH oxidation compared to the extracts of unprocessed medicinal plants of Comparative Examples, suggesting that the extracts of Examples of the preset invention showed significantly excellent antioxidant activities. Also, the extracts of Examples mostly showed excellent antioxidant activity compared to the synthetic antioxidant Trolox.

The invention claimed is:

1. A method of preparing a medicinal plant extract using Chinese herbal medicine processing, comprising the steps of:
   (a) processing at least one medicinal plant by honey-roasting the at least one medicinal plant to obtain a processed plant material;
   (b) drying the processed plant material before step (c); and
   (c) obtaining extracts of the at least one medicinal plant from the processed plant material using ethanol,
   wherein the honey-roasting comprises mixing the medicinal plant with honey, and roasting the medicinal plant at 100-160° C. for 10 minutes to 1 hour,
   and wherein the at least one medicinal plant in the step (a) is at least one selected from the group consisting of Rehmanniae radix, dried ginger, Lycii fructus, Lonicera japonica flower, Chrysanthemum indicum, Phaseolus aureus, Citrus grandis, Datura stramonium, Codonopsis pilosulae radix, Akebiae caulis, Mentha arvensis, Pulsatilla koreana root, Santalum album, Hedyotis diffusa, Atractylodes macrocephala rhizome, Luffa cylindrica, Zizyphi spinosi semen, Dichroa febrifuga, Agrimonia pilosa ledebour, Linderae radix, Polygonatum odoratum root, Euphoria longana testa, Genkwa flos, Epimedium koreanum, Angelica acutiloba root, Cnidium officinale, Adenophora triphylla, red cabbage, Sanguisorba officinalis, Sorbus commixta cortex, Asparagus cochinchinensis, Celosiae semen, Smilacis chinae radix, Medulla tetrapanacis, Polygonum multiflorum tuber, Armeniacae semen, Scrophulariae radix, Corydalis turtschaninovii, Cucurbita spp., and Lindera obtusiloba branch.

2. The method according to claim 1 further comprising:
   (d) concentrating the extracts of the at least one medicinal plant.

3. The method according to claim 2, wherein the concentrating of step (d) occurs under reduced pressure.

\* \* \* \* \*